US012577624B2

(12) United States Patent
Brzostowski et al.

(10) Patent No.: US 12,577,624 B2
(45) Date of Patent: Mar. 17, 2026

(54) TRANSGENIC CORN EVENT ZM_BCS216090 AND METHODS FOR DETECTION AND USES THEREOF

(71) Applicant: Monsanto Technology LLC, St. Louis, MO (US)

(72) Inventors: Lillian Brzostowski, Wildwood, MO (US); Carrin Carlson, Wildwood, MO (US); Kelly Gillespie, Ballwin, MO (US); Tomasz Paciorek, Wildwood, MO (US); Lyle Ralston, Kirkwood, MO (US); Alexandar Renaud, St. Louis, MO (US); Heping Yang, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 111 days.

(21) Appl. No.: 18/047,808

(22) Filed: Oct. 19, 2022

(65) Prior Publication Data

US 2023/0279508 A1     Sep. 7, 2023

Related U.S. Application Data

(60) Provisional application No. 63/279,508, filed on Nov. 15, 2021, provisional application No. 63/274,865, filed on Nov. 2, 2021.

(51) Int. Cl.
*C12N 15/82* (2006.01)
*C12Q 1/6895* (2018.01)

(52) U.S. Cl.
CPC ....... *C12Q 1/6895* (2013.01); *C12N 15/8297* (2013.01); *C12Q 2600/13* (2013.01)

(58) Field of Classification Search
CPC .................................................. C12Q 1/6895
USPC ........................................................ 800/275
See application file for complete search history.

(56) References Cited

U.S. PATENT DOCUMENTS

| | | | |
|---|---|---|---|
| 5,159,135 A | 10/1992 | Umbeck | |
| 5,188,958 A | 2/1993 | Moloney et al. | |
| 5,322,938 A | 6/1994 | McPherson et al. | |
| 5,352,605 A | 10/1994 | Fraley et al. | |
| 5,463,174 A | 10/1995 | Moloney et al. | |
| 5,510,474 A | 4/1996 | Quail et al. | |
| 5,538,880 A | 7/1996 | Lundquist et al. | |
| 5,550,318 A | 8/1996 | Adams et al. | |
| 5,591,616 A | 1/1997 | Hiei et al. | |
| 5,641,876 A | 6/1997 | McElroy et al. | |
| 5,750,871 A | 5/1998 | Moloney et al. | |
| 5,824,877 A | 10/1998 | Hinchee et al. | |
| 5,850,019 A | 12/1998 | Maiti et al. | |
| 5,939,539 A | 8/1999 | Lange et al. | |
| 6,153,812 A | 11/2000 | Fry et al. | |
| 6,160,208 A | 12/2000 | Lundquist et al. | |

| | | | |
|---|---|---|---|
| 6,372,211 B1 | 4/2002 | Isaac et al. | |
| 6,380,467 B1 | 4/2002 | Duclos | |
| 6,384,301 B1 | 5/2002 | Martinell et al. | |
| 6,399,861 B1 | 6/2002 | Anderson et al. | |
| 6,420,547 B1 | 7/2002 | Maiti et al. | |
| 6,429,357 B1 | 8/2002 | McElroy et al. | |
| 6,723,897 B2 | 4/2004 | Brown et al. | |
| 7,041,874 B2 | 5/2006 | Johal et al. | |
| 7,049,490 B2 | 5/2006 | Tanaka et al. | |
| 7,057,088 B2 | 6/2006 | Tanaka et al. | |
| 7,138,567 B2 | 11/2006 | Okawa et al. | |
| 7,154,028 B2 | 12/2006 | Tanaka et al. | |
| 7,597,055 B2 | 10/2009 | Choulet | |
| 8,835,353 B2 | 9/2014 | Fugiel et al. | |
| 8,843,283 B2 | 9/2014 | Strelioff et al. | |
| 9,012,722 B2 | 4/2015 | Narva et al. | |
| 9,040,774 B2 | 5/2015 | Ivashuta et al. | |
| 9,303,919 B2 | 4/2016 | Hultgren et al. | |
| 9,309,512 B2 | 4/2016 | Allen et al. | |
| 9,845,479 B2 | 12/2017 | Beghyn et al. | |
| 10,472,684 B2 | 11/2019 | Barten et al. | |
| 10,724,047 B2 | 7/2020 | Allen et al. | |
| 10,881,057 B2 | 1/2021 | Cannon et al. | |
| 11,632,921 B2 | 4/2023 | Cannon et al. | |
| 11,737,404 B2 | 8/2023 | Jolliffe et al. | |
| 2002/0053095 A1 | 5/2002 | Brown et al. | |
| 2002/0162142 A1 | 10/2002 | Johal et al. | |

(Continued)

FOREIGN PATENT DOCUMENTS

| | | |
|---|---|---|
| AU | 2016203359 B2 | 3/2018 |
| CN | 101440374 A | 5/2009 |

(Continued)

OTHER PUBLICATIONS

Fourgoux-Nicol et al Plant Molecular Biology 40 :857-872 (Year: 1999).*
Thomison et al., Corn Response to Harvest Date as Affected by Plant Population and Hybrid, Agronomy Journal 103 (6): 1765-1772, 2011.
Bage et al., Genetic characterization of novel and CRISPR-Cas9 gene edited maize brachytic 2 alleles, Plant Gene 21:100198, 2020.
Bolduc and Hake, The maize transcription factor Knotted1 directly regulates the gibberellin catabolismgene ga2ox1, Plant Cell 21:1647-1658, 2009.

(Continued)

*Primary Examiner* — Li Zheng
(74) *Attorney, Agent, or Firm* — Dentons US LLP; David Lanzotti

(57) ABSTRACT

The invention provides a transgenic corn event ZM_BCS216090, plants, plant cells, seeds, plant parts, progeny plants, and commodity products comprising event ZM_BCS216090. The invention also provides polynucleotides and sequences specific for event ZM_BCS216090 and methods for using plants, plant cells, seeds, plant parts, progeny plants, and commodity products comprising event ZM_BCS216090 and detecting event ZM_BCS216090, or a polynucleotide or DNA sequence specific for event ZM_BCS216090, in a DNA molecule or sample.

33 Claims, 6 Drawing Sheets

Specification includes a Sequence Listing.

(56) References Cited

U.S. PATENT DOCUMENTS

| | | |
|---|---|---|
| 2003/0172409 A1 | 9/2003 | Horn |
| 2003/0233679 A1 | 12/2003 | Brown et al. |
| 2004/0053411 A1 | 3/2004 | Cullen et al. |
| 2004/0121321 A1 | 6/2004 | Brown et al. |
| 2004/0268441 A1 | 12/2004 | Vance et al. |
| 2005/0037988 A1 | 2/2005 | Zamore et al. |
| 2005/0064474 A1 | 3/2005 | Umov et al. |
| 2005/0144669 A1 | 6/2005 | Reinhart et al. |
| 2005/0197253 A1 | 9/2005 | Stoller et al. |
| 2005/0251883 A1 | 11/2005 | Amasino et al. |
| 2006/0200878 A1 | 9/2006 | Lutfiyya et al. |
| 2006/0253933 A1 | 11/2006 | Brown et al. |
| 2007/0174931 A1 | 7/2007 | Brown et al. |
| 2007/0294789 A1 | 12/2007 | Ghiglione et al. |
| 2008/0034453 A1 | 2/2008 | Cheikh et al. |
| 2009/0031441 A1 | 1/2009 | Matsuoka et al. |
| 2009/0070898 A1 | 3/2009 | Allen et al. |
| 2009/0117617 A1 | 5/2009 | Holmes et al. |
| 2009/0313725 A1 | 12/2009 | Yu et al. |
| 2010/0095406 A1 | 4/2010 | Yu et al. |
| 2010/0107283 A1 | 4/2010 | Dasgupta et al. |
| 2011/0004958 A1 | 1/2011 | Aloni et al. |
| 2011/0035839 A1 | 2/2011 | Lutfiyya et al. |
| 2011/0145940 A1 | 6/2011 | Voytas et al. |
| 2011/0167517 A1 | 7/2011 | Danilevskaya et al. |
| 2011/0185456 A1 | 7/2011 | Cheikh et al. |
| 2011/0296555 A1 | 12/2011 | Ivashuta et al. |
| 2011/0301073 A1 | 12/2011 | Gregory et al. |
| 2012/0142062 A1 | 6/2012 | Doyon et al. |
| 2012/0174260 A1 | 7/2012 | Narva et al. |
| 2012/0216318 A1 | 8/2012 | La Rosa et al. |
| 2012/0297501 A1 | 11/2012 | Beghyn et al. |
| 2013/0117869 A1 | 5/2013 | Duchateau et al. |
| 2013/0121101 A1 | 5/2013 | Ochampaugh et al. |
| 2013/0260012 A1 | 10/2013 | Rommens et al. |
| 2013/0283461 A1 | 10/2013 | Abad et al. |
| 2013/0345937 A1 | 12/2013 | Strelioff et al. |
| 2014/0013464 A1 | 1/2014 | Davie et al. |
| 2014/0074360 A1 | 3/2014 | Rosa et al. |
| 2014/0165228 A1 | 6/2014 | Danilevskaya et al. |
| 2014/0230087 A1 | 8/2014 | Hartig et al. |
| 2014/0344996 A1 | 11/2014 | Inze et al. |
| 2015/0052634 A1 | 2/2015 | Park et al. |
| 2015/0201619 A1 | 7/2015 | Annigeri et al. |
| 2015/0240253 A1 | 8/2015 | McGonigle et al. |
| 2015/0247154 A1 | 9/2015 | Ivashuta et al. |
| 2015/0307889 A1 | 10/2015 | Petolino et al. |
| 2015/0376641 A1 | 12/2015 | Etzioni et al. |
| 2016/0010109 A1 | 1/2016 | Albertsen et al. |
| 2016/0017349 A1 | 1/2016 | Ayele et al. |
| 2016/0046956 A1 | 2/2016 | Yu et al. |
| 2016/0050865 A1 | 2/2016 | Morse et al. |
| 2016/0050920 A1 | 2/2016 | Ott et al. |
| 2016/0076046 A1 | 3/2016 | Alexandrov et al. |
| 2016/0157415 A1 | 6/2016 | Cavender-Bares et al. |
| 2016/0319375 A1 | 11/2016 | Barten et al. |
| 2017/0079224 A1 | 3/2017 | Jolliffe et al. |
| 2019/0246619 A1 | 8/2019 | Barten et al. |
| 2020/0032289 A1 | 1/2020 | Anderson et al. |
| 2021/0032649 A1 | 2/2021 | Manjunath et al. |
| 2021/0332380 A1 | 10/2021 | Brown et al. |
| 2022/0364108 A1 | 11/2022 | Allen et al. |
| 2023/0110884 A1 | 4/2023 | Allen et al. |
| 2023/0323381 A1 | 10/2023 | Cannon et al. |

FOREIGN PATENT DOCUMENTS

| | | |
|---|---|---|
| CN | 102149821 A | 8/2011 |
| CN | 102174519 A | 9/2011 |
| CN | 104388580 | 3/2015 |
| EP | 1398382 B1 | 11/2005 |
| JP | 3829157 B2 | 10/2006 |
| KR | 20150045611 A | 4/2015 |
| RU | 2013135491 A | 2/2015 |
| RU | 2013151447 A | 5/2015 |

| | | |
|---|---|---|
| WO | WO 94/28141 A1 | 12/1994 |
| WO | WO 99/09174 A1 | 2/1999 |
| WO | WO 99/66029 A2 | 12/1999 |
| WO | WO 00/009722 A2 | 2/2000 |
| WO | WO 02/055725 A2 | 7/2002 |
| WO | WO 03/008540 A2 | 1/2003 |
| WO | WO 2006/032916 A2 | 3/2006 |
| WO | WO 2008/034648 A1 | 3/2008 |
| WO | WO 2010/002984 A1 | 1/2010 |
| WO | WO 2011/023537 A1 | 3/2011 |
| WO | WO 2013/037959 A1 | 3/2013 |
| WO | WO 2013/086499 A2 | 6/2013 |
| WO | WO 2014/055477 A2 | 4/2014 |
| WO | WO 2014/151749 A1 | 9/2014 |
| WO | WO 2015/168124 A1 | 11/2015 |
| WO | WO 2016/176286 | 11/2016 |
| WO | 2018035354 A1 | 2/2018 |
| WO | 2018119225 | 6/2018 |
| WO | WO 2018/129302 | 7/2018 |

OTHER PUBLICATIONS

R4038-sprayer by John Deere, available at https://kibbleeq.com/farmers/sprayers-&-applicators/self-propelled-sprayers/john-deere-sprayers/r4038-sprayer, accessed Apr. 29, 2024.
Sun et al., Identification and characterization of EI (Elongated Internode) gene in tomato (Solanum lycopersicum), Int. J. Mol. Sci. 20(2204):1-18, 2019.
Bowler, et al. Phaeodactylum tricornutum CCAP 1055/1 predicted protein partial mRNA. NCBI Reference Sequence: XM_002181742. 1. National Center for Biotechnology Information. Dated Jun. 16, 2017.
Caccone, et al. Drosophila yakuba nullo gene, partial cds. GenBank Accession No. U44732.1. National Center for Biotechnology Information. Dated Feb. 8, 1997.
Chen, et al. CRISPR-Based Assessment of Gene Specialization in the Gibberellin Metabolic Pathway in Rice. Plant Physiology, vol. 180, Issue 4, pp. 2091-2105, (2019).
Han, et al. Generation of semi-dwarf rice (Oryza sativa L.) lines by CRISPR/Cas9-directed mutagenesis of OsGA20ox2 and proteomic analysis of unveiled changes caused by mutations. 3 Biotech 9, 387 (2019).
Hedden, et al. Gibberellin biosynthesis and its regulation. Biochem J (2012) 444 (1): 11-25, (2012).
Hedden, et al. A Century of Gibberellin Research. J Plant Growth Regul 34, 740-760 (2015).
Kaneko, et al. Where do gibberellin biosynthesis and gibberellin signaling occur in rice plants? The Plant Journal, vol. 35, Issue 1, pp. 104-115, (2003).
Kovalic, et al. The Use of Next Generation Sequencing and Junction Sequence Analysis Bioinformatics to Achieve Molecular Characterization of Crops Improved Through Modern Biotechnology. The Plant Genome, vol. 5, Issue 3, pp. 149-163, (2012).
Luo, et al. A Single Nucleotide Deletion in Gibberellin20-oxidase1 Causes Alpine Dwarfism in Arabidopsis. Plant Physiology, vol. 168, Issue 3, pp. 930-937, (2015).
Muramatsu, et al. Drosophila melanogaster DNA, chromosome 2R, 43A1, GS vector insertion site flanking region, clone: 14174-5p-6. seq. GenBank Accession No. AB317463.1. National Center for Biotechnology Information. Dated Jun. 13, 2007.
Qin, et al. Gibberellin 20-Oxidase Gene OsGA20ox3 Regulates Plant Stature and Disease Development in Rice. Molecular Plant-Microbe Interactions, vol. 26, No. 2, pp. 227-239, (2013).
Voorend, et al. Overexpression of GA20-OXIDASE1 impacts plant height, biomass allocation and saccharification efficiency in maize. Plant Biotechnology Journal, vol. 14, Issue 3, pp. 997-1007, (2016).
Yamaguchi. Gibberellin Metabolism and its Regulation. Annual Review of Plant Biology, vol. 59, pp. 225-251, (2008).
Zhang, et al. Generation of transgene-free semidwarf maize plants by gene editing of gibberellin-oxidase20-3 using CRISPR/Cas9. Front Plant Sci. 11:1048, (2020).
National Center for Biotechnology Information. Predicted: Alligator mississippiensis LSM5 homolog, U6 small nuclear RNA and mRNA

(56)          References Cited

OTHER PUBLICATIONS degradation associated (LSM5), mRNA. NCBI Reference Sequence: XM_006258198.3, National Center for Biotechnology Information. Dated Dec. 9, 2016.

Invitation to Pay Additional Fees regarding International App. No. PCT/US22/78966, mailed Jan. 11, 2023.

International Search Report and Written Opinion regarding International App. No. PCT/US22/78966, mailed May 4, 2023.

Anonymous, Proceedings of the Caribbean Food Crops Society Fourth Annual Meeting, 1996.

D'Andrea et al., Genotypic Variability in Morphological and Physiological Traits among Maize Inbred Lines—Nitrogen Responses, Crop Science 46(3):1266-1276, 2006.

Search Report dated Jul. 21, 2022, in Chinese Application 2017800639820 including English translation of related Office Action.

Allen, et al., "Evolution of microRNA genes by inverted duplication of target gene sequences in *Arabidopsis thaliana*," Nature Genetics, 36:1282-1290 (2004).

Allen, et al., "microRNA-directed phasing during Trans-acting siRNA Biogenesis in plants," Cell, 121(2):207-221 (2005).

Altschul, et al., "Basic Local Alignment Search Tool," Journal of Molecular Biology, 215(3):403-410 (1990).

Altschul, et al., "Gapped BLAST and PSI-BLAST: a new generation of protein database search programs," Nucleic Acids Research, 25 (17) : 3389-3402 (1997).

Ashikari, et al., "Loss-of-function of a Rice Gibberellin Biosynthetic Gene, GA20 oxidase (GA20ox-2), Led to the Rice 'Green Revolution'," Breeding Science, 52:143-150 (2002).

Axtell, et al., "A Two-Hit Trigger for siRNA Biogenesis in Plants," Cell, 127:565-577 (2006).

Beurdeley, et al., "Compact designer TALENs for efficient genome engineering", Nature Communications, 4: 1762 (2013).

Cai, et al., "Molecular Cloning, Characterization, and Expression Analysis of Genes Encoding Gibberellin 20-Oxidase in *Dasypyrum villosum* Dwarf Mutant," Plant Molecular Biology Reporter, 30:1110-1116 (2012).

Carrera, et al.,"Changes in GA 20-oxidase gene expression strongly affect stem length, tuber induction and tuber yield of potato plants," The Plant Journal, 22(3):247-256 (2000).

Cermak, et al., "Efficient design and assembly of custom TALEN and other TAL effector-based constructs for DNA targeting," Nucleic Acids Research, 39(12):e82 (2011).

Chen, et al., "Identification and Functional Analysis of Flowering Related microRNAs in Common Wild Rice (*Oryza rufipogon* Griff.)," PLoS One, 8:e82844 (2013).

Chen, et al., "New insight in the Gibberellin biosynthesis and signal transduction," Plant Signaling & Behavior, 10(5):e1000140-1-e1000140-3:(2015).

Chen, et al., "The Maize DWARF1 Encodes a Gibberellin 3-Oxidase and Is Dual Localized to the Nucleus and Cytosol," Plant Physiology, 166:2028-2039 (2014).

Chenna, et al., "Multiple sequence alignment with the Clustal series of programs," Nucleic Acids Research, 31(13):3497-3500 (2003).

Ciampitti, et al., "A comprehensive study of plant density consequences on nitrogen uptake dynamics of maize plants from vegetative to reproductive stages," Field Crops Research, 121(1):2-18 (2011).

Coles, et al., "Modification of gibberellin production and plant development in *Arabidopsis* by sense and antisense expression of gibberellin 20-oxidase genes," The Plant Journal, 17(5):547-556 (1999).

Davis, et al., "Gibberellin Biosynthesis in Maize. Metabolic Studies with $GA_{15}$, $GA_{24}$, $GA_{25}$, $GA_7$, and 2,3-Dehydro-$GA_9{}^1$," Plant Physiology, 121(3):1037-1045 (1999).

Doyle, et al., "TAL Effector-Nucleotide Targeter (TALE-NT) 2.0: tools for TAL effector design and target prediction," Nucleic Acids Research, 40:W117-122 (2012).

Du, et al., "Cloning and characterization of an up-regulated GA 20-oxidase gene in hybrid maize," Natural Science, 19(2):161-166 (2009).

Eriksson, et al., "GA4 Is the Active Gibberellin in the Regulation of LEAFY Transcription and *Arabidopsis* Floral Initiation," The Plant Cell, 18(9):2172-2181 (2006).

Obel, Extended European Search Report dated Mar. 9, 2020, in European Patent Application No. 17842139.2.

Fagoaga, et al., "Engineering of gibberellin levels in citrus by sense and antisense overexpression of a GA 20-oxidase gene modifies plant architecture," Journal of Experimental Botany, 58(6):1407-1420 (2007).

Fambrini, et al., "The extreme dwarf phenotype of the GA-sensitive mutant of sunflower, dwarf2, is generated by a deletion in the ent-kaurenoic acid oxidase1 (HaKAO1) gene sequence," Plant Molecular Biology, 75:431-450 (2011).

Franco-Zorrilla, et al., "Target mimicry provides a new mechanism for regulation of microRNA activity," Nature Genetics, 39: 1033-1037 (2007).

Gabsalilow, et al., "Site- and strand-specific nicking of DNA by fusion proteins derived from MutH and I-SceI or TALE repeats," Nucleic Acids Research, 41(7):e83 (2013).

Gaj, et al.. "ZFN, TALEN, and CRISPR/Cas-based methods for genome engineering," Trends Biotechnology, 31(7):397-405 (2013).

GenBank Accession No. AY105651.1, "*Zea mays* PC0130567 mRNA sequence," pp. 1-2, dated May 28, 2008.

GenBank Accession No. BT068785.2, "*Zea mays* full-length cDNA clone ZM_BFb0382B03 mRNA, complete cds," pp. 1-2, dated Jun. 15, 2012.

GenBank Accession No. EU963664.1, "*Zea mays* clone 265382 gibberellin 20 oxidase 2 mRNA, complete cds," pp. 1, dated Dec. 10, 2008.

Griffiths-Jones, et al., "Rfam: an RNA family database," Nucleic Acids Research, 31(1):439-441 (2003).

Gupta, et al., "Gibberellic acid in plant Still a mystery unresolved," Plant Signaling & Behavior, 8(9):e25504 (2013).

Han, et al., "Gibberellin-associated cisgenes modify growth, stature and wood properties in Populus," Plant Biotechnology Journal, 9(2):162-178 (2011).

Hedden, et al., "Gibberellin Biosynthesis: Enzymes, Genes and Their Regulation," Annu. Rev. Plant Physiol. Plant Mol. Biol., 48:431-60 (1997).

Hedden, "The genes of the Green Revolution," Trends in Genetics, 19(1):5-9 (2003).

Helliwell, et al "Constructs and Methods for Hairpin RNA-Mediated Gene Silencing in Plants," Methods in Enzymology, 392:24-35 (2003).

Huang, et al., "A Gibberellin-Mediated DELLA-NAC Signaling Cascade Regulates Cellulose Synthesis in Rice," The Plant Cell, 27(6):1681-1696 (2015).

Copenheaver. International Search Report and Written Opinion mailed Dec. 28, 2017, in International Application No. PCT/US2017/047405.

Jia, et al., "GA-20 oxidase as a candidate for the semidwarf gene sdw1/denso in barley," Functional & Integrative Genomics, 9:255-262 (2009).

Jia, et al., "Molecular characterization and functional analysis of barley semi-dwarf mutant Riso No. 9265," BMC Genomics, 16(927):1-11 (2015).

Jones-Rhoades, et al., "Computational Identification of Plant MicroRNAs and Their Targets, Including a Stress-Induced miRNA," Molecular Cell, 14(6):787-799 (2004).

Kamthan, et al., "Small RNAs in plants: recent development and application for crop improvement" Frontiers in Plant Science, 6:1-17 (2015).

Katoh, et al., "Specific residues at every third position of siRNA shape its efficient RNAi activity," Nucleic Acids Research, 35(4):e27 (2007).

Khvorova, et al., "Functional siRNAs and miRNAs Exhibit Strand Bias," Cell, 115(2):209-216 (2003).

Kim, "MicroRNA Biogenesis: Coordinated Cropping and Dicing," Nature Reviews Molecular Cell Biology, 6:376-385 (2005).

(56)　　　　　　　References Cited

OTHER PUBLICATIONS

King, et al., "Selective Deactivation of Gibberellins below the Shoot Apex is Critical to Flowering but Not to Stem Elongation of Lolium," Molecular Plant, 1(2):295-307 (2008).

Kobayashi, et al., "Gibberellin Metabolism in Maize (The Stepwise Conversion of Gibberellin $A_{12}$-Aldehyde to Gibberellin $A_{20}$)," Plant Physiology, 110(2):413-418 (1996).

Kusaba, et al., "Isolation and expression analysis of gibberellin 20-oxidase homologous gene in apple," Journal of Experimental Botany, 52(335):375-376 (2001).

Lange, et al., "Gibberellin Biosynthesis and the Regulation of Plant Development," Plant Biology, 8(3):281-290 (2006).

Larkin, et al., "Clustal W and Clustal X version 2.0," Bioinformatics, 23(21):2947-48 (2007).

Liu, et al., "Analysis of Complementarity Requirements for Plant MicroRNA Targeting Using a Nicotiana benthamiana Quantitative Transient Assay," The Plant Cell, 26(2):741-753 (2014).

McElroy, et al., "Construction of expression vectors based on the rice actin 1 (Act1) 5' region for use in monocot transformation," Molecular and General Genetics MGG, 231:150-160 (1991).

Mitchum, et al., "Distinct and overlapping roles of two gibberellin 3-oxidases in Arabidopsis development," The Plant Journal, 45(5):804-818 (2006).

Molina, et al., "Transformation of a Dwarf Arabidopsis Mutant Illustrates Gibberellin Hormone Physiology and the Function of a Green Revolution Gene," Biochemistry and Molecular Biology Education, 37(3): 170-177 (2009).

Mutasa-Gottgens, et al., "Gibberellin as a factor in floral regulatory networks," Journal of Experimental Botany, 60(7):1979-1989 (2009).

Offtype—Definition of Offtype by Merriam-Webster, pp. 1, retrieved Sep. 18, 2023 <https://www.merriam-webster.com/dictionary/offtype>.

Oikawa, et al., "A role of OsGA20ox1, encoding an isoform of gibberellin 20-oxidase, for regulation of plant stature in rice," Plant Molecular Biology, 55:687-700 (2004).

Ookawa, et al., "Precise estimation of genomic regions controlling lodging resistance using a set of reciprocal chromosome segment substitution lines in rice," Scientific Reports, 6(30572) pp. 1-12 (2016).

Parizotto, et al., "In vivo investigation of the transcription, processing, endonucleolytic activity, and functional relevance of the spatial distribution of a plant miRNA," Genes & Development, 18:2237-2242 (2004).

Pater, et al., "The promoter of the rice gene GOS2 is active in various different monocot tissues and binds rice nuclear factor ASF-1," The Plant Journal, 2(6):837-844 (1992).

Peiffer, et al., "The Genetic Architecture Of Maize Height," Genetics, 196(4):1337-1356 (2014).

Peng, et al., "'Green revolution' genes encode mutant gibberellin response modulators," Nature, 400:256-261 (1999).

Petti, et al., "Mapping of a Cellulose-Deficient Mutant Named dwarf1-1 in Sorghum bicolor to the Green Revolution Gene gibberellin20-oxidase Reveals a Positive Regulatory Association between Gibberellin and Cellulose Biosynthesis," Plant Physiology, 169(1):705-716 (2015).

Plackett, et al., "Analysis of the Developmental Roles of the Arabidopsis Gibberellin 20-Oxidases Demonstrates That GA20ox1, -2, and -3 Are the Dominant Paralogs," The Plant Cell, 24(3):941-960 (2012).

Qiao, et al., "Alteration of rice growth and development via antisense expression of OsGA20ox2 gene," African Journal of Biotechnology, 12(25):3898-3904 (2013).

Qiao, et al., "Modification of plant height via RNAi suppression of OsGA20ox2 gene in rice," Euphytica, 158:35-45 (2007).

Qiao, et al., "The Influence of RNAi Targeting of OsGA20ox2 Gene on Plant Height in Rice," Plant Molecular Biology Reporter, 29:952-960 (2011).

Reynolds, et al., "Rational siRNA design for RNA interference," Nature Biotechnology, 22(3):326-330 (2004).

Rhoades, et al., "Prediction of Plant MicroRNA Targets," Cell, 110(4):513-520 (2002).

Rieu, et al., "The gibberellin biosynthetic genes AtGA20ox1 and AtGA20ox2 act, partially redundantly, to promote growth and development throughout the Arabidopsis life cycle," The Plant Journal, 53:488-504 (2008).

Ross, et al., "Gibberellin mutants," Physiologia Plantarum, 100(3):550-560 (1997).

Sarkar, et al., "Relationship between gibberellins, height, and stress tolerance in barley (Hordeum vulgare L.) seedlings," Plant Growth Regulation, 42:125-135 (2004).

Sasaki, et al., "A mutant gibberellin-synthesis gene in rice," Nature, 416:701-702 (2002).

Gromova, Search Report dated Jun. 24, 2021, in Russian Patent Application 2019105536, and English translation of the same (pp. 1-4).

Singh, "The green revolution and the evolution of agricultural education and research in India," Genome, 42(4):557-561 (1999).

Song, et al., "Association of the molecular regulation of ear leaf senescence/stress response and photosynthesis/metabolism with heterosis at the reproductive stage in maize," Scientific Reports, 6:29843 (2016).

Song, et al., "Flowering time regulation: photoperiod- and temperature-sensing in leaves," Trends in Plant Science, 18(10):575-583 (2013).

Song, et al., "Genome-wide identification of gibberellins metabolic enzyme genes and expression profiling analysis during seed germination in maize," Gene, 482(1-2):34-42 (2011).

Spielmeyer, et al., "Semidwarf (sd-1), "green revolution" rice, contains a defective gibberellin 20-oxidase gene," PNAS, 99(13):9043-9048 (2002).

Sun, "Gibberellin Metabolism, Perception and Signaling Pathways in Arabidopsis," The Arabidopsis Book, 2008(6): pp. 1-28 (2008).

Sunkar, et al., "Novel and Stress-Regulated MicroRNAs and Other Small RNAs from Arabidopsis," Plant Cell, 16(8):2001-2019 (2004).

Obel, Supplementary Partial European Search Report dated Jan. 14, 2020, in European Patent Application No. 17842139.2.

Svitashev, et al., "Targeted Mutagenesis, Precise Gene Editing, and Site-Specific Gene Insertion in Maize Using Cas9 and Guide RNA," Plant Physiology, 169(2):931-945 (2015).

Teng, et al., "ZmGA3ox2, a candidate gene for a major QTL, qPH3.1, for plant height in maize," The Plant Journal, 73(3):405-416 (2013).

Thompson, et al., "Clustal W: improving the sensitivity of progressive multiple sequence alignment through sequence weighting, position-specific gap penalties and weight matrix choice," Nucleic Acids Research, 22(22):4673-4680 (1994).

Tollenaar, et al., "Effect of Defoliation on Kernel Development in Maize," Canadian Journal of Plant Science, 58(1):207-212 (1978).

Tong, et al., "Reply: Brassinosteroid Regulates Gibberellin Synthesis to Promote Cell Elongation in Rice: Critical Comments on Ross and Quittenden's Letter," The Plant Cell, vol. 28, pp. 833-835, (2016).

Traore, et al., "Bt and Non-Bt Maize Growth and Development as Affected by Temperature and Drought Stress," Agronomy Journal, 92(5): 1027-1035 (2000).

Unterholzner, et al., "Reply: Interaction Between Brassinosteroids and Gibberellins: Synthesis or Signaling? In Arabidopsis Both!," The Plant Cell, vol. 28, pp. 836-839, (2016).

Urakami, et al., "Immunomodulation of gibberellin biosynthesis using an anti-precursor gibberellin antibody confers gibberellin-deficient phenotypes," Planta, 228:863-873 (2008).

Voytas, "Plant Genome Engineering with Sequence-Specific Nucleases," Annual Review of Plant Biology, 64:327-50 (2013).

Wang, et al., "Gibberellin Biosynthetic Deficiency Is Responsible for Maize Dominant Dwarf11 (D11) Mutant Phenotype: Physiological and Transcriptomic Evidence," PLoS One, 8(6):e66466:1-8 (2013).

Wang, et al., "More than meets the eye? Factors that affect target selection by plant miRNAs and heterochromatic siRNAs," Current Opinion Plant Biology, 27:118-124 (2015).

Weng, et al., "Genome-Wide Association Study Identifies Candidate Genes That Affect Plant Height in Chinese Elite Maize (Zea mays L.) Inbred Lines," PLoS One, 6(12):e29229 pp. 1-8 (2011).

Wu, et al., "Target specificity of the CRISPR-Cas9 system," Quantitative Biology, 2(2):59-70 (2014).

(56) References Cited

OTHER PUBLICATIONS

Xiao, et al., "Dissection of GA 20-oxidase members affecting tomato morphology by RNAi-mediated silencing," Plant Growth Regulation, 50:179-189 (2006).

Yamaguchi, et al., "Gibberellin Acts Positively Then Negatively to Control Onset of Flower Formation in *Arabidopsis*," Science, 344(6184):638-641 (2014).

Yamaguchi, "Gibberellin Metabolism and its Regulation," Annual Review of Plant Biology, 59:225-251 (2008).

Yanik, et al., "TALE-Pvull Fusion Proteins—Novel Tools for Gene Targeting," PLoS One, 8(12):e82539 pp. 1-13 (2013).

Yin, et al., "In-Season Prediction of Com Yield Using Plant Height under Major Production Systems," Agronomy Journal, 103(3):923-929 (2011).

Yoshikawa, et al., "A pathway for the biogenesis of trans-acting siRNAs in *Arabidopsis*," Genes & Development, 19:2164-2175 (2005).

Zeng, et al., "Both Natural and Designed Micro RNAs Can Inhibit the Expression of Cognate mRNAs When Expressed in Human Cells," Molecular Cell, 9(6): 1327-1333 (2002).

Rodriquez. Invitation to Pay Additional Fees for Application No. PCT/US23/62985 mailed May 23, 2023.

Rodriquez. International Search Report and Written Opinion for Application No. PCT/US23/62985 mailed Jul. 27, 2023.

Xia, et al., "A book to understand high corn yield and disaster prevention and reduction technology", China Farmers Press, May 2016, p. 135.

Zhang, Chinese Office Action regarding Chinese Patent Application No. 201980025083.0, dated Dec. 1, 2023, 19 pages.

Hill and Furrow, "Pinch or Push Your Corn: Scouting for Lodging Potential", University of Illinois Urbana-Champaign, Illinois Extension, Sep. 12, 2016, 2 pages.

Pilu, et al., "Isolation and Characterization of a new mutant allele of brachytic 2 maize gene", Mol Breeding 20, 83-91, (2007).

"4 Series Sprayers", Published in May 2016, obtained from https://www.deere.com/en_CAF/docs/product/equipment/4_Series_Sprayers.pdf.

Mourtzinis, et al., "Corn Grain and Stover Yield Prediction at R1 Growth Stage." Agronomy Journal, vol. 105 (4), pp. 1045-1050, (2013).

Kollner, et al. "Herbivore-Induced SABATH Methyltransferases of Maize that Methylate Anthranilic Acid Using S-Adenosyl-L-Methionine." Plant Physiology, vol. 153, pp. 1795-1807, (2010).

Zhang, et al. "Maize brachtic2 (br2) suppresses the elongation of lower internodes for excessive auxin accumulation in the intercalary meristem region." BMC Plant Biology, 19:589, (2019).

Butzen, Timing Corn Harvest, Crop Insights from Agronomy Sciences, accessed pioneer.com/us/agronomy/timing-corn-harvest.html Nov. 4, 2024.

Chen et al., Identification and genetic mapping for rht-DM, a dominant dwarfing gene in mutant semi-dwarf maize using QTL-seq approach, Genes Genomics 40(10):1091-1099, 2018.

Chen et al., Development of dwarfish and yield-effective GM maize through passivation and bioactive gibberlin, Transgenic Res. 28:589-599, 2019.

Crommelinck et al., Simulating an autonomously operating low-cost static terrestrial LiDAR for multitemporal maize crop height measurements, Remote Sensing 8(3):205, 2016.

Elmore et al., In-field drydown rates and harvest, Iowa State University Extension and Outreach, 2010.

Spelhaug, Predicting Your Corn Harvest Date, Peterson Farms Seed, 2013.

Zaidi et al., Phenotyping for abiotic stress tolerance in maize-heat stress, A field manual, CIMMYT: Hyderabad India 229, 2016.

Cox, W. et al., "Row Spacing, Hybrid, and Plant Density Effects on Corn Silage Yield and Quality"; J. Prod. Agic., vol. 11, No. 1, 1998.

Pendleton, J. et al., "Plant Population and Row Spacing Studies with brachytic 2 Dwarf Corn"; Contribution from the Department of Agronomy, Illinois Agr. Exp. Sta., Urbana, Ill; pp. 433-435, 1961.

Begna, S. H. et al., "Effects of Population Density and Planting Pattern on the Yield and Yield Components of Leafy Reduced-Stature Maize in a Short-Season Area"; J. Agronomy & Crop Science 179, pp. 9-17; 1997.

Cox, W. et al., "Corn Silage and Grain Yield Responses to Plant Densities"; J. Prod. Agric., vol. 10, No. 3, pp. 405-410, 1997.

International Search Report and Written Opinion regarding International App. No. PCT/US23/62985, mailed Jul. 27, 2023.

U.S. Appl. No. 19/337,629, filed Sep. 23, 2025, Cannon et al.

U.S. Appl. No. 19/367,230, filed Oct. 23, 2025, Barten et al.

* cited by examiner

FIG. 1

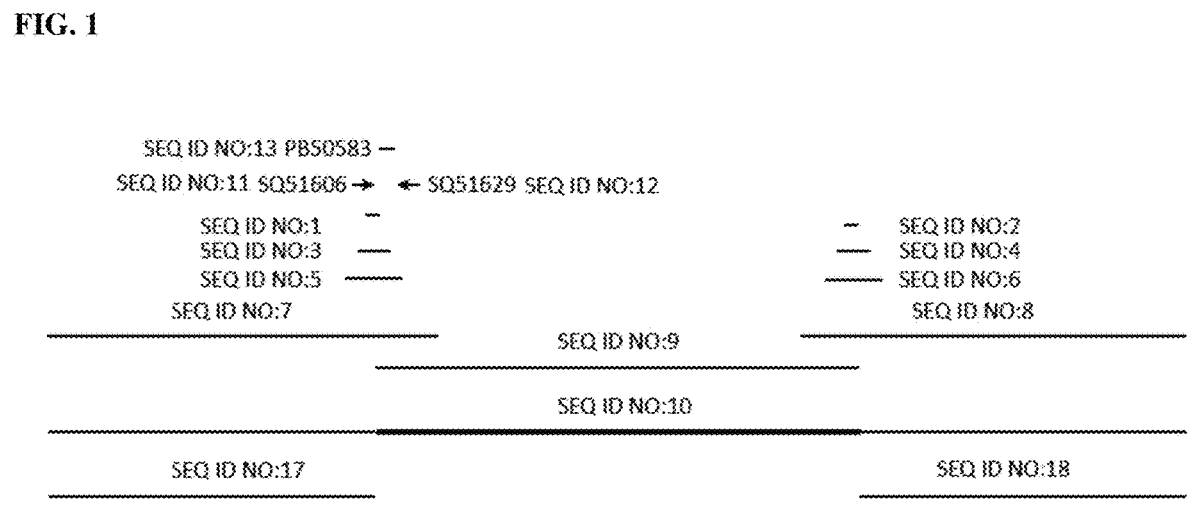

SEQ ID NO:13 PB50583 —

SEQ ID NO:11 SQ51606 →     ← SQ51629 SEQ ID NO:12

SEQ ID NO:1     —        —     SEQ ID NO:2

SEQ ID NO:3     ——        ——     SEQ ID NO:4

SEQ ID NO:5     ———        ———     SEQ ID NO:6

SEQ ID NO:7                            SEQ ID NO:8

SEQ ID NO:9

SEQ ID NO:10

SEQ ID NO:17                           SEQ ID NO:18

TRANSGENIC CORN EVENT ZM_BCS216090 AND METHODS FOR DETECTION AND USES THEREOF

CROSS-REFERENCE TO RELATED APPLICATIONS

This application claims the benefit of U.S. Provisional Appl. Ser. No. 63/274,865, filed Nov. 2, 2021, and U.S. Provisional Appl. Ser. No. 63/279,508, filed Nov. 15, 2021, both of which are incorporated herein by reference in their entirety.

INCORPORATION OF SEQUENCE LISTING

The sequence listing contained in the file named "MONS510US_ST26.xml" is 37.0 kilobytes (measured in Microsoft Windows®), was created on Oct. 7, 2022, is filed herewith by electronic submission, and is incorporated by reference

FIELD OF THE INVENTION

The present invention relates to recombinant DNA molecules present in and/or isolated from corn event ZM_BCS216090. The invention also relates to transgenic corn plants, plant parts, and seeds, cells, and agricultural products containing corn event ZM_BCS216090, as well as methods of using the same and detecting the presence of corn event ZM_BCS216090.

BACKGROUND

Corn (*Zea mays*) is an important crop and is a primary food source in many areas of the world. The methods of biotechnology have been applied to corn for improvement of the agronomic traits and quality of the product. Improved agronomic traits can include increased yield potential and stress tolerance such as increased lodging resistance, which may be accomplished through the expression of a transgene inserted into the genome of the corn plant.

The expression of transgenes in a transgenic plant, plant part, seed or cell, and thus their effectiveness, may be influenced by many different factors, such as the regulatory elements used in the transgene cassette, the chromosomal location of the transgene insertion site, the chromatin structure of the genome at or near the transgene insertion site, and the presence or proximity of any endogenous cis and/or trans regulatory elements or genes close to the transgene insertion site. These differences may result in variation in the level of transgene expression or in the spatial or temporal pattern of transgene expression between different transgenic insertion events of the same expression cassette. Different transgenic events may also have different levels or patterns of transgene expression in different plant germplasms and growth conditions and across different plant tissues and developmental stages. In addition, transformation events can also vary in terms of the molecular quality of the event. For example, a transgenic insertion event may be truncated relative to the intended insertion or contain additional vector backbone sequences. There may also be undesirable phenotypic or agronomic differences between some events. Since *Agrobacterium*-mediated transformation with a T-DNA construct containing a transgene expression cassette is largely variable and random in terms of where the transgene can be inserted into the plant genome, a variety of different transgenic events can be generated with unique chromosomal insertion sites.

For these reasons, the performance of different transformation events from the same transformation vector construct can vary, and the identification of transformation events conferring the most beneficial traits or characteristics without other potential off-types or concerns is needed to select a superior event for commercial use. Therefore, a number of individual plant transformation events must be produced and analyzed to select an event having superior commercial properties, which can be a significant undertaking that involves analysis and selection among many different transformation events.

SUMMARY

In one aspect, a recombinant DNA molecule is provided herein comprising a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, or a complete complement thereof. In particular embodiments, the recombinant DNA molecule is from corn event ZM_BCS216090, a representative sample of seed comprising the event having been deposited under ATCC Accession No. PTA-127050. In a further embodiment, recombinant DNA molecule is comprised in a corn plant, plant cell, seed, progeny plant, plant part, or commodity product. In other embodiments, the recombinant DNA molecule is formed by the insertion of a heterologous nucleic acid molecule into the genomic DNA of a corn plant or corn cell. In still further embodiments, the recombinant DNA molecule comprises an amplicon diagnostic for the presence of DNA derived from corn event ZM_BCS216090. In still yet another embodiment, the recombinant DNA molecule is derived from a transgenic corn plant comprising corn event ZM_BCS216090, a representative sample of seed comprising the event having been deposited under ATCC Accession No. PTA-127050.

In another aspect, a DNA molecule is provided herein comprising a polynucleotide segment of sufficient length to function as a DNA probe that hybridizes specifically under stringent hybridization conditions with corn event ZM_BCS216090 DNA in a sample, wherein detecting hybridization of the DNA molecule under the stringent hybridization conditions is diagnostic for the presence of corn event ZM_BCS216090 DNA in the sample. In particular embodiments, the DNA molecule comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, or a complete complement thereof. In other embodiments, the sample is derived from a corn plant, corn plant cell, corn seed, corn plant part, corn progeny plant, processed corn seed, animal feed comprising corn, corn oil, corn meal, corn flour, corn flakes, corn bran, pasta made with corn, corn biomass, and fuel products produced using corn and corn parts.

In yet another aspect, a pair of DNA molecules is provided herein comprising a first DNA molecule and a second DNA molecule different from the first DNA molecule, that function as DNA primers when used together in an amplification reaction with a sample containing corn event ZM_BCS216090 template DNA to produce an amplicon diagnostic for the presence of the corn event ZM_BCS216090 DNA in the sample, wherein the amplicon comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

In still yet another aspect, a method of detecting the presence of a DNA segment diagnostic for corn event ZM_BCS216090 DNA in a sample is provided herein, the method comprising: a) contacting the sample with a DNA molecule described herein; b) subjecting the sample and the DNA molecule to stringent hybridization conditions; and c) detecting hybridization of the DNA molecule to the DNA in the sample, wherein the detection is diagnostic for the presence of the corn event ZM_BCS216090 DNA in the sample.

In still yet another aspect, a method of detecting the presence of a DNA segment diagnostic for corn event ZM_BCS216090 DNA in a sample is provided herein, the method comprising: a) contacting the sample with the pair of DNA molecules provided herein; b) performing an amplification reaction sufficient to produce a DNA amplicon; and c) detecting the presence of the DNA amplicon in the reaction, wherein the DNA amplicon comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, or a complete complement thereof.

In still yet another aspect, a method of detecting the presence of a DNA segment diagnostic for corn event ZM_BCS216090 DNA in a sample is provided, the method comprising: a) contacting the sample with a DNA molecule comprising a nucleotide sequence that hybridizes specifically under stringent hybridization conditions with (i) corn event ZM_BCS216090 DNA; (ii) a DNA molecule comprising a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, or a complete complement thereof; or (iii) a DNA molecule comprising a polynucleotide segment of sufficient length to function as a DNA probe that hybridizes specifically under stringent hybridization conditions with corn event ZM_BCS216090 DNA in a sample; and b) performing a sequencing reaction to produce a target sequence, wherein the target sequence comprises a nucleotide sequence, or a portion or fragment of a nucleotide sequence, selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, or a complete complement thereof.

In still yet another aspect, provided herein is a corn plant, corn plant part, corn seed, or corn cell comprising: (a) a recombinant DNA molecule of the invention; or (b) a DNA segment comprising a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, or a complete complement thereof. In particular embodiments, the corn plant, corn plant part, corn seed, or corn cell exhibits reduced expression of at least a first endogenous gibberellin 20-oxidase (GA20ox) gene. In further embodiments, the gibberellin 20-oxidase (GA20ox) gene is selected from the group consisting of gibberellin 20-oxidase 3 (GA20ox3) and gibberellin 20-oxidase 5 (GA20ox5). In particular embodiments, the corn plant, corn plant part, corn seed, or corn cell has reduced expression of an endogenous gibberellin 20-oxidase 3 (GA20ox3) gene and an endogenous gibberellin 20-oxidase 5 (GA20ox5) gene. In still other embodiments, the corn plant, corn plant part, corn seed, or corn cell comprises corn event ZM_BCS216090, a representative sample of seed comprising the event having been deposited under ATCC Accession No. PTA-127050. In still yet another embodiment, the corn plant, corn plant part, corn seed, or corn cell may be further defined as a progeny plant of any generation of a corn plant comprising corn event ZM_BCS216090, or a corn plant part, corn seed, or corn cell derived therefrom.

In still yet another aspect, provided herein is a corn plant, corn plant part, corn seed, or corn cell that comprises corn event ZM_BCS216090, a representative sample of seed comprising the event having been deposited under ATCC Accession No. PTA-127050. In particular embodiments, a corn plant provided herein has a reduced plant height relative to a control corn plant. In other embodiments, a corn plant described herein has an increased lodging resistance relative to a control corn plant. In further embodiments, the corn plant, corn plant part, corn seed, or corn cell described herein comprises (a) a recombinant DNA molecule of the invention; or (b) a DNA segment comprising a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, or a complete complement thereof, wherein the nucleotide sequence is present in chromosome 1 of the corn plant, corn plant part, corn seed, or corn cell.

In still yet another aspect, provided herein is a DNA detection kit comprising: (a) a pair of DNA molecules, comprising a first DNA molecule and a second DNA molecule different from the first DNA molecule, that function as DNA primers when used together in an amplification reaction with a sample containing corn event ZM_BCS216090 template DNA to produce an amplicon diagnostic for the presence of the corn event ZM_BCS216090 DNA in the sample, wherein the amplicon comprises the nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10; and (b) a DNA probe comprising a polynucleotide segment of sufficient length to function as a DNA probe that hybridizes specifically under stringent hybridization conditions with corn event ZM_BCS216090 DNA in a sample, wherein detecting hybridization of the DNA molecule under the stringent hybridization conditions is diagnostic for the presence of corn event ZM_BCS216090 DNA in the sample.

In still yet another aspect, a method of producing a progeny corn plant comprising corn event ZM_BCS216090 is provided comprising: a) sexually crossing a first corn plant that comprises corn event ZM_BCS216090 with itself or a second corn plant; b) collecting one or more seeds produced from the cross; c) growing the seed to produce one or more progeny plants; and d) selecting at least a first progeny plant or seed comprising corn event ZM_BCS216090. In some embodiments, the at least a first progeny plant of the method has a reduced plant height and/or increased lodging resistance relative to a control corn plant. In particular embodiments, the method further comprises e) collecting seed from the at least first progeny plant comprising corn event ZM_BCS216090.

In still yet another aspect, provided herein is a hybrid corn plant or seed comprising corn event ZM_BCS216090 produced by a method according to the invention.

In still yet another aspect, provided herein is a corn seed comprising a detectable amount of a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, or a complete complement thereof.

In still yet another aspect, provided herein is a nonliving corn plant material comprising a detectable amount of a recombinant DNA molecule according to the invention.

In still yet another aspect, a microorganism is provided comprising a recombinant DNA molecule according to the invention. In particular embodiments, the microorganism is a plant cell.

In still yet another aspect, provided herein is a commodity product comprising a recombinant DNA molecule according to the invention. In particular embodiments, the commodity product is produced from a transgenic corn plant, corn plant part, corn seed, or corn cell comprising corn event ZM_BCS216090. In other embodiments, the commodity product is further selected from the group consisting of whole or processed corn seed, animal feed comprising corn, corn oil, corn meal, corn flour, corn flakes, corn bran, corn biomass, and fuel products produced using corn and corn parts.

In still yet another aspect, provided herein is a method of producing a commodity product, the method comprising: (a) obtaining a transgenic corn plant, corn plant part, or corn seed comprising corn event ZM_BCS216090; and (b) producing a commodity product from the transgenic corn plant, corn plant part, or corn seed.

In still yet another aspect, a corn plant, corn plant part, or corn seed is provided comprising a DNA molecule functional as a template when tested in a DNA amplification method producing an amplicon diagnostic for the presence of corn event ZM_BCS216090 DNA.

In still yet another aspect, a method is provided for determining the zygosity of a corn plant, corn plant part, or corn seed comprising corn event ZM_BCS216090 comprising: a) contacting a sample comprising DNA from the corn plant, corn plant part, or corn seed with a set of primer pairs comprising at least two different primer pairs capable of producing a first amplicon diagnostic for corn event ZM_BCS216090 and a second amplicon diagnostic for native corn genomic DNA not comprising corn event ZM_BCS216090; b) performing a nucleic acid amplification reaction with the sample and the set of primer pairs; and c) detecting in the nucleic acid amplification reaction the first amplicon diagnostic for corn event ZM_BCS216090 and the second amplicon diagnostic for native corn genomic DNA not comprising corn event ZM_BCS216090, wherein the presence of only the first amplicon is diagnostic of a corn plant, corn plant part, or corn seed homozygous for corn event ZM_BCS216090, and the presence of both the first amplicon and the second amplicon is diagnostic of a corn plant, corn plant part, or corn seed heterozygous for corn event ZM_BCS216090.

In still yet another aspect, a method is provided for determining the zygosity of a corn plant, corn plant part, or corn seed comprising corn event ZM_BCS216090 comprising: a) contacting a sample comprising DNA from the corn plant, corn plant part, or corn seed with a first primer pair capable of producing a first amplicon of all or part of corn event ZM_BCS216090 and a second primer pair capable of producing a second amplicon of a standard genomic sequence known to be single copy and homozygous in the corn plant, corn plant part, or corn seed; b) contacting the sample with a first probe that specifically hybridizes to the first amplicon and/or all or part of corn event ZM_BCS216090, and a second probe that specifically hybridizes to the standard genomic sequence; c) performing a DNA amplification reaction using real-time PCR and determining the cycle thresholds (Ct values) of the first amplicon and the second amplicon; d) calculating the difference ($\Delta$Ct) between the Ct values of the second amplicon and the first amplicon; and e) determining the zygosity of corn event ZM_BCS216090, wherein a $\Delta$Ct of about zero (0) indicates homozygosity of corn event ZM_BCS216090 and a $\Delta$Ct of about one (1) indicates heterozygosity of corn event ZM_BCS216090. In particular embodiments of the methods described herein, the set of primer pairs comprises SEQ ID NO: 11 combined with SEQ ID NO: 12, and SEQ ID NO: 14 combined with SEQ ID NO: 15.

In still yet another aspect, a method is provided for determining the zygosity of a corn plant, corn plant part, or corn seed comprising corn event ZM_BCS216090 comprising: a) contacting a sample comprising DNA from the corn plant, corn plant part, or corn seed with a primer pair capable of producing a first amplicon diagnostic for corn event ZM_BCS216090 and a second amplicon diagnostic for native corn genomic DNA not comprising corn event ZM_BCS216090; b) performing a nucleic acid amplification reaction with the sample and the set of primer pairs; and c) detecting the first amplicon and the second amplicon, wherein the presence of only the first amplicon is diagnostic of a corn plant, corn plant part, or corn seed homozygous for corn event ZM_BCS216090, the presence of only the second amplicon is diagnostic of a corn plant, corn plant part, or corn seed homozygous for native corn genomic DNA not comprising corn event ZM_BCS216090, and the presence of both the first amplicon and the second amplicon is diagnostic of a corn plant, corn plant part, or corn seed heterozygous for corn event ZM_BCS216090.

In still yet another aspect, a method is provided for determining the zygosity of a corn plant, corn plant part, or corn seed comprising corn event ZM_BCS216090 comprising: (a) contacting a sample comprising DNA from the corn plant, corn plant part, or corn seed with a probe set which contains at least a first probe that specifically hybridizes to corn event ZM_BCS216090 and at least a second probe that specifically hybridizes to corn genomic DNA that was disrupted by insertion of the heterologous DNA of corn event ZM_BCS216090 and does not hybridize to corn event ZM_BCS216090 DNA; and (b) hybridizing the probe set with the sample under stringent hybridization conditions, wherein detecting hybridization of only the first probe under the hybridization conditions is diagnostic for a corn plant, corn plant part, or corn seed homozygous for corn event ZM_BCS216090, and wherein detecting hybridization of both the first probe and the second probe under the hybridization conditions is diagnostic for a corn plant, corn plant part, or corn seed heterozygous for corn event ZM_BCS216090. In particular embodiments, the probe set comprises SEQ ID NO:13 and SEQ ID NO:16.

In still yet another aspect, a method of producing a corn plant having reduced plant height or increased lodging resistance is provided comprising: introducing corn event ZM_BCS216090 into a corn plant, a representative sample of seed comprising the event having been deposited under ATCC Accession No. PTA-127050. Also provided herein is a population of transgenic corn plants produced according to a method of the invention, wherein each transgenic corn plant comprises corn event ZM_BCS216090. In particular embodiments, such a population of corn plants has a reduced plant height on average relative to a population of control corn plants lacking corn event ZM_BCS216090. In further embodiments, the population of corn plants has an increased lodging resistance on average relative to a population of control corn plants lacking corn event ZM_BCS216090.

The forgoing and other aspects of the disclosure will become more apparent from the following detailed description.

BRIEF DESCRIPTION OF THE DRAWINGS

FIG. 1 represents the sequence of corn event ZM_BCS216090. Horizontal lines and boxes correspond to the positions of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9, relative to SEQ ID NO: 10. The horizontal arrows labeled SQ51606 (SEQ ID NO: 11) and SQ51629 (SEQ ID NO: 12) represent the approximate position of a pair of primers that can be used to detect corn event ZM_BCS216090 and the horizontal line labeled PB50583 (SEQ ID NO: 13) represents the approximate position of a DNA probe that can be used to detect corn event ZM_BCS216090.

BRIEF DESCRIPTION OF THE SEQUENCES

Figure 2:
FIG. 2 shows the pM578 construct vector map used for *Agrobacterium*-mediated transformation of corn to produce transgenic events provided herein including ZM_BCS216090.
Figure 3:
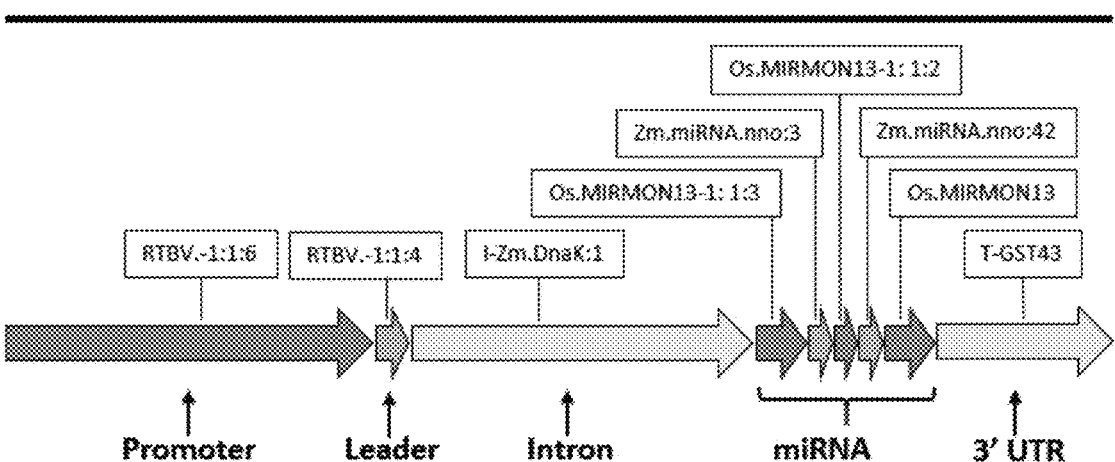
FIG. 3 represents the miRNA expression cassette of corn event ZM_BCS216090 relative to SEQ ID NO: 9 with their respective genetic elements labeled as described in Table 1.

SEQ ID NO: 1 is a 30 nucleotide sequence representing the 5' junction region of corn genomic DNA and the integrated transgenic expression cassette. SEQ ID NO: 1 is found within SEQ ID NO: 10 at nucleotide positions 986 to 1,015.

SEQ ID NO: 2 is a 30 nucleotide sequence representing the 3' junction region of the integrated transgenic expression cassette and the corn genomic DNA. SEQ ID NO: 2 is found within SEQ ID NO: 10 at nucleotide positions 3,719 to 3,748.

SEQ ID NO: 3 is a 60 nucleotide sequence representing the 5' junction region of corn genomic DNA and the integrated transgenic expression cassette. SEQ ID NO: 3 is found within SEQ ID NO: 10 at nucleotide positions 971 to 1,030.

SEQ ID NO: 4 is a 60 nucleotide sequence representing the 3' junction region of the integrated transgenic expression cassette and the corn genomic DNA. SEQ ID NO: 4 is found within SEQ ID NO: 10 at nucleotide positions 3,704 to 3,763.

SEQ ID NO: 5 is a 100 nucleotide sequence representing the 5' junction region of corn genomic DNA and the integrated transgenic expression cassette. SEQ ID NO: 5 is found within SEQ ID NO: 10 at nucleotide positions 951 to 1,050.

SEQ ID NO: 6 is a 100 nucleotide sequence representing the 3' junction region of the integrated transgenic expression cassette and the corn genomic DNA. SEQ ID NO: 6 is found within SEQ ID NO: 10 at nucleotide positions 3,684 to 3,783.

SEQ ID NO: 7 is a 1,180 nucleotide sequence representing 1000 nucleotides of 5' flanking corn genomic DNA and 180 nucleotides of the inserted T-DNA. SEQ ID NO: 7 is found within SEQ ID NO: 10 at nucleotide positions 1 to 1,180.

SEQ ID NO: 8 is a 1,107 nucleotide sequence representing 107 nucleotides of the inserted T-DNA and 1,000 nucleotides of 3' flanking corn genomic DNA after the inserted T-DNA. SEQ ID NO: 8 is found within SEQ ID NO: 10 at nucleotide positions 3,627 to 4,733.

SEQ ID NO: 9 is a 2,733 nucleotide sequence corresponding to the transgenic inserted T-DNA of corn event ZM_BCS216090. SEQ ID NO: 9 is found within SEQ ID NO: 10 at nucleotide positions 1,001 to 3,733.

SEQ ID NO: 10 is a 5,731 nucleotide sequence corresponding to the contig nucleotide sequence of the 5' genomic flanking DNA nucleotide sequence, the inserted T-DNA nucleotide sequence in event ZM_BCS216090, and the 3' genomic flanking DNA nucleotide sequence; and includes SEQ ID NO: 17 (nucleotides 1-1,000), SEQ ID NO: 9 (nucleotides 1,001 to 3,733), and SEQ ID NO: 18 (nucleotides 3,734 to 4,733).

SEQ ID NO: 11 is a 19 nucleotide sequence corresponding to a thermal amplification primer referred to as SQ51606 used to identify corn event ZM_BCS216090 DNA in a sample, and is identical to the nucleotide sequence corresponding to positions 982 to 1,000 of SEQ ID NO: 10.

SEQ ID NO: 12 is a 21 nucleotide sequence corresponding to a thermal amplification primer referred to as SQ51629 used to identify corn event ZM_BCS216090 DNA in a sample, and is identical to the reverse complement of the nucleotide sequence corresponding to positions 1,049 to 1,069 of SEQ ID NO: 10.

SEQ ID NO: 13 is a 19 nucleotide sequence corresponding to a probe referred to as PB50583 used to identify corn event ZM_BCS216090 DNA in a sample, and is identical to the reverse complement of the nucleotide sequence corresponding to positions 1,028 to 1,046 of SEQ ID NO: 10.

SEQ ID NO: 14 is a 24 nucleotide sequence corresponding to a thermal amplification primer referred to as SQ20222 used as an internal control for the event and zygosity assay for corn event ZM_BCS216090 and hybridizes to a region of the corn genome.

SEQ ID NO: 15 is a 28 nucleotide sequence correspond-ing to a thermal amplification primer referred to as SQ20221 used as an internal control for the event and zygosity assay for corn event ZM_BCS216090 and hybridizes to a region of the corn genome.

SEQ ID NO: 16 is a 17 nucleotide sequence correspond-ing to a probe referred to as PB50298 used as an internal control for the event and zygosity assay for corn event ZM_BCS216090 and hybridizes to a region of the corn genome.

SEQ ID NO: 17 is a 1,000 nucleotide sequence of the 5' flanking corn genomic DNA up to, but not including, the 5' junction. SEQ ID NO: 17 is found within SEQ ID NO: 10 at nucleotide positions 1 to 1,000.

SEQ ID NO: 18 is a 1,000 nucleotide sequence of the 3' flanking corn genomic DNA starting from, but not including, the 3' junction. SEQ ID NO: 18 is found within SEQ ID NO: 10 at nucleotide positions 3,734 to 4,733.

DETAILED DESCRIPTION

Plant height is an important agronomic trait in crops, as it can directly affect yield potential and lodging resistance. Manipulation of GA levels in semi-dwarf wheat, rice and sorghum plant varieties led to increased yield and reduced lodging in cereal crops during the $20^{th}$ century, which was largely responsible for the Green Revolution. Gibberellins (gibberellic acids or GAs) are plant hormones that regulate various plant growth and developmental processes, includ-ing stem elongation, germination, dormancy, flowering, flower development, and leaf and fruit senescence. Bioactive GAs in corn include $GA_1$, $GA_3$, $GA_4$, and $GA_7$. GA bio-synthesis is regulated by genes encoding GA20-oxidases (GA20ox) and GA3-oxidases (GA3ox) which catalyze steps in the synthesis of bioactive GAs, whereas GA catabolism is regulated by genes encoding GA2-oxidases (GA2ox) which reduce the level of active GAs. By manipulating genes in the GA biosynthesis or catabolism pathways, the level of active GAs can be lowered to reduce plant height.

The present disclosure provides a transgenic corn event, designated ZM_BCS216090, that comprises a transgene expression cassette that encodes a microRNA (miRNA) that suppresses the expression of the endogenous GA20ox3 and GA20ox5 genes in corn. The reduction in gibberellin levels caused by event ZM_BCS216090 results in a decreased internode length and overall decreased plant height, without any observable off-types. These short-stature corn or maize plants comprising the ZM_BCS216090 event are less sus-ceptible to crop loss due to lodging and green snap. Corn or maize plants comprising the ZM_BCS216090 event there-fore provide corn growers with a new option for increasing yield potential and reducing crop losses due to lodging or green snap especially when confronted with adverse or extreme weather or wind events.

Plant transformation techniques, such as *Agrobacterium* mediated or particle bombardment transformation, can be used to insert foreign DNA (also known as transgenic DNA) randomly into a chromosome of the genome of a plant cell to produce a genetically engineered plant cell, also referred to as a "transgenic" or "recombinant" cell. Using these non-targeted transformation techniques, many individual cells can be transformed, each resulting in a unique "trans-genic event" or "event" due to the random (or largely random) insertion of the foreign DNA into the genome. A transgenic plant can then be regenerated from each indi-vidual transgenic cell. This results in every cell of the transgenic plant containing the uniquely inserted transgenic event as a stable part of its genome. The transgenic plant can then be used to produce progeny plants, each containing the unique transgenic event. The term "transgenic" refers to a plant, plant part, plant cell, plant tissue, or DNA molecule, construct or sequence, as the case may be, comprising a transgene—e.g., a "transgenic cell" refers to a cell compris-ing a transgene.

Corn event ZM_BCS216090 was produced by an *Agro-bacterium*-mediated transformation process of corn imma-ture embryos with a single T-DNA binary system. In this system, an *Agrobacterium* strain employing one binary plasmid vector with a single T-DNA was utilized. The T-DNA construct comprised a transgene cassette for the expression of a microRNA (miRNA) that suppresses the expression of the endogenous gibberellin oxidase genes GA20ox3 and GA20ox5, and a transgene cassette used for the selection of transformed corn cells using glyphosate selection (CP4). The glyphosate selection cassette was flanked on both sides with LoxP recognition sites which are recognized by Cre-recombinase, derived from Enterobacte-ria phage P1 (Gilbertson, *TRENDS in Biotechnology*, 21(12):550-555, 2003).

As specifically described herein, corn event ZM_BCS216090 was produced by a complex research and development process in which: (1) a DNA construct and vector comprising two expression cassettes as identified above within a T-DNA region bounded by left and right border sequences was designed and selected based on indi-vidual testing of each expression cassette as well as in combination; (2) thousands of corn cells were transformed with the construct used to generate event ZM_BCS216090 and other events, creating a population of transgenic plants in which each plant contained a unique transgenic event that was regenerated; (3) more than a hundred transgenic plants were advanced through a series of self and out-crosses for further testing and event selection after excluding many events based on molecular quality screening and gold stan-dard seed and product development; (4) the glyphosate selection cassette in corn event ZM_BCS216090 was removed through in vivo Cre-excision to create a "marker-free" events; and (5) the final lead event ZM_BCS216090 was selected from many different events after a rigorous multi-year event selection process involving testing and analysis of their molecular and genomic characteristics, efficacy and performance data, breeding and trait consider-ations, and agronomic properties in a variety of genetic backgrounds for each event that was advanced for testing. Corn event ZM_BCS216090 was produced and selected as a uniquely superior event, useful for broad-scale agronomic purposes.

The T-DNA from the transformation plasmid vector and inserted into the genome of corn event ZM_BCS216090 was characterized by detailed molecular analysis. This analysis included: the insert number (number of integration sites within the corn genome), the genomic insert location (the specific site in the corn genome where the insertion occurred), the copy number (the number of copies of the T-DNA within one locus), and the integrity of the inserted transgenic DNA. The detailed molecular analysis demon-strated that the integrated T-DNA containing the transgenic miRNA cassette remained intact after integration and Cre-excision of the glyphosate (CP4) EPSPS selection cassette. As used herein, an "expression cassette" or "cassette" or "transgene" is a recombinant DNA molecule or sequence comprising a combination of distinct elements that can express a RNA and/or protein encoded by a coding sequence of the transgene in a transformed plant cell comprising the transgene. As provided herein, an "expression cassette" or "cassette" or "transgene" includes one or more regulatory element(s) operably linked to the coding or transcribable DNA sequence for the miRNA including the promoter, leader, intron and terminator sequences. The "expression cassette" or "cassette" or "transgene" is recombinant and heterologous with respect to the transformed plant cell genome. For purposes of the present disclosure, such an "expression cassette" or "cassette" or "transgene" is a recombinant DNA molecule or sequence that encodes a miRNA as described herein. Table 1 provides a list of the elements contained in SEQ ID NO: 10 after Cre excision of the CP4 cassette, the DNA sequence that corresponds to corn event ZM_BCS216090.

sequence in relation to a corn cell, corn tissue, corn seed, corn plant, corn plant part and/or corn plant product, such as a corn commodity product, means that the DNA molecule, amplicon or sequence is taken, purified, isolated, or made, directly or indirectly, from such corn cell, corn tissue, corn seed, corn plant, corn plant part and/or corn plant product, such as a corn commodity product, as the case may be. Alternatively, the term "derived" or "derived from" in reference to a corn plant product, such as a corn commodity product, in relation to a corn cell, corn tissue, corn seed, corn plant, and/or corn plant part, means that the corn plant product is taken, purified, isolated, or made, directly or indirectly, from such corn cell, corn tissue, corn seed, corn plant, and/or corn plant part, as the case may be. "Capable

TABLE 1

| | Description of corn event ZM_BCS216090. | |
| --- | --- | --- |
| Element | Position in SEQ ID NO: 10 | Description |
| 5' Flanking DNA | 1-1,000 | DNA sequence flanking the 5' end of the transgenic insert |
| Left Border Region | 1,001-1,040 | DNA region from *Agrobacterium tumefaciens* containing the left border sequence |
| Intervening Sequence | 1,041-1,296 | Sequence used in DNA cloning |
| RTBV.–1:1:6 | 1,297-2,023 | Promoter sequence from Rice tungro bacilliform virus |
| RTBV.–1:1:4 | 2,024-2,062 | Leader sequence from Rice tungro bacilliform virus |
| Intervening Sequence | 2,063-2,082 | Sequence used in DNA cloning |
| I-Zm.DnaK:1 | 2,083-2,886 | Intron sequence of a heat shock gene from maize (*Zea mays*) |
| Os.MIRMON13-1: 1:3 | 2,887-2,998 | Backbone sequence of a miRNA gene from rice (*Oryza sativa*) |
| Zm.miRNA.nno:3 | 2,999-3,019 | Transgenic miRNA sequence |
| Os.MIRMON13-1: 1:2 | 3,020-3,053 | Loop sequence of the miRNA gene from rice (*Oryza sativa*) |
| Zm.miRNA.nno:42 | 3,054-3,074 | Transgenic miRNA* sequence |
| Os.MIRMON13 | 3,075-3,294 | Backbone sequence of the miRNA from rice (*Oryza sativa*) |
| Intervening Sequence | 3,295-3,326 | Sequence used in DNA cloning |
| T-GST43 | 3,327-3,626 | 3' UTR sequence |
| Intervening Sequence | 3,627-3,733 | Sequence used in DNA cloning |
| 3' Flanking Sequence | 3,734-4,733 | DNA sequence flanking the 3' end of the transgenic insert |

Corn event ZM_BCS216090 is characterized as an insertion into a single locus in the corn genome, resulting in two new loci or junction sequences (e.g., sequences set forth in SEQ ID NO: 1, SEQ ID NO: 2, SEQ ID NO: 3, SEQ ID NO: 4, SEQ ID NO: 5, and SEQ ID NO: 6) spanning a portion of the inserted DNA and the corn genomic DNA that are not known to appear or exist naturally in the corn genome or other transgenic corn events—they are unique to event ZM_BCS216090. SEQ ID NO: 1, SEQ ID NO: 2, and SEQ ID NO: 3 span one of the junctions, and SEQ ID NO: 4, SEQ ID NO: 5, and SEQ ID NO: 6 span the other junction. These junction sequences are useful in detecting the presence of the event ZM_BCS216090 in corn cells, corn tissue, corn seed, and corn plants or corn plant products, such as corn commodity products. Polynucleotide or DNA molecular probes and/or primer pairs are described herein that have been, or could be, developed for use in identifying the presence of these various junction segments in biological samples containing or derived from, or suspected of containing or being derived from, corn cells, corn seed, corn plant parts, corn plants, or corn plant tissue that contain the event ZM_BCS216090.

As used herein, the term "derived" or "derived from" in reference to a particular DNA molecule, amplicon or of being detected" refers to the ability of a particular DNA molecule, segment or sequence to be detected in a sample, such as by amplification and determining its presence, size or sequence such as by DNA sequence analysis, and/or binding of a probe to the target DNA molecule, segment or sequence.

A "sample" is intended to refer to any composition comprising or derived from, either directly or indirectly, a biological sample, source or material. The sample may generally comprise corn DNA and/or substantially or completely pure, purified or isolated corn DNA. A "biological sample" contains biological materials, including but not limited to DNA obtained or derived from, either directly or indirectly, the genome of a corn cell(s), corn tissue(s), corn seed(s), corn plant(s), corn plant part(s) and/or corn plant product(s), such as a corn commodity product(s). Such corn cell(s), corn tissue(s), corn seed(s), corn plant(s), corn plant part(s) and/or corn plant product(s), such as a corn commodity product(s), may comprise corn event ZM_BCS216090 or DNA molecule(s) and/or DNA segment(s) comprising corn event ZM_BCS216090. In some embodiments, a sample or biological sample may comprise corn cell(s), corn tissue(s), corn seed(s), corn plant(s), corn plant part(s), and/or corn plant product(s), whose cells or cellular membranes have been fractured (e.g., disrupted or opened) to release the contents of the corn cell(s) including genomic DNA and/or make the contents of the corn cell(s) including genomic DNA accessible or usable for assays or testing. "Directly" refers to directly obtaining DNA by a skilled artisan from the corn genome by fracturing corn cells (or by obtaining samples of corn that contain fractured corn cells) and exposing or using the genomic DNA from corn cells for the purposes of detection. "Indirectly" refers to obtaining by a skilled artisan a target or specific reference DNA (i.e., a novel and unique junction segment(s) described herein as being diagnostic for the presence of the event ZM_BCS216090) in a particular sample, by means other than by obtaining directly via fracturing of corn cells or obtaining a sample of corn that contains fractured corn cells. Such indirect means include, but are not limited to, amplification of a DNA segment that contains a DNA sequence targeted by a particular probe(s) and/or primer set(s) designed to bind with specificity to or near the target sequence, or amplification of a DNA segment comprising all or part of a target sequence that can be measured and characterized (e.g., measured by migration or separation from other segments of DNA and/or identification in an effective matrix, such as an agarose or acrylamide gel or the like, or characterized by direct sequence analysis of the amplicon(s), or cloning of the amplicon(s) into a vector(s) and direct sequencing of the inserted amplicon(s) present within such vector(s)).

Detailed molecular analysis demonstrated that event ZM_BCS216090 contains a single T-DNA insertion with one copy of the SD419 transgenic miRNA expression cassette. No additional elements from the transformation construct other than portions of the *Agrobacterium tumefaciens* left border region used for transgenic DNA transfer from the plant transformation plasmid to the corn genome were identified in event ZM_BCS216090. Finally, thermal amplification producing specific amplicons diagnostic for the presence of event ZM_BCS216090 in a sample and DNA sequence analyses were performed to determine the assigned 5' and 3' insert-to-plant genome junctions, confirm the organization of the elements within the insert, and determine the complete DNA sequence of the inserted transgenic DNA (SEQ ID NO: 9). SEQ ID NO: 7 is a sequence corresponding to the 5' corn genomic DNA sequence of SEQ ID NO: 10 and a portion of the inserted T-DNA sequence presented as SEQ ID NO: 9. SEQ ID NO: 8 is a sequence corresponding to the 3' corn genomic DNA sequence of SEQ ID NO: 10 and a portion of the inserted T-DNA sequence presented as SEQ ID NO: 9. SEQ ID NO: 10 corresponds to corn event ZM_BCS216090 and contains a contiguous sequence (contig) comprising the 5' corn genomic flanking sequence, the transgene insert of event ZM_BCS216090, and the 3' corn genomic flanking sequence, and thus contains the 5' and 3' insert-to-plant genome junction sequences. As used herein, the 5' and 3' designations in reference to the junction, direction and side of the transgenic event insertion is relative to the 5' to 3' direction of the transgene, with the 5' junction and genomic sequence being upstream of the transgene, and the 3' junction and genomic sequence being downstream of the transgene.

Unless otherwise noted herein, terms are to be understood according to conventional usage by those of ordinary skill in the relevant art. Definitions of common terms in molecular biology may be found in Rieger et al., Glossary of Genetics: Classical and Molecular, 5*th* edition, Springer-Verlag: New York, 1991; and Lewin, Genes V, Oxford University Press:

New York, 1994, along with other sources known to those skilled in the relevant art. As used herein, the term "corn" or "maize" means plant species within *Zea mays* and all plant varieties belonging to the genus *Zea* that can be bred with *Zea mays* plants, including wild maize species.

The present disclosure provides for transgenic corn or maize plants which have been transformed with a DNA construct that contains an expression cassette encoding a transgenic miRNA to suppress expression of endogenous GA20 oxidase target genes. The terms "suppress" and "suppression" as used herein, refer to a lowering, reduction, or elimination of the expression level of a mRNA and/or protein encoded by a target gene in a plant, plant cell, or plant tissue at one or more stage(s) of plant development, as compared to the expression level of such target gene mRNA and/or protein in a wild-type or control plant, cell, or tissue at the same stage(s) of plant development. Corn plants transformed according to the methods and with the DNA construct disclosed herein have a short stature (shorter plant height) phenotype.

A transgenic plant is produced by transformation of a plant cell with a recombinant DNA construct that includes the expression cassette and transgene encoding the miRNA as described herein. Such recombinant DNA construct is also heterologous with respect to the plant cell, regeneration of at least one plant from the plant cell comprising an insertion of the transgene into the genome of the plant cell, and selection of a particular plant characterized by insertion of the transgene into a particular genomic location of the plant based on a number of efficacious and quality characteristics and features of the event and regenerated transgenic plant and progeny as described further herein. The term "transgenic event" or "event" refers to the inserted transgenic DNA in the plant genome and flanking genomic sequences immediately adjacent to the inserted transgenic DNA in the genome of the transformed plant, but also refers to a DNA molecule comprising the inserted transgenic DNA in the plant genome and flanking genomic sequences. Each event is unique and would be expected to be transferred to progeny plants that receive the transgenic DNA and event through genetic inheritance and/or segregation from a parent as the result of a sexual or self-cross of a first parental line that includes the inserted transgenic DNA and event either with itself or a second parental line that may or may not contain the same transgenic DNA and event. The parental line that includes the inserted transgenic DNA and event may itself be the original transformant or a progeny plant of said original transformant that may have been generated by "selfing" the transformant with itself or crossing the transformant or a progeny plant of the transformant that includes the inserted transgenic DNA and event with another plant. For purposes of the present disclosure, the "event" refers to corn event ZM_BCS216090.

As used herein, the term "flanking" in reference to a transgenic event refers to the plant genomic sequence(s) immediately adjacent to the transgenic DNA insertion in the genome of a transformed plant, plant part, plant tissue, or plant cell comprising the transgenic event on the 5' and/or 3' side(s) or end(s) of the transgenic event insertion. Likewise, "flanking DNA" refers to a length of genomic DNA sequence immediately adjacent to the transgenic DNA insertion in the genome of the transformed plant on the 5' and/or 3' side(s) or end(s) of the insertion.

The present disclosure provides the original transformant plant and progeny of the transformant that include the transgenic DNA and event. Such progeny may be produced by a sexual cross or outcross between plants comprising the same transgenic DNA and event, or between a plant comprising the transgenic DNA and event with another plant, or by any other method known in the art including any cell or tissue culture method, wherein the progeny includes the transgenic DNA and event. Such other plant may be a transgenic plant comprising the same and/or a different transgene or may be a non-transgenic plant, and each parental plant in a cross or outcross may be the same or different germplasm or breeding line. Even after repeated back-crossing to a recurrent parent, the transgenic DNA and event is present in progeny of the cross at the same chromosomal location. Thus, a "transgenic plant" can be the original transformant plant regenerated from the transformed plant cell and comprising the transgenic DNA and event, or a progeny plant of the original transformant plant, which may be separated from the transformant by one or more generations, that retains the transgenic DNA and event at the same specific location and sequence context in the plant's genome. The transformant or progeny plant may be homozygous or heterozygous for event ZM_BCS216090. In addition, a "transgenic plant" can include a plant produced from a transformed plant cell or tissue, or from another transgenic plant or plant part, by or using cell or tissue culture methods known in the art. A "transgenic plant" may comprise a plant having a transgene stably inserted into the genome of at least one cell of the plant (i.e., corn event ZM_BCS216090 in at least one cell of the plant), and the plant may be chimeric or non-chimeric with respect to the transgene and/or event. A transgenic plant is chimeric with respect to a transgene if not all cells of the plant comprise the transgene.

As used herein, the term "recombinant" refers to a non-natural DNA, protein, or combination that would not normally be found in nature, such as a combination of DNA sequences, proteins that would not naturally occur together, and is the result of human intervention. A "recombinant DNA molecule" is a DNA molecule comprising a combination of DNA sequences that would not naturally occur together and is the result of human intervention. Two or more elements of such combination of DNA sequences may be operably linked to one another. For example, a recombinant DNA molecule may comprise a combination of at least two DNA sequences that are heterologous with respect to each other, such as a DNA molecule that comprises a coding or transcribable DNA sequence operably linked to a heterologous promoter and/or other regulatory expression element(s), and/or a plant genomic DNA sequence comprising all or part of a transgene and a heterologous and flanking genomic sequence(s) adjacent to the transgene, and/or a DNA molecule that is artificially synthesized and comprises a polynucleotide sequence that deviates from any polynucleotide sequence that would normally exist in nature. A recombinant DNA molecule may comprise all or part of a junction sequence of the genome of a plant and all or part of the transgene insertion into the genome of the plant, and/or may comprise a recombinant or heterologous DNA fragment of event ZM_BCS216090. An example of a recombinant DNA molecule is a DNA molecule comprising at least one of SEQ ID NOs: 1-10. As used herein, a recombinant plant, plant part, plant cell or plant tissue is a plant, plant part, plant cell or plant tissue that would not normally exist in nature, is the result of human intervention, and contains a transgene incorporated into the genome of the plant, plant part, plant cell or plant tissue. As a result of such genomic insertion, the recombinant plant is something new and distinctly different from any related wild-type or naturally occurring plant, plant part, plant cell or plant tissue. An example of a recombinant plant, plant part, plant cell or plant tissue is a corn or maize plant, plant part, plant cell or plant tissue containing the event ZM_BCS216090.

As used herein, the term "heterologous" in reference to a combination of two or more DNA sequences or elements means that the two or more DNA sequences or elements do not normally exist together as such combination in nature without human intervention. As used herein, the term "heterologous" in reference to a DNA molecule, construct or sequence in relation to a plant, microorganism, plant cell or plant genome means that the DNA molecule, construct or sequence does not exist in nature as part of such plant, microorganism, plant cell or plant genome, and/or does not exist in the same physical or genomic location, context or orientation as part of such plant, microorganism, plant cell or plant genome in nature, without human intervention.

The present disclosure provides DNA molecules and fragments and their corresponding DNA sequences. The terms "DNA" and "DNA molecule" as used herein refer to a deoxyribonucleic acid (DNA) molecule. A DNA molecule may be of genomic or synthetic origin and/or comprise a recombinant or heterologous DNA molecule or sequence. A DNA molecule may be described in reference to its 5' (upstream) end and 3' (downstream) end. As used herein, the term "DNA sequence" refers to the polynucleotide sequence of the DNA molecule—i.e., the sequence of consecutive nucleotides in the DNA molecule. As used herein in reference to nucleotides of a polynucleotide or DNA sequence or molecule, the terms "consecutive" and "contiguous" are interchangeable and synonymous and refer to the 5' to 3' order of nucleotides in a polynucleotide or DNA sequence, strand or molecule without any gap or interruption between them. By convention, DNA sequences of the disclosure and fragments thereof are disclosed with reference to the 5' to 3' direction of only one strand of the two, anti-parallel and complementary DNA strands of a DNA molecule. By implication and intent, the complementary sequences of the sequences provided here (i.e., the sequences of the complementary, opposing, or antiparallel strand), also referred to in the art as the reverse complementary or reverse complement sequences, are within the scope of the present disclosure and are expressly intended to be within the potential scope of the subject matter as claimed. A DNA molecule, or a fragment derived therefrom, can also be extracted from plant part(s), plant cell(s) and/or tissue(s) or a homogenate, extract or lysate from plant part(s), plant cell(s) and/or tissue(s), or can be produced as an amplicon from extracted, purified or isolated DNA from plant part(s), plant cell(s) and/or tissue(s), or a homogenate, extract or lysate from plant part(s), plant cell(s) and/or tissue(s), which may further comprise event ZM_BCS216090.

As used herein, the term "fragment" refers to a smaller piece or sequence of a larger or whole DNA molecule or sequence. For example, a fragment of SEQ ID NO: 9 or 10 may include a sequence that is at least about 12 consecutive nucleotides, at least about 13 consecutive nucleotides, at least about 14 consecutive nucleotides, at least about 15 consecutive nucleotides, at least about 16 consecutive nucleotides, at least about 17 consecutive nucleotides, at least about 18 consecutive nucleotides, at least about 19 consecutive nucleotides, at least about 20 consecutive nucleotides, at least about 21 consecutive nucleotides, at least about 22 consecutive nucleotides, at least about 23 consecutive nucleotides, at least about 24 consecutive nucleotides, at least about 25 consecutive nucleotides, at least about 30 consecutive nucleotides, at least about 35 consecutive nucleotides, at least about 40 consecutive nucleotides, at least about 45 consecutive nucleotides, at least about 50 consecutive nucleotides, at least about 60 consecutive nucleotides, at least about 70 consecutive nucleotides, at least about 80 consecutive nucleotides, at least about 90 consecutive nucleotides, at least about 100 consecutive nucleotides, at least about 200 consecutive nucleotides, at least about 300 consecutive nucleotides, at least about 400 consecutive nucleotides, or at least about 500 consecutive nucleotides of the larger, whole or complete DNA molecule or sequence of SEQ ID NO: 9 or 10.

As used herein, the term "isolated" in reference to a molecule means that the molecule is at least partially separated from other molecules or sequences that are normally associated with the molecule in its native or natural state. In some embodiments, the term "isolated" refers to a DNA molecule that is at least partially separated from the nucleic acids or polynucleotide or DNA sequence(s) that normally flank and are covalently linked to the sequence of the DNA molecule in its native or natural state. An "isolated" DNA molecule may have a DNA sequence corresponding to a portion of the genome of a plant cell without other genomic DNA sequence(s) that normally flank and are covalently linked to the DNA sequence in nature. Such an "isolated" DNA molecule may comprise all or part of a transgene and/or transgenic event, which may comprise all or part of corn event ZM_BCS216090 or the transgene or expression cassette described herein. Nucleic acid sequences or elements, such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element or subpart is not within the genome of the organism, and at the location within the genome of the organism, in which it is naturally found. An "isolated" DNA molecule may be any recombinant DNA molecule or amplification product or amplicon, and/or may comprise any DNA sequence removed from its natural or biological state and covalently fused to another DNA molecule or sequence with which it is not associated in nature. Such an isolated DNA molecule could be created by the use of biotechnology techniques, such as by making a recombinant DNA or integrating a foreign or heterologous DNA molecule into the chromosome of a cell, plant, or seed. Thus, any DNA molecule comprising a transgenic, recombinant, chimeric or artificial nucleotide sequence, transgene or expression cassette would be considered to be an "isolated" DNA molecule since these sequences are not naturally occurring, regardless of whether the sequence, transgene or expression cassette is present within a plasmid, vector or construct used to transform plant cells, within the genome of a plant, plant part, plant tissue, or plant cell, or is present in detectable amounts in tissues, progeny, biological samples or commodity products derived from a plant, plant part, plant tissue, or plant cell. A recombinant DNA molecule or sequence, or any fragment derived therefrom, comprising all or part of a transgene or junction sequence of corn event would therefore also be considered to be "isolated." An "isolated" DNA molecule may be extracted or purified from a transgenic plant(s), plant part(s), plant cell(s) and/or tissue(s), or may be present in a homogenate, extract or lysate from any such transgenic plant(s), plant part(s), plant cell(s) and/or tissue(s), or may be produced as an amplicon or amplification product from plant genomic DNA and/or extracted or purified DNA from transgenic plant(s), plant part(s), plant cell(s) and/or tissue(s), or a homogenate, extract or lysate from plant(s), plant part(s), plant cell(s) and/or tissue(s). For the purposes of this disclosure, any transgenic polynucleotide or DNA sequence, i.e., the nucleotide sequence of the DNA inserted into the genome of a plant or bacterium, or present in an extrachromosomal vector, would be considered to be an "isolated" nucleotide or DNA sequence whether it is present within the plasmid or similar structure used to transform the cells, within the genome of the plant or bacterium, or present in detectable amounts in tissues, progeny, biological samples or commodity products derived from the plant or bacterium. An "isolated" DNA molecule is a chemical or biochemical molecule, regardless of whether the molecule is referred to as a nucleic acid, a nucleic acid sequence, a polynucleotide sequence, a DNA sequence, a nucleic acid molecule, a polynucleotide molecule, a DNA molecule, or the like. An "isolated" molecule can provide industrial applicability when present in a plant cell or in a plant genome or when present outside of a plant cell, and therefore, provides and exhibits (and is intended to provide and exhibit) utility regardless of where the molecule is located.

The phosphodiester bond linkage between one end of a transgenic insert (or insertion) into the genome of a plant and the flanking corn genomic DNA is referred to as a "junction." In other words, a "junction' is the connection point or covalent linkage of one end of a transgenic insert and the flanking genomic DNA. One junction is found at the 5' end of the transgenic insertion and the other is found at the 3' end of the transgenic insert, referred to herein as the 5' and 3' junction, respectively. A "junction sequence" refers to a DNA sequence of any length of consecutive nucleotides that spans the 5' or 3' junction of a transgenic event in the plant genome. For a "junction sequence" to be specific to a junction between a transgenic event and a flanking genomic sequence, the junction sequence will generally comprise a sufficient number of consecutive nucleotides at one end of the insertion and a sufficient number of consecutive nucleotides of the flanking genomic sequence. According to some embodiments, a "junction sequence" may comprise (i) at least five (5) consecutive nucleotides, at least ten (10) consecutive nucleotides, at least fifteen (15) consecutive nucleotides, at least twenty (20) consecutive nucleotides, or at least thirty (30) consecutive nucleotides at one end of the insertion and (ii) at least five (5) consecutive nucleotides, at least ten (10) consecutive nucleotides, at least fifteen (15) consecutive nucleotides, at least twenty (20) consecutive nucleotides, or at least thirty (30) consecutive nucleotides of flanking genomic DNA sequence, although it is understood that any length of consecutive nucleotides spanning a junction of a transgenic event in a plant genome may be a junction sequence. A variety of junction sequences of corn event ZM_BCS216090 can be determined by one of skill in the art using SEQ ID NO: 10. Examples of junction sequences of event ZM_BCS216090 are provided as SEQ ID NOs: 1-8. FIG. 1 illustrates the physical arrangement and locations of the junction sequences, arranged from 5' to 3' (left to right), relative to SEQ ID NO: 10. The junction sequences of event ZM_BCS216090 may be present as part of the genome of a corn plant, plant part, plant seed, or plant tissue or cell containing event ZM_BCS216090, a DNA molecule containing all or part of event ZM_BCS216090, or a microorganism containing event ZM_BCS216090. The identification of any one or more of the junction sequences in a DNA molecule or sample from a plant, plant part, plant seed, or plant tissue or cell indicates that the plant, plant part, plant seed, or plant tissue or cell contains or comprises event ZM_BCS216090, or the DNA molecule contains or comprises event ZM_BCS216090 or was obtained from a corn plant, plant part, plant seed, or plant tissue or cell containing or comprising event ZM_BCS216090, and is diagnostic in each case for the presence of event ZM_BCS216090.

A junction sequence for event ZM_BCS216090 may be represented by a sequence from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 10. For example, the junction sequences may be or comprise SEQ ID NO: 1 and SEQ ID NO: 2, SEQ ID NO: 1 and SEQ ID NO: 4, SEQ ID NO: 1 and SEQ ID NO: 6, SEQ ID NO: 3 and SEQ ID NO: 2, SEQ ID NO: 3 and SEQ ID NO: 4, SEQ ID NO: 3 and SEQ ID NO: 6, SEQ ID NO: 5 and SEQ ID NO: 2, SEQ ID NO: 5 and SEQ ID NO: 4, or SEQ ID NO: 5 and SEQ ID NO: 6. The junction sequences may comprise a first or 5' junction sequence and a second or 3' junction sequence, wherein the first or 5' junction sequence is or comprises one or more of SEQ ID NO: 1, SEQ ID NO: 3, and/or SEQ ID NO: 5, and wherein the second or 3' junction sequence is or comprises one or more of SEQ ID NO: 2, SEQ ID NO: 4, and/or SEQ ID NO: 6. Alternatively or additionally, a first or 5' junction sequence may be or comprise SEQ ID NO: 7, and/or a second or 5' junction sequence may be or comprise SEQ ID NO: 8.

The junction sequences described herein are diagnostic for the presence of all or part of event ZM_BCS216090 and/or a DNA molecule comprising all or part of the miRNA-encoding transgene, construct or expression cassette described herein. Thus, the identification or detection, directly or indirectly, of one or more of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 10 in a sample or DNA molecule derived from a corn plant, corn plant part, corn seed, or corn tissue or cell, or a commodity product from a corn plant, corn plant part, corn seed, or corn tissue or cell, is diagnostic that the corn plant, corn plant part, corn seed, or corn tissue or cell, or a commodity product from a corn plant, corn plant part, corn seed, or corn tissue or cell has or comprises all or part of corn event ZM_BCS216090. The identification or detection, directly or indirectly, of a 5' junction sequence and a 3' junction sequence (each as provided or described herein) in a sample or DNA molecule derived from a corn plant, corn plant part, corn seed, or corn tissue or cell, or a commodity product from a corn plant, corn plant part, corn seed, or corn tissue or cell, is diagnostic that the corn plant, corn plant part, corn seed, or corn tissue or cell, or a commodity product from a corn plant, corn plant part, corn seed, or corn tissue or cell has or comprises corn event ZM_BCS216090 The present disclosure thus provides a DNA molecule that contains at least one of the nucleotide sequences provided as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10. Any segment of DNA derived from transgenic corn event ZM_BCS216090 that is sufficient to include at least one of the sequences provided as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10 is within the scope of the present disclosure. In addition, any DNA or polynucleotide molecule or sequence comprising a sequence complementary to any of the sequences described herein is also within the scope of the present disclosure.

The disclosure provides DNA, polynucleotide or nucleic acid molecules, which may be single or double stranded, that can be used either as primers or probes for detecting the presence of DNA comprising all or part of event ZM_BCS216090 in a sample derived from a corn plant, corn plant part, corn seed, or corn tissue or cell, or a commodity product from a corn plant, corn plant part, corn seed, or corn tissue or cell. Such primers or probes are specific for a target nucleic acid, polynucleotide or DNA sequence and, as such, are useful for the identification of corn event ZM_BCS216090 nucleic acid, polynucleotide or DNA sequence by the methods described herein. A primer or probe can hybridize to a target nucleic acid, polynucleotide or DNA sequence to allow for specific detection or amplification of a nucleic acid, polynucleotide or DNA molecule or sequence that comprises, or is covalently linked and associated with, the target nucleic acid, polynucleotide or DNA sequence. According to present embodiments, the primers and/or probe may be chosen to identify and distinguish detection of a particular transgenic event and not only the presence of a transgene in a plant genome. The target nucleic acid, polynucleotide or DNA molecule or sequence may comprise all or part of corn event ZM_BCS216090, a junction sequence and/or flanking genomic DNA. Probes and primers according to the present disclosure may have (i) complete or 100% sequence complementarity (i.e., 100% complementary) to a target DNA sequence or (ii) incomplete sequence complementarity to a target DNA sequence, such as at least 60% complementary, at least 65% complementary, at least 70% complementary, at least 75% complementary, at least 80% complementary, at least 85% complementary, at least 90% complementary, at least 95% complementary, or at least 99% complementary to the target DNA sequence as long as the probe or primer has sufficient complementarity to the target DNA sequence to hybridize to the target DNA sequence under stringent hybridization conditions that are suitable and necessary for use of the probe or primer in the relevant amplification or detection assay, reaction or method. As understood in the art, the percentage complementarity of a primer or probe may be lower if the length of the primer or probe is longer and depends on the stringency and use.

A "probe" is a nucleic acid molecule that is complementary to a strand of target nucleic acid and is useful in hybridization methods. A probe may be attached a conventional detectable label or reporter molecule, e.g., a radioactive isotope, fluorophore, ligand, chemiluminescent agent, or enzyme. Such a probe is complementary to a strand of a target nucleic acid and, in the case of the present disclosure, to a strand of DNA from event ZM_BCS216090 whether from an event ZM_BCS216090 containing plant or from a sample that includes event ZM_BCS216090 DNA. Probes according to the present invention include not only deoxyribonucleic or ribonucleic acids, but also polyamides and other probe materials that bind specifically to a target DNA sequence and can be used to detect the presence of that target DNA sequence. An exemplary DNA sequence useful as a probe for detecting corn event ZM_BCS216090 is provided as SEQ ID NO: 13 (PB50583). A "probe" may also be used to bind a template DNA in a sample comprising all or part of a DNA or nucleotide sequence of corn event ZM_BCS216090 to purify the template DNA from the remainder of the sample using purification methods or techniques known in the art, for example, if the probe is bound or can be bound to a substrate or a particle or bead that can be purified or separated. Such a template DNA may comprise all or part of a DNA or nucleotide sequence of corn event ZM_BCS216090, or a portion or fragment thereof, such as a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, or a complement thereof.

A "primer" is a DNA molecule or oligonucleotide that is designed for use in specific annealing or hybridization methods that involve an in vitro amplification reaction. A pair of primers may be used with template DNA (such as a sample of corn genomic DNA) in a thermal amplification reaction (such as polymerase chain reaction (PCR)) or any other suitable amplification method known in the art to produce an amplification product or amplicon, where the amplicon produced from such reaction would have a DNA sequence corresponding to sequence of the template DNA located between the two sites where the primers hybridized to the template DNA. As understood in the art, an "amplification product" or "amplicon" is a DNA molecule or segment produced by an amplification reaction. Amplification or amplifying refers to making multiple copies of a target DNA molecule or segment from a template DNA. A single "primer" may also be used to initiate a sequencing reaction to determine a DNA sequence of a template DNA according to sequencing methods known in the art. Such a sequencing reaction may be used to determine the presence or absence of a DNA molecule or nucleotide sequence, or a portion or fragment thereof, from corn event ZM_BCS216090. Such a template DNA may comprise all or part of a DNA or nucleotide sequence of corn event ZM_BCS216090, or a portion or fragment thereof, such as a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, or a complement thereof.

DNA amplification reactions, methods and techniques are known to those skilled in art. DNA amplification can be accomplished by any of the various nucleic acid amplification methods known in the art, including thermal and isothermal amplification methods including the polymerase chain reaction or PCR. Amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb (kilobase) of genomic DNA and up to 42 kb of bacteriophage DNA (Cheng et al., *Proc. Natl. Acad. Sci. USA* 91:5695-5699, 1994). These methods as well as other methods known in the art of DNA amplification may be used in the practice of the present invention. Examples of DNA amplification methods include PCR, Recombinase Polymerase Amplification (RPA) (see for example U.S. Pat. No. 7,485,428), Strand Displacement Amplification (SDA) (see for example, U.S. Pat. Nos. 5,455, 166 and 5,470,723), Transcription-Mediated Amplification (TMA) (see for example, Guatelli et al., *Proc. Natl. Acad. Sci. USA* 87:1874-1878, 1990), Rolling Circle Amplification (RCA) (see for example, Fire and Xu, *Proc. Natl. Acad Sci. USA* 92:4641-4645, 1995; Lui, et al., *J. Am. Chem. Soc.* 118:1587-1594, 1996; Lizardi, et al., *Nature Genetics* 19:225-232, 1998; U.S. Pat. Nos. 5,714,320 and 6,235,502), Helicase Dependent Amplification (HDA) (see for example Vincent et al., *EMBO Reports* 5(8): 795-800, 2004; U.S. Pat. No. 7,282,328), and Multiple Displacement Amplification (MDA) (see for example Dean et al., *Proc. Natl. Acad Sci. USA* 99:5261-5266, 2002). A sequence of the heterologous DNA insert and/or flanking genomic DNA sequence from corn event ZM_BCS216090 can be verified or tested by amplifying such DNA molecules from corn seed containing event ZM_BCS216090 DNA or corn plants grown from the corn seed containing event ZM_BCS216090 DNA, using primers derived from the sequences provided herein, followed by standard DNA sequencing of the PCR amplicon or a cloned DNA fragment thereof.

According to present embodiments, the sequence of an amplicon of an amplification reaction may comprise one or more of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, or a fragment thereof. According to present embodiments, the sequence of an amplicon comprises at least one junction sequence or two junction sequences, such as a 5' junction sequence and/or a 3' junction sequence for corn event ZM_BCS216090.

A primer is typically designed to hybridize in a sequence-specific manner to a complementary target DNA strand to form a hybrid between the primer and target DNA strand, and the primer hybridized or bound to the complementary target DNA strand is a point of recognition for a polymerase to begin extension of the primer (i.e., polymerization of additional nucleotides into a lengthening nucleotide molecule) using as a template the target DNA strand. Primer pairs refer to use of two primers binding opposite strands of a double stranded DNA or polynucleotide segment for the purpose of amplifying the polynucleotide or DNA segment between the positions targeted for binding by the individual primers of the primer pair to the original template DNA or an amplicon of the amplification reaction, typically in a thermal cycling amplification reaction or other conventional DNA amplification method. Primer pairs are typically designed to hybridize to different nearby target positions of a template DNA molecule on opposing strands of the template DNA molecule such that the intervening region or sequence between the two primers can be specifically amplified for use or detection through multiple rounds of amplification.

To detect the presence or absence of corn event ZM_BCS216090, the target positions and/or the intervening region or sequence of a template DNA molecule may comprise at least one junction sequence and/or at least a portion of the insert of corn event ZM_BCS216090. To detect the absence of corn event ZM_BCS216090, the target positions and/or the intervening region or sequence of a template DNA molecule may comprise corn genomic DNA that does not include a junction sequence or any portion of the insert of corn event ZM_BCS216090. Thus, the presence or absence of an amplicon with a primer pair may be diagnostic of the presence or absence, respectively, of corn event ZM_BCS216090 in a DNA molecule or sample, or vice versa. This may also be possible with more than one primer pair. For example, a first primer pair may produce a first amplicon if corn event ZM_BCS216090 is present, and a second primer pair may produce a second amplicon if corn event ZM_BCS216090 is absent or not present. Alternatively, the size of an amplicon produced in an amplification reaction may also be diagnostic of the presence or absence of corn event ZM_BCS216090 in a DNA molecule or sample—e.g., a primer pair may produce a first amplicon of a first size if corn event ZM_BCS216090 is present or a second amplicon of a second size if corn event ZM_BCS216090 is absent and not present; or a first primer pair may produce a first amplicon of a first size if corn event ZM_BCS216090 is present, and a second primer pair may produce a second amplicon of a second size if corn event ZM_BCS216090 is absent or not present. According to some of these embodiments, at least two primer pairs may be used wherein at least one of the primer pairs is used as an internal control and is not associated with corn event ZM_BCS216090.

According to present embodiments, a primer pair to detect the presence of all or part of corn event ZM_BCS216090 in a DNA molecule or sample comprises a first primer and a second primer, wherein the first primer is complementary to a 5' flanking genomic DNA sequence and the second primer is complementary to a sequence within the transgenic insert; or wherein the first primer is complementary to a 5' flanking genomic DNA sequence and the second primer is complementary to a 3' flanking genomic DNA sequence; or wherein the first primer is complementary to a 3' flanking genomic DNA sequence and the second primer is complementary to a 5' flanking genomic DNA sequence; or wherein the first primer is complementary to a sequence within the transgenic insert and the second primer is complementary to a 3' flanking genomic DNA sequence; or wherein the first primer is complementary to a sequence within the transgenic insert and the second primer is complementary to a 5' flanking genomic DNA sequence; or wherein the first primer is complementary to a 3' flanking genomic DNA sequence and the second primer is complementary to a sequence within the transgenic insert. Each reference in this paragraph to a primer complementary to a 5' flanking genomic DNA sequence, a 3' flanking genomic DNA sequence, or a sequence within the transgenic insert of corn event ZM_BCS216090 is also intended to potentially include a primer complementary to the reverse complement or opposing strand of the respective 5' flanking genomic DNA sequence, 3' flanking genomic DNA sequence, or sequence within the transgenic insert of corn event ZM_BCS216090.

Exemplary DNA molecules useful as primers are provided as SEQ ID NO: 11, SEQ ID NO: 12, SEQ ID NO: 14, and SEQ ID NO: 15. The primer pair SEQ ID NO: 11 and SEQ ID NO: 12 can be useful as a first DNA molecule or primer and a second DNA molecule or primer, wherein each primer has sufficient length of consecutive nucleotides of SEQ ID NO: 10 or a sequence complementary to SEQ ID NO: 10 to function as DNA primers that, when used together in an amplification reaction with template DNA derived from corn event ZM_BCS216090, hybridize to opposite strands of the template DNA and produce an amplicon diagnostic for corn event ZM_BCS216090 DNA in a sample. The primer pair SEQ ID NO: 14 and SEQ ID NO: 15 are useful as a first DNA molecule or primer and a second DNA molecule or primer, wherein each primer has sufficient length of consecutive nucleotides of a locus within the corn genome to function as DNA primers that, when used together in a thermal amplification reaction with template DNA derived from corn event ZM_BCS216090, to produce an amplicon that serves as an internal control for both the diagnosis of corn event ZM_BCS216090, as well as the zygosity of corn event ZM_BCS216090 DNA in a sample.

DNA probes and DNA primers are generally eleven (11) polynucleotides or more in length, and often eighteen (18) polynucleotides or more, twenty-one (21) polynucleotides or more, twenty-four (24) polynucleotides or more, or thirty (30) polynucleotides or more in length. Such probes and primers are selected to be of sufficient length and sequence complementarity to a target sequence to hybridize specifically to the target sequence under high stringency hybridization conditions. Preferably, probes and primers according to the present disclosure have complete sequence complementarity or identity with the target sequence, although probes and primers differing from the target sequence in terms of identity or complementarity but retain the ability to hybridize to the target sequence may be designed by conventional methods.

The nucleic acid probes and primers of the present disclosure hybridize under stringent conditions to a target DNA molecule. Any conventional nucleic acid hybridization or amplification method can be used to detect or identify the presence of a target DNA from a transgenic plant in a sample. Polynucleic acid or DNA molecules, also referred to as nucleic acid or DNA segments or fragments thereof, are capable of specifically hybridizing to other complementary nucleic acid or DNA molecules under certain circumstances.

As used herein, two polynucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, nucleic acid molecules are said to exhibit "complete complementarity" and are "completely complementary" when every nucleotide of one of the molecules is complementary to a nucleotide of the other, in order of their respective sequences. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, DC (1985). Departures from complete complementarity are therefore permissible, as long as such departures do not completely preclude the capacity of the molecules to form a double-stranded structure. In order for a nucleic acid molecule to serve as a primer or probe, it need only be sufficiently complementary in sequence to be able to form a stable double-stranded structure under the particular solvent and salt concentrations and other conditions employed.

As used herein, a substantially homologous sequence in relation to a reference nucleic acid sequence is a nucleic acid sequence that will specifically hybridize to the complement of the reference nucleic acid sequence to which it is being compared under high stringency conditions.

Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In some embodiments, a polynucleic acid of the present disclosure, such as a primer or probe, will specifically hybridize to one or more of the nucleic acid molecule sequences set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and/or SEQ ID NO: 10, or complements thereof or fragments thereof, under moderately stringent conditions, for example at about 2.0×SSC and about 65° C. In some embodiments, a nucleic acid of the present disclosure, such as a primer or probe, will specifically hybridize to one or more of the nucleic acid molecule sequences set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and/or SEQ ID NO: 10, or complements or fragments thereof, under high stringency conditions. In one aspect of the present invention, a preferred nucleic acid molecule of the present disclosure has or comprises the nucleic acid sequence set forth in one or more of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, SEQ ID NO: 9, and/or SEQ ID NO: 10, or complements thereof, or fragments thereof. The hybridization of a nucleic acid molecule, such as a primer or probe, to a target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic acid sequence to which a primer having the corresponding sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the nucleic acid or DNA product of a polynucleic acid or DNA amplification reaction or method as further described herein, which is directed to a target polynucleic acid or DNA molecule that is part of a template polynucleic acid or DNA molecule. For example, to determine whether a corn plant, etc., resulting from a sexual cross of two parents contains transgenic plant genomic DNA from a corn plant comprising event ZM_BCS216090 of the present disclosure, DNA may be extracted from a corn plant tissue sample and subjected to an amplification reaction or method using a primer pair that is specific for a target sequence that is uniquely associated or part of event ZM_BCS216090, such as, for example, a first primer derived from a genomic DNA sequence in the region flanking the heterologous inserted DNA of event ZM_BCS216090 that is elongated by polymerase 5' to 3' in the direction of the inserted DNA, and a second primer derived from the heterologous inserted DNA molecule that is elongated by the polymerase 5' to 3' in the direction of the flanking genomic DNA from which the first primer is derived. The amplicon may range in length from the combined length of the primer pair plus one nucleotide base pair, or plus about fifty nucleotide base pairs, or plus about two hundred-fifty nucleotide base pairs, or plus about four hundred-fifty nucleotide base pairs or more depending on the length of the intervening polynucleic acid, polynucleotide or DNA sequence between the two primer target sequences in the template polynucleic acid, polynucleotide or DNA molecule. Alternatively, a primer pair can be derived from genomic sequence on both sides of the inserted heterologous DNA so as to produce an amplicon that includes the entire insert polynucleotide sequence (e.g., a forward primer isolated from the genomic portion on the 5' end of SEQ ID NO: 10 and a reverse primer isolated from the genomic portion on the 3' end of SEQ ID NO: 10 that amplifies a DNA molecule comprising the inserted DNA sequence (SEQ ID NO: 9) identified herein in the event ZM_BCS216090 genome). A member of a primer pair derived from the plant genomic sequence adjacent to the inserted transgenic DNA is located a distance from the inserted DNA sequence, this distance can range from one nucleotide base pair up to about twenty thousand nucleotide base pairs. The use of the term "amplicon" specifically excludes primer dimers that may be formed in a DNA amplification reaction.

For practical purposes, one should design primers which produce amplicons of a limited size range, for example, between 100 to 1000 bases. Smaller (shorter polynucleotide length) sized amplicons in general are more reliably produced in thermal amplification reactions, allow for shorter cycle times, and can be easily separated and visualized on agarose gels or adapted for use in endpoint TaqMan®-like assays. Smaller amplicons can be produced and detected by methods known in the art of DNA amplicon detection. In addition, amplicons produced using the primer pairs can be cloned into vectors, propagated, isolated, and sequenced or can be sequenced directly with methods well established in the art. Any primer pair of forward and reverse primers, which may be identical or complementary to part of SEQ ID NO: 10, such as an appropriate combination of SEQ ID NOs: 11, 12, 14, and 15, that is useful in a DNA amplification method to produce an amplicon diagnostic for event ZM_BCS216090 or progeny thereof is an aspect of the disclosure.

Any single isolated DNA polynucleotide primer molecule comprising at least 15 contiguous nucleotides of SEQ ID NO: 10, or its complement that is useful in a DNA amplification method to produce an amplicon diagnostic for event ZM_BCS216090 or progeny thereof is an aspect of the disclosure. Any single isolated DNA polynucleotide primer molecule comprising at least 15 contiguous nucleotides of SEQ ID NO: 12, or its complement that is useful in a DNA amplification method to produce an amplicon diagnostic for plants comprising event ZM_BCS216090 or progeny thereof is an aspect of the disclosure. Any single isolated DNA polynucleotide primer molecule comprising at least 15 contiguous nucleotides of SEQ ID NO: 9, or its complement that is useful in a DNA amplification method to produce an amplicon diagnostic for event ZM_BCS216090 or progeny thereof is an aspect of the disclosure.

A diagnostic amplicon produced by the methods described herein may be detected by a plurality of techniques known in the art, such as sequencing, restriction mapping, Northern analysis, Southern analysis, or any other suitable polynucleotide or DNA hybridization, blotting, polymerization and/or amplification based approach or technique. One method is Genetic Bit Analysis (Nikiforov et al., *Nucleic Acid Res.* 22:4167-4175, 1994) where a DNA oligonucleotide is designed that overlaps both the adjacent flanking genomic DNA sequence and the inserted DNA sequence—i.e., a junction sequence. The oligonucleotide is immobilized in wells of a microtiter plate. Following PCR of the region of interest (using, for example, one primer in the inserted sequence and one in the adjacent flanking genomic sequence), a single-stranded PCR product can be hybridized to the immobilized oligonucleotide and serve as a template for a single base extension reaction using a DNA polymerase and labeled dideoxynucleotide triphosphates (ddNTPs) specific for the expected next base. Readout may be fluorescent or ELISA-based. A signal indicates presence of the transgene/genomic junction sequence due to successful amplification, hybridization, and single base extension.

Another method is the pyrosequencing technique as described by Winge (*Innov. Pharma. Tech.* 00:18-24, 2000). In this method, an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene/genomic sequence due to successful amplification, hybridization, and single or multi-base extension.

Fluorescence Polarization as described by Chen et al. (*Genome Res.* 9:492-498, 1999) is a method that can be used to detect the amplicon of the present invention. Using this method an oligonucleotide is designed that overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene/genomic sequence due to successful amplification, hybridization, and single base extension.

Real-time polymerase chain reaction (PCR) is the ability to monitor the progress of the PCR as it occurs (i.e., in real time). Data is collected throughout the PCR process, rather than at the end of the PCR. In real-time PCR, reactions are characterized by the point in time during cycling when amplification of a target is first detected rather than the amount of target accumulated after a fixed number of cycles. In a real-time PCR assay, a positive reaction is detected by accumulation of a fluorescent signal. The higher the starting copy number of the nucleic acid target, the sooner a significant increase in fluorescence is observed. The cycle threshold (Ct value) is defined as the number of cycles required for the fluorescent signal to cross the threshold (i.e., exceeds background level). Ct levels are inversely proportional to the amount of target nucleic acid in the sample (i.e., the lower the Ct value, the greater the amount of target nucleic acid in the sample).

Tagman® (PE Applied Biosystems, Foster City, CA) is described as a method of detecting and quantifying the presence of a DNA sequence using real-time PCR and is fully understood in the instructions provided by the manufacturer. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermalstable polymerase and dNTPs. Hybridization of the FRET probe results in cleavage and release of the fluorescent moiety away from the quenching moiety on the FRET probe. A fluorescent signal indicates the presence of the transgene/genomic sequence due to successful amplification and hybridization.

Molecular beacons have been described for use in sequence detection as described in Tyangi et al. (*Nature Biotech.* 14:303-308, 1996). Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermalstable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

Other detection methods known in the art may be used. For example, microfluidics (see, e.g., U.S. Patent Publication No. 2006/068398; U.S. Pat. No. 6,544,734) provide methods and devices that can be used to separate and amplify DNA samples or molecules. Optical dyes can be used to detect and measure specific DNA molecules (see, e.g., WO/05017181). Nanotube devices (see, e.g., WO/06024023) that comprise an electronic sensor for the detection of DNA molecules or nanobeads that bind specific DNA molecules can then be detected.

DNA detection kits that are based on DNA amplification methods contain DNA primer molecules that hybridize specifically to a target DNA and amplify a diagnostic amplicon under the appropriate reaction conditions. The kit may provide an agarose gel based detection method or any number of methods of detecting the diagnostic amplicon that are known in the art. DNA detection kits can be developed using the compositions disclosed herein and are useful for identification of corn event ZM_BCS216090 DNA in a sample and can be applied to methods for breeding corn plants containing event ZM_BCS216090 DNA. A kit that contains DNA primers that are homologous or complementary to any portion of the corn genomic region as set forth in SEQ ID NO: 10 and to any portion of the inserted transgenic DNA as set forth in SEQ ID NO: 9 is an object of the invention. The DNA molecules can be used in DNA amplification methods (PCR) or as probes in polynucleic acid hybridization methods, i.e., southern analysis, northern analysis, etc. Kits of the invention may optionally also comprise reagents or instructions for performing the detection or diagnostic reactions described herein.

Probes and primers as provided herein may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed. Any conventional nucleic acid hybridization or amplification method can be used to identify the presence of transgenic DNA from corn event ZM_BCS216090 in a sample.

Any number of methods well known to those skilled in the art can be used to isolate and manipulate a DNA molecule, or fragment thereof, disclosed herein, including DNA isolation or thermal amplification or PCR methods. Such DNA molecule or fragment may be inserted or placed into any suitable vector or plasmid or combined with other elements, sequences or fragments using molecular or recombinant techniques.

The DNA molecules and corresponding nucleotide sequences provided herein are therefore useful for, among other things, identifying corn event ZM_BCS216090, detecting the presence of DNA derived from the transgenic corn event ZM_BCS216090 in a sample, and monitoring samples for the presence and/or absence of corn event ZM_BCS216090 or plant parts derived from corn plants comprising event ZM_BCS216090.

Reference herein to "corn" generally is intended to include corn plants, corn plant cells, corn plant tissues, corn seeds, corn plant parts, corn progeny plants, and/or corn commodity products, depending on the context of its use herein, unless otherwise provided. The present disclosure provides corn plants, corn plant cells, corn plant tissues, corn seeds, corn plant parts (such as pollen, ovule, silk, spike, anther, cob, root tissue, stalk tissue, leaf tissue), corn progeny plants, and corn commodity products. These corn plants, corn plant cells, corn plant tissues, corn seeds, corn plant parts, corn progeny plants, and corn commodity products contain a detectable amount of a polynucleotide or DNA molecule or sequence comprising at least one junction sequence and/or heterologous insert sequence of corn event ZM_BCS216090, such as a polynucleotide or DNA molecule or sequence having or comprising at least one of the sequences provided as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

The invention provides corn plants, corn plant cells, corn plant tissues, corn seeds, corn plant parts (such as pollen, ovule, silk, spike, anther, cob, root tissue, stalk tissue, leaf tissue), corn progeny plants, or corn commodity products that either contain or comprise ZM_BCS216090 DNA or are derived from a transgenic corn plant, corn plant cell, corn plant tissue, corn seed, corn plant part, corn progeny plant, or corn commodity product containing or comprising event ZM_BCS216090 DNA. A representative sample of corn seed containing event ZM_BCS216090 DNA has been deposited according to the Budapest Treaty with the American Type Culture Collection (ATCC®). The ATCC repository has assigned the Patent Deposit Designation PTA-127050 to the seed containing event ZM_BCS216090 DNA.

The present disclosure further provides a microorganism, such as a bacterial or fungal cell, comprising a DNA molecule having at least one sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, which may be present in its genome. A microorganism is intended to include any microscopic cell or organism, whether prokaryote or eukaryote or otherwise, that contains DNA within a genome or chromosome or an extra-chromosomal DNA structure, such as a plasmid or vector, in such microscopic cell. Microscopic cells or organisms include bacteria (prokaryotes) and cells corresponding to higher life forms (eukaryotes) which are beneath the visual range of the average human. An example of such a microorganism is a transgenic plant cell. Microorganisms, such as a plant cell of the present disclosure, are useful in many industrial applications, including but not limited to: (i) use as research tool for scientific inquiry or industrial research; (ii) use in culture for producing endogenous or recombinant carbohydrate, lipid, nucleic acid, or protein products or small molecules that may be used for subsequent scientific research or as industrial products; and (iii) use with modern plant tissue culture techniques to produce transgenic plants, plant parts, plant organs or plant tissue cultures that may then be used for agricultural research or production. The production and use of microorganisms, such as transgenic plant cells, utilizes modern microbiological techniques and human intervention to pro-duce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The transgenic plant cell's new genetic composition and phenotype is a technical effect created by the integration or insertion of the heterologous DNA into the genome of the cell. Another aspect of the present disclosure is a method of using a microorganism provided herein. Methods of using microorganisms of the present disclosure, such as transgenic plant cells, include (i) methods of producing transgenic cells by integrating recombinant DNA into the genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, or protein products from cultured cells; and (iv) methods of using modern plant tissue culture techniques with transgenic plant cells to produce transgenic plants or transgenic plant tissue cultures.

Corn plants of the present disclosure may pass along the event ZM_BCS216090 DNA, including the transgene inserted as part of corn event ZM_BCS216090, to progeny or offspring. Such progeny may include any corn plant, plant cell, seed, gamete and/or regenerable plant part containing or comprising the event ZM_BCS216090 DNA inherited or derived from an ancestor or parental corn plant(s), at least one of which comprises a DNA molecule having or comprising at least one sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10. Corn plants, progeny, and seeds may be homozygous or heterozygous for the event ZM_BCS216090 and the transgene of event ZM_BCS216090. Progeny may be grown from seeds produced by a corn plant comprising or containing event ZM_BCS216090 and/or from seeds produced by a plant fertilized with pollen from a corn plant comprising or containing event ZM_BCS216090 (i.e., fertilized with pollen comprising or containing event ZM_BCS216090).

Methods for producing corn plants and seeds containing or comprising maize event ZM_BCS216090 are provided. Corn plants may be bred using any method known in the art, for example, descriptions of breeding methods that are commonly used can be found in WR Fehr, in *Breeding Methods for Cultivar Development*, Wilcox J. ed., American Society of Agronomy, Madison WI (1987). Corn plants or progeny plants containing or comprising maize event ZM_BCS216090 may be self-pollinated (also known as "selfing") to generate a true breeding line of corn plants, i.e., corn plants homozygous for the transgene and event ZM_BCS216090. Selfing can result in progeny known as an "inbred" that can be used to produce corn inbred lines that are genetically uniform.

Alternatively, corn plants or progeny plants containing or comprising maize event ZM_BCS216090 may be out-crossed or cross-pollinated (also known as "crossing"), e.g., bred with another plant having a different germplasm or genotype, to produce a varietal or hybrid seed or plant that may be homozygous or heterozygous for the transgene and event ZM_BCS216090 depending on whether the other parental plant also comprises or contains the transgene and event ZM_BCS216090. The other parental plant may be transgenic or non-transgenic for the same and/or different trait, transgene or event. A varietal or hybrid seed or plant of the invention may thus be derived by sexually crossing a first parent that lacks the specific and unique corn event ZM_BCS216090 with a second parent comprising corn event ZM_BCS216090, resulting in a hybrid plant or progeny plant containing or comprising the specific and unique corn event ZM_BCS216090. Each parent can be a hybrid or an inbred/varietal plant, so long as a parent or progeny plant or seed of the cross has or comprises at least one copy of the corn event ZM_BCS216090 and/or a DNA molecule having or comprising at least one sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

Sexually crossing one plant with another plant, i.e., cross-pollinating, may be accomplished or facilitated by human intervention, for example: by human hands or other mechanical means under human, computer or automated control collecting the pollen of one plant and contacting this pollen with the style or stigma of a second plant; by human hands and/or human actions or other mechanical means under human, computer or automated control removing, destroying, devitalizing or covering the stamen or anthers of a plant (e.g., by manual intervention or by application of a chemical gametocide) so that natural self-pollination is prevented and cross-pollination would have to take place in order for fertilization to occur; by human placement of pollinating insects in a position for "directed pollination" (e.g., by placing beehives in orchards or fields or by caging plants with pollinating insects); by human opening or removing of parts of the flower to allow for placement or contact of foreign pollen on the style or stigma; by selective placement of plants (e.g., intentionally planting plants in pollinating proximity); and/or by application of chemicals to precipitate flowering or to foster receptivity (of the stigma for pollen).

Two different transgenic plants may thus be crossed to produce hybrid offspring plants, plant parts and/or seeds that contain two independently segregating transgenes or events wherein at least one of those transgenes or events comprises or is contained within corn event ZM_BCS216090. For example, transgenic plants comprising corn event ZM_BCS216090 can be crossed with other transgenic corn plants to produce a plant having the characteristics of both transgenic parents. Back-crossing to a parental plant and out-crossing with a non-transgenic plant are also contemplated, as is vegetative propagation. Descriptions of other breeding methods that are commonly used for different traits and crops are known in the art and can be found in one of several references, e.g., Fehr, in *Breeding Methods for Cultivar Development*, Wilcox J. ed., American Society of Agronomy, Madison WI (1987).

According to some embodiments, a reduced plant height trait or phenotype may be used to select one or more progeny corn plants, plant parts or seeds that contain corn or maize event ZM_BCS216090. Alternatively, progeny plants, plant parts or seeds may be analyzed using diagnostic methods as described herein to select for plants, plant parts or seeds containing or comprising corn or maize event ZM_BCS216090.

Corn plants and progeny plants comprising corn event ZM_BCS216090 may have a short stature or semi-dwarf trait or phenotype and a lodging and/or green snap resistance trait or phenotype as described, for example, in PCT Application No. PCT/US2017/047405 (PCT Application Publication No. WO 2018/035354), the entire contents and disclo-sure of which are incorporated herein by reference. Corn plants, progeny, seeds, tissues, cells and plant parts comprising corn event ZM_BCS216090 as provided herein may also contain one or more additional corn trait(s) or transgenic event(s), such as by crossing a corn plant containing corn event ZM_BCS216090 with another corn plant containing the additional trait(s) or transgenic event(s). Such additional trait(s) or transgenic event(s) may include, but are not limited to, increased insect resistance, herbicide tolerance, increased water use efficiency, increased yield performance, increased drought resistance, increased seed quality, improved nutritional quality, hybrid seed production, or disease or fungal resistance. A corn trait may include any transgenic traits or mutant or edited traits or alleles. Mutant traits or alleles of a gene may be created by any mutagenesis technique known in the art, whereas edited traits may be generated by any genome editing method known in the art. Many corn transgenic event(s) are known to those of skill in the art. For example, a list of such traits is provided by the United States Department of Agriculture's (USDA) Animal and Plant Health Inspection Service (*APHIS*) and can be found on their website: www.aphis.usda.gov. Two or more allele(s) and/or transgenic event(s) comprising including at least one copy of corn event ZM_BCS216090 may thus be combined in a progeny seed or plant by crossing two parent plants each comprising one or more allele(s) and/or transgenic event(s), collecting the progeny seed, and selecting for progeny seed or plants that contain the two or more allele(s) and/or transgenic event(s). These steps may be repeated until the desired combination of transgenic event(s) and/or allele(s) in a progeny plant is achieved. For the present application, the progeny plant will generally comprise corn event ZM_BCS216090. Back-crossing to a parental plant and out-crossing with a non-transgenic plant are also contemplated and is vegetative propagation.

A plant part is provided that comprises event ZM_BCS216090 and/or is derived from corn plants comprising event ZM_BCS216090. As used herein, a "plant part" refers to any part of a plant which may comprise event ZM_BCS216090 and/or material derived from a corn plant comprising event ZM_BCS216090. Plant parts include, but are not limited to, plant tissue, pollen, ovule, silk, spike, anther, cob, root tissue, stalk tissue, and leaf tissue. Plant parts may be viable, nonviable, regenerable, and/or non-regenerable.

A commodity product is provided that is derived from one or more corn plants, plant parts, seeds and/or plant tissues comprising event ZM_BCS216090 and that contains a detectable amount of a nucleic acid or DNA molecule, segment or sequence specific for event ZM_BCS216090. As used herein, a "commodity product" refers to any composition or product comprising material derived from one or more corn plants, whole or processed corn seed, one or more plant cells, and/or one or more plant parts containing or comprising the corn event ZM_BCS216090 DNA. Nonviable commodity products include, but are not limited to, nonviable seeds, whole or processed seeds, seed parts, and plant parts; animal feed comprising corn, corn oil, corn meal, corn flour, corn flakes, corn bran, pasta made with corn, corn biomass, and fuel products produced using corn and corn parts. Viable commodity products include, but are not limited to, seeds, plants, and plant cells. The corn plants comprising event ZM_BCS216090 can thus be used to manufacture any commodity product typically acquired from corn. Any such commodity product that is derived from corn plants comprising event ZM_BCS216090 may contain at least a detectable amount of the specific and unique DNA corresponding to corn event ZM_BCS216090, and specifically may contain a detectable amount of a polynucleotide or DNA molecule having or comprising at least one sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10. Detection of one or more of these polynucleotide or DNA sequences in a sample may be used to determine or diagnose that the sample is taken from a corn plant, corn plant part, corn plant tissue, corn plant cell, and/or corn plant product, such as a corn commodity product, comprising event ZM_BCS216090, or to determine the content or source of a corn plant, corn plant part, corn plant tissue, corn plant cell, and/or corn plant product, such as a corn commodity product. Any standard method of detection for nucleotide molecules may be used, including methods of detection disclosed herein. A commodity product is within the scope of the present disclosure if there is any detectable amount of a DNA molecule having at least one sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10 contained or comprised in the commodity product.

The corn plants, corn plant cells, corn seeds, corn plant parts (such as pollen, ovule, silk, spike, anther, cob, root tissue, stalk tissue, leaf tissue), corn progeny plants, and commodity products of the present disclosure are therefore, useful for, among other things, growing plants for the purpose of producing seed and/or plant parts comprising corn event ZM_BCS216090 for agricultural purposes, producing progeny comprising corn event ZM_BCS216090 for plant breeding and research purposes, use with microbiological techniques for industrial and research applications, and sale to consumers.

Methods for producing corn plant(s) comprising the DNA sequences specific and unique to event ZM_BCS216090 of the present disclosure are provided. A progeny corn plant comprising the event ZM_BCS216090 may be produced, for example, by selfing a parent plant or line comprising the event ZM_BCS216090, wherein such parent plant or line is homozygous or hemizygous for the event ZM_BCS216090, or by crossing a first parent plant or line comprising the event ZM_BCS216090, wherein such parent plant or line is homozygous or hemizygous for the event ZM_BCS216090, with a second parent plant or line having a different genotype or germplasm than the first parent line, wherein the second parent plant or line may or may not contain or comprise the event ZM_BCS216090. As explained further herein, corn event ZM_BCS216090 contains an expression cassette or transgene encoding a miRNA that targets GA20 oxidase genes for suppression leading to lower active GA levels in the plant and a reduced plant height (i.e., a semi-dwarf phenotype or trait). According to some embodiments, the transgenic corn plant(s) comprising the event ZM_BCS216090 of the present disclosure is/are semi-dwarf and/or have a shorter plant height relative to a non-transgenic control plant. According to some embodiments, the transgenic corn plant(s) comprising the event ZM_BCS216090 of the present disclosure is/are lodging resistant (resistant to root and/or stalk lodging) and/or resistant to green snap, relative to a non-transgenic control plant. Transgenic plants used in these methods may be homozygous or heterozygous for the transgene. Progeny plants produced by these methods may be varietal or hybrid plants; may be grown from seeds produced by corn event ZM_BCS216090 containing plant and/or from seeds produced by a plant fertilized with pollen from a corn event ZM_BCS216090 containing plant; and may be homozygous or heterozygous for the transgene and/or event ZM_BCS216090. Progeny plants may be subsequently self-pollinated to generate a true breeding line of plants, i.e., plants homozygous for the transgene, or alternatively may be out-crossed, e.g., bred with another unrelated plant, to produce a varietal or a hybrid seed or plant.

Methods of detecting the presence of DNA derived from a corn cell, corn tissue, corn seed, corn plant part, or corn plant comprising corn event ZM_BCS216090 in a sample are provided. One method comprises (i) extracting a DNA sample from at least one corn cell, corn tissue, corn seed, or corn plant; (ii) contacting the DNA sample with at least one primer that is capable of producing DNA sequence specific to event ZM_BCS216090 DNA under conditions appropriate for DNA sequencing; (iii) performing a DNA sequencing reaction; and then (iv) confirming that the nucleotide sequence comprises a nucleotide sequence specific for event ZM_BCS216090, of the construct comprised therein, such as one selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

Another method comprises (i) extracting a DNA sample from at least one corn cell, corn tissue, corn seed, or corn plant; (ii) contacting the DNA sample with a primer pair that is capable of producing an amplicon from event ZM_BCS216090 DNA under conditions appropriate for DNA amplification; (iii) performing a DNA amplification reaction; and then (iv) detecting the amplicon molecule and/or confirming that the nucleotide sequence of the amplicon comprises a nucleotide sequence specific for event ZM_BCS216090, such as one selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10. The amplicon should be one that is specific for event ZM_BCS216090, such as an amplicon that comprises SEQ ID NO: 1, or SEQ ID NO: 2, or SEQ ID NO: 3, or SEQ ID NO: 4, or SEQ ID NO: 5, or SEQ ID NO: 6, or SEQ ID NO: 7, or SEQ ID NO: 8, or SEQ ID NO: 9, or SEQ ID NO: 10. The detection of a nucleotide sequence specific for event ZM_BCS216090 in the amplicon is determinative and/or diagnostic for the presence of the corn event ZM_BCS216090 specific DNA in the sample. An example of a primer pair that is capable of producing an amplicon from event ZM_BCS216090 DNA under conditions appropriate for DNA amplification is provided as SEQ ID NO: 11 and SEQ ID NO: 12. Other primer pairs may be readily designed by one of skill in the art to produce an amplicon comprising SEQ ID NO: 1, or SEQ ID NO: 2, or SEQ ID NO: 3, or SEQ ID NO: 4, or SEQ ID NO: 5, or SEQ ID NO: 6, or SEQ ID NO: 7, or SEQ ID NO: 8, or SEQ ID NO: 9, or SEQ ID NO: 10, wherein such a primer pair comprises at least one primer within the genomic region flanking the insert and a second primer within the insert, provided that any primer pair could be designed and used that produces an amplicon comprising a junction sequence and/or all or part of the insert or transgene sequence. Detection of an amplicon could be based on any suitable method, such as sequencing, determining fragment size or migration of the amplicon in a matrix or gel, or a hybridization based method.

Another method of detecting the presence of DNA derived from a corn cell, corn tissue, corn seed, or corn plant comprising corn event ZM_BCS216090 in a sample consists of (i) extracting a DNA sample from at least one corn cell, corn tissue, corn seed, or corn plant; (ii) contacting the DNA sample with a DNA probe specific for event ZM_BCS216090 DNA; (iii) allowing the probe and the DNA sample to hybridize under stringent hybridization conditions; and then (iv) detecting hybridization between the probe and the target DNA sample. An example of the sequence of a DNA probe that is specific for event ZM_BCS216090 is provided as SEQ ID NO: 13. Other probes may be readily designed by one of skill in the art and would comprise a junction sequence, at least one fragment of genomic DNA flanking the insert and at least one fragment of insert DNA, and/or one or more sequences provided in SEQ ID NO: 1, SEQ ID NO: 2, SEQ ID NO: 3, SEQ ID NO: 4, SEQ ID NO: 5, SEQ ID NO: 6, and SEQ ID NO: 10. Detection of probe hybridization to the DNA sample is diagnostic for the presence of corn event ZM_BCS216090 specific DNA in the sample. Absence of hybridization is alternatively diagnostic of the absence of corn event ZM_BCS216090 specific DNA in the sample.

DNA detection kits are provided that are useful for the identification of corn event ZM_BCS216090 DNA in a sample and can also be applied to methods for breeding corn plants containing the appropriate event DNA. Such kits contain DNA primers and/or probe(s) which are specific to corn event ZM_BCS216090. Such DNA primers and/or probe(s) may comprise one or more of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, or a fragment thereof. One example of such a kit comprises at least one DNA molecule of sufficient length of continuous nucleotides of SEQ ID NO:10 to function as a DNA probe useful for detecting the presence and/or absence of DNA derived from transgenic corn plants comprising event ZM_BCS216090 in a sample. The DNA derived from transgenic corn plants comprising event ZM_BCS216090 would comprise a DNA molecule having at least one sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10. Likewise, the primers may comprise a primer pair including a first primer and a second primer, wherein at least one of the primers hybridizes to a flanking sequence and the other primer hybridizes to either an insert sequence of event ZM_BCS216090 in the plant genome or the flanking sequence on the opposite side of the insert. The first and second primers hybridize to opposing strands of the corn plant genomic DNA at different spaced apart positions such that an amplification reaction involving the two primers produces an amplicon comprising the primer sequences and the intervening sequence between the two primers. A probe may be chosen to correspond or hybridize to the amplicon produced with a primer pair or set of primers and may comprise all or part of the primer sequence(s) and/or the intervening sequence of the amplicon between the two primers. Suitable probes may be readily designed by one of skill in the art and should comprise at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 contiguous nucleotides of SEQ ID NO: 10 and be sufficiently unique to corn event ZM_BCS216090 DNA in order to identify DNA derived from the event.

Another type of kit comprises a primer pair useful for producing an amplicon useful for detecting the presence and/or absence of DNA derived from transgenic corn event ZM_BCS216090 in a sample. Such a kit would employ a method comprising contacting a target DNA sample with a primer pair as described herein, then performing a nucleic acid amplification reaction sufficient to produce an amplicon comprising a DNA molecule having at least one sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10 and then detecting the presence and/or absence of the amplicon. Such a method may also include sequencing the amplicon or a fragment thereof, which would be determinative of, i.e., diagnostic for, the presence of the corn event ZM_BCS216090 specific DNA in the target DNA sample. Other primer pairs may be readily designed by one of skill in the art and should comprise at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of sequences provided in, but not limited to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, and be sufficiently unique to corn event ZM_BCS216090 DNA in order to identify DNA derived from the event.

The kits and detection methods of the invention are useful for, among other things, identifying corn event ZM_BCS216090, selecting plant varieties or hybrids comprising corn event ZM_BCS216090, detecting the presence of DNA derived from the transgenic corn plant comprising event ZM_BCS216090 in a sample, and monitoring samples for the presence and/or absence of corn plants comprising event ZM_BCS216090, or plant parts derived from corn plants comprising event ZM_BCS216090.

The sequences of the heterologous DNA insert, junction sequences, or flanking sequence from corn event ZM_BCS216090 can be determined or verified by amplifying such sequences from the event using primers derived from the sequences provided herein followed by standard DNA sequencing of the amplicon or of the cloned DNA.

Methods of detecting the zygosity of the event and transgene with genomic DNA derived from at least one corn cell, corn tissue, corn seed, corn plant part or corn plant comprising corn event ZM_BCS216090 in a sample are provided. One method consists of (i) extracting a DNA sample from at least one corn cell, corn tissue, corn seed, corn plant part, or corn plant; (ii) contacting the DNA sample with a first primer pair that is capable of producing a first amplicon diagnostic for event ZM_BCS216090; (iii) contacting the DNA sample with a second primer pair that is capable of producing a second amplicon diagnostic for native corn genomic DNA not comprising event ZM_BCS216090; (iv) performing a DNA amplification reaction; and then (v) detecting the amplicons, wherein the presence of only the first amplicon is diagnostic of a homozygous event ZM_BCS216090 DNA in the sample, the presence of both the first amplicon and the second amplicon is diagnostic of a corn plant heterozygous for event ZM_BCS216090, and the presence of only the second amplicon is diagnostic for the absence of event ZM_BCS216090 DNA in the sample. An exemplary set of primers pairs are presented as SEQ ID NO: 11 and SEQ ID NO: 12 which produce an amplicon diagnostic for event ZM_BCS216090; and SEQ ID NO: 14 and SEQ ID NO: 15 which produces an amplicon diagnostic for non-inserted wild-type corn genomic DNA not comprising event ZM_BCS216090. A set of probes can also be incorporated into such an amplification method to be used in a real-time PCR format using the primer pair sets described above. An exemplary set of probes are presented as SEQ ID NO: 13 (diagnostic for the amplicon for the event ZM_BCS216090) and SEQ ID NO: 16 (diagnostic for the amplicon for wild-type corn genomic DNA not comprising event ZM_BCS216090).

Another method for determining zygosity consists of (i) extracting a DNA sample from at least one corn cell, corn tissue, corn seed, corn plant part, or corn plant; (ii) contacting the DNA sample with a probe set which contains at least a first probe that specifically hybridizes to event ZM_BCS216090 DNA and at least a second probe that specifically hybridizes to corn genomic DNA that was disrupted by insertion of the heterologous DNA of event ZM_BCS216090 and does not hybridize to event ZM_BCS216090 DNA; (iii) hybridizing the probe set with the sample under stringent hybridization conditions, wherein detecting hybridization of only the first probe under the hybridization conditions is diagnostic for a homozygous corn cell, corn tissue, corn seed, corn plant part, or corn plant for event ZM_BCS216090 DNA in the sample; wherein detecting hybridization of both the first probe and the second probe under the hybridization conditions is diagnostic for a heterozygous corn cell, corn tissue, corn seed, corn plant part, or corn plant for event ZM_BCS216090 in a DNA sample; and detecting hybridization of only the second probe under the hybridization conditions is diagnostic for the absence of event ZM_BCS216090 DNA in the sample.

Yet another method for determining zygosity consists of (i) extracting a DNA sample from at least one corn cell, corn tissue, corn seed, corn plant part, or corn plant; (ii) contacting the DNA sample with a first primer pair that is capable of producing a first amplicon diagnostic for event ZM_BCS216090; (iii) contacting the DNA sample with a second primer pair that is capable of producing a second amplicon of an internal standard known to be single-copy and homozygous in the corn plant; (iv) contacting the DNA sample with a probe set which contains at least a first probe that specifically hybridizes to the first amplicon, and at least a second probe that specifically hybridizes to the second amplicon; (v) performing a DNA amplification reaction using real-time PCR and determining the cycle thresholds (Ct values) of the first and second amplicons; (vi) calculating the difference ($\Delta$Ct) between the Ct value of the first amplicon and the second amplicon; and (vii) determining zygosity, wherein a $\Delta$Ct of about zero (0) indicates homozygosity of the event or inserted T-DNA, and a $\Delta$Ct of about one (1) indicates heterozygosity of the event or inserted T-DNA. Heterozygous and homozygous events are differentiated by a $\Delta$Ct value unit of approximately one (1). Given the normal variability observed in real-time PCR due to multiple factors such as amplification efficiency and ideal annealing temperatures, the range of "about one (1)" is defined as a $\Delta$Ct of 0.75 to 1.25, and the range of "about zero (0)" is defined as a $\Delta$Ct of −0.25 to 0.25 (or of 0.0 to 0.25 if the $\Delta$Ct is measured as an absolute value). Primer pairs and probes for the above method for determining zygosity can amplify and detect amplicons from the transgene or event DNA and the internal DNA standard.

According to embodiments of the present disclosure, a transgenic corn plant or plant part, one or more transgenic corn plants or plant parts or a plurality transgenic corn plants or plant parts as provided herein, or an agricultural field or soil in which a transgenic corn plant or plant part, one or more transgenic corn plants or plant parts or a plurality of transgenic corn plants or plant parts as provided herein are planted or grown, can be treated with an agricultural composition comprising one or more active ingredients or other agents, such as, for example and without limitation, an herbicide or one or more herbicides, a fungicide or one or more fungicides, an insecticide or one or more insecticides, a plant growth regulator or plant stimulant or one or more plant growth regulators and/or plant stimulants, and/or a safener or one or more safeners. Provided below are lists of possible or representative compounds for each of these types of actives or agents, and an agricultural composition may comprise one or any combination or multiplicity of these actives, agents or compounds. Such an agricultural composition may be applied, for example, as a foliar, soil or in-furrow treatment, as a pre-emergent, pre-sowing and/or post-emergent treatment, and/or in some cases, may be applied to a transgenic plant part or seed provided herein.

An agricultural composition may be formulated according to its intended use and application. The appropriate formulation of the agricultural composition may be chosen to have different physicochemical parameters, components and stabilities of the respective compound(s). Possible types of formulations for an agricultural composition can include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes. If appropriate, some agricultural compositions of a pesticidal compound or one or more pesticidal compounds might be formulated and used as a seed coating applied to a plant part or seed as provided herein.

Deposit Information

A deposit of a representative sample of corn seed containing event ZM_BCS216090 was made on Jul. 14, 2021 according to the Budapest Treaty with the American Type Culture Collection (ATCC) having an address at 10801 University Boulevard, Manassas, Virginia 20110, USA, and assigned ATCC Accession No. PTA-127050.

EXAMPLES

Figure 4:
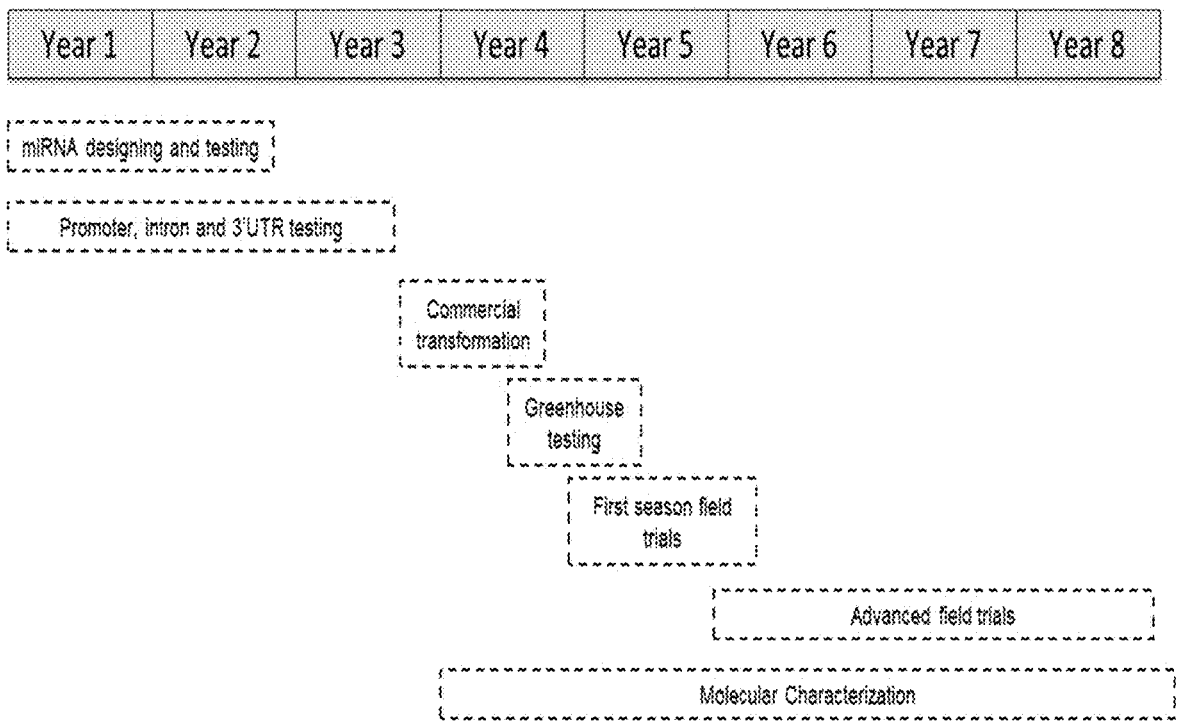
FIG. 4 represents the approximate timing of creation, testing, characterization, and selection of the ZM_BCS216090 corn event as described herein.

The following examples are included to more fully describe the invention. Summarized are the production and testing of over fifteen thousand (15,000) unique events for miRNA transgenic construct pM578, and the analysis of hundreds of thousands of individual plants over seven years through the rigorous molecular, agronomic, and field testing required for the creation and ultimate selection of corn lead event ZM_BCS216090 (see, e.g., FIG. 4 and FIG. 5).

While the Examples demonstrate certain embodiments of the present invention, it should be appreciated that all specific embodiments and examples provided herein are illustrative and not exhaustive. Those of skill in the art should, in light of the present disclosure, appreciate that changes and modifications can be made to the embodiments, examples and details that are disclosed herein without departing from the spirit and scope of the present invention.

Example 1

Expression Cassette Testing, Construct Design, Plant Testing, and Construct Selection Transgene expression in plants is influenced by numerous different factors. The right combination of a gene of interest (GOI) and different expression elements driving expression in plants must be found, while not resulting in off-phenotypes that have deleterious traits. Further, beyond the expression elements themselves and their combination and orientation in a cassette, the expression of transgenes in plants can be influenced by chromosomal insertion position, perhaps due to chromatin structure (e.g., heterochromatin) or the proximity of transcriptional regulation elements (e.g., enhancers, etc.) close to the integration site (Kurt Weising et al., *Annu. Rev. Genet.* 22:421-77, 1988). For example, there can be variation in the levels of expression of an introduced gene from the same construct among different events with different chromosomal insertion positions in the plant genome. Different chromosomal insertion positions may also produce differences in spatial or temporal patterns of expression that may not correspond to the patterns expected from transcriptional regulatory elements present in the introduced gene construct.

For these reasons, it is often necessary to create and screen multiple constructs and a large number of transformation events for a given construct in order to identify the construct, and then the optimal event (the lead event), which demonstrates optimal traits and suitable expression of the introduced gene of interest along with an absence of molecular and genomic insertion concerns (e.g., selecting clean insertions without transgene truncations or extraneous vector sequence and avoiding insertion positions that are near existing genes, loci or transgenes of interest), while also not producing agronomic or phenotypic off-types. Prior to such studies, it may not be possible to determine whether a particular beneficial event phenotype can be obtained or which event will provide these optimal traits and characteristics. In an initial proof of concept and developmental stage over several years and multiple growing seasons, a number of different constructs with different expression elements were transformed into corn plants. The transformed plants were tested and selected progressively for subsequent testing, based on a desirable range of reduced plant height and ear height, and absence of phenotypic and agronomic off-types. The resulting leading construct, designated pM578 (see FIG. 2), was chosen for extensive further transformation event testing.

*Agrobacterium tumefaciens* (AB32 strain) cells carrying construct pM578, which contains the CP4 EPSPS gene as a selectable marker and a transgenic miRNA gene (the transgene), were used in plant transformation of an elite corn line designated "EL0" to generate short stature corn plants comprising the transgene. A total of 1,533 transgenic plants were obtained from *Agrobacterium*-mediated transformation of wild-type embryo explants using the *Agrobacterium tumefaciens* AB32 strain cells carrying the pM578 vector or plasmid construct.

The transgenic plants were subjected to a series of molecular screenings and agronomic field trials to identify backbone-free events carrying a single copy of the intact T-DNA. A superior event was then selected as a lead candidate based on the molecular data and agronomic phenotypes.

For molecular quality control (MQC) screening, three TaqMan quantitative PCR assays were utilized for genotyping, to detect the presence and copy number of the gene of interest (GOI), selection marker, and backbone. Events with one copy of GOI, one copy of marker but no backbone passed MQC screenings. Events with more than one copy of the GOI or marker or that were backbone positive did not pass the MQC screenings. If events had inconclusive results from any one of the assays, they were classified as uncallable and excluded from further evaluations.

Figure 5:
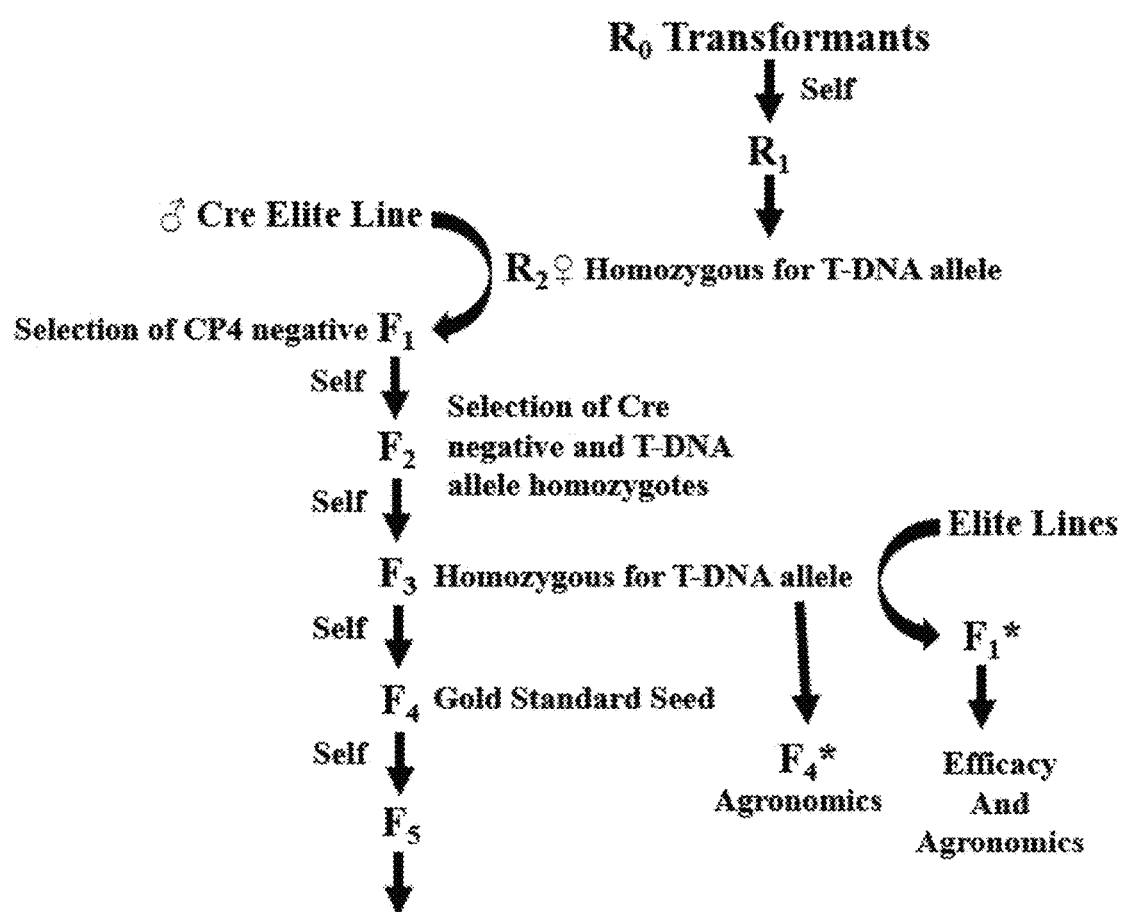
FIG. 5 is a diagrammatic representation of the breeding process to produce the marker-free corn event ZM_BCS216090. $R_0$ generation events ("transformants") are those that are derived from the initial transformation with the transformation vector used to generate corn event ZM_BCS216090. Subsequent "R" generations ($R_1$, and $R_2$) represent successive generations produced through self-pollination of plants derived from the initial $R_0$ transformant that resulted in corn event ZM_BCS216090. The $R_2$ transformants, which are homozygous for the T-DNA insertion, are cross-pollinated with an elite transgenic corn line comprising a transgene cassette for the expression of Cre-recombinase, resulting in an $F_1$ generation, wherein many of the progeny have lost the CP4 EPSPS selectable marker cassette due to Cre-recombinase excision. Hemizygous T-DNA positive, CP4 EPSPS negative plants are selected and self-pollinated, resulting in an $F_2$ generation. $F_2$ plants homozygous for the inserted T-DNA without the CP4 EPSPS marker gene and lacking the Cre-recombinase transgene cassette are selected and self-pollinated giving rise to an $F_3$ generation. The $F_3$ generation plants are self-pollinated giving rise to a pure line of $F_4$ Gold Standard Seed.
Figure 6:
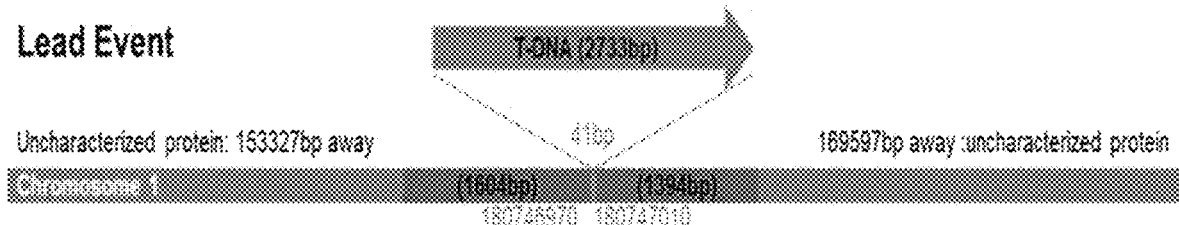
FIG. 6 shows a representation of the insertion site of corn event ZM_BCS216090 relative to the endogenous corn genome on chromosome 1.

From the 1,533 transgenic plants, 225 events (15%) that were backbone-free and carrying only a single copy of the insertion in plants were identified through $R_0$ MQC screenings. FIG. 5 shows an illustration of the full breeding process used to generate and select the marker-free ZM_BCS216090 corn event. $R_0$ MQC screening results indicated that the precursor event for corn event ZM_BCS216090 (prior to Cre marker excision—see below), later selected as the lead event, had one copy of the CP4 EPSPS marker gene and the transgene, but no backbone of the transformation vector.

Table 2 illustrates that of these one-copy and backbone-free events, 80 events (36%) and 15 events (7%) were discarded for off-type phenotypes or plant health, respectively, while 130 events (58%) passed MQC screening and R0 plants with these events were grown to maturity. The numbers of events advanced to each successive generation are pooled across multiple rounds of transformations.

TABLE 2

| Breakdown of corn $R_0$ transgenic plants. | | |
| --- | --- | --- |
| Description | Number | Percentage |
| Total events generated | 1,533 | 100% |
| Did not pass MQC screenings | 1,293 | 84% |
| Uncallable | 15 | 1% |
| Passed MQC screenings | 225 | 15% |
| Discarded-off phenotypes | 80 | 35% |
| Discarded-poor plant health | 15 | 7% |
| Passed MQC Ro Screening | 130 | 58% |

The transgenic plants were subjected to additional molecular screenings, such as whole genome sequencing (E-Southern), to determine the sequence and genomic context for the $R_0$ events that were grown to maturity, and 84 of those events were selected and selfed to produce $R_1$ seed based on these additional genomic considerations. Based on sequence information mapped against the genomes of B73 and in-house elite lines, the genomic location of the in planta T-DNA insertion was identified on chromosome 1 with a deletion of 41 base pairs in the genome at the site of insertion.

$R_1$ MQC screening was performed to confirm that individual events in the $R_0$ plants were present in a single copy and segregated in an expected 1:2:1 ratio (homozygotes:hemizygotes:wild-type nulls). For example, as shown in Table 3, $R_1$ MQC screening results for the precursor event to corn event ZM_BCS216090 (prior to Cre marker excision) showed the 1:2:1 segregation for both the CP4-EPSPS and the miRNA encoding transgene. Homozygous $R_1$ plants for selected events were selfed to produce $R_2$ plants, and $R_2$ MQC screening was performed to confirm that all $R_2$ offspring derived from the $R_1$ homozygous plants were also homozygous for the respective event. For example, as shown in Table 4, $R_2$ MQC screening results for the precursor event to corn event ZM_BCS216090 (prior to Cre marker excision) revealed that all $R_2$ plants from the were homozygous for both the CP4-EPSPS and the miRNA encoding transgene, confirming again that the T-DNA insertion was a single copy in the lead event. From the 84 selected events at the $R_0$ stage that were selfed to produce $R_1$ seed, 66 events were selected and selfed in $R_1$ plants to produce homozygous $R_2$ seeds. Selection and attrition in the numbers of events advanced to each subsequent generation was due to multiple factors including, for example, seed availability and limited capacity.

TABLE 3

R$_1$ MQC screening results for precursor of corn event ZM_BCS216090.

| Zygosity | Corn Event ZM_BCS216090 (count and %) | |
| --- | --- | --- |
| Homozygotes | 5 | 23% |
| Hemizygotes | 12 | 55% |
| Wild-type (nulls) | 5 | 23% |

Note:

The calls for both the CP4 EPSPS and the miRNA transgene gene were the same for each plant.

TABLE 4

R$_2$ MQC screening results for precursor of corn event ZM_BCS216090.

| Zygosity | Corn Event ZM_BCS216090 (count and %) | |
| --- | --- | --- |
| Homozygotes | 73 | 100% |
| Hemizygotes | 0 | 0% |
| Wild-type (nulls) | 0 | 0% |

Note:

Three batches of genotyping data were combined. The calls for both the CP4 EPSPS and the miRNA transgene were the same for each plant.

Example 2

Cre-Excision of the Glyphosate Selection Cassette in Corn Event ZM_BCS216090

This example describes the removal of the glyphosate selection cassette from corn event ZM_BCS216090 through in planta Cre-excision. The glyphosate selection cassette was used to select transformed events. By removal of the selection cassette, a "marker-free" event was created wherein only the transgenic miRNA expression cassette remained in the final event.

FIG. 5 illustrates the breeding process used to generate the marker-free ZM_BCS216090 corn event. Construct pM578 comprises the miRNA expression cassette and a cassette used for the selection of transformed plant cells using glyphosate selection. The selection cassette was flanked on both sides with LoxP Cre-recombinase recognition sites. As described above, elite corn line embryo explants were transformed using an *Agrobacterium*-mediated transformation process with construct pM578. After transformation, the R$_0$ transformants were self-pollinated for two (2) generations, during which time many events were removed based on various assays and normal attrition as mentioned above, such as seed return, plant health, and molecular characterization. At this stage, plants in the R$_2$ generation comprising a transgenic event were bred with plants expressing Cre-recombinase as shown in FIG. 5. Specifically, de-tasseled (female) R$_2$ generation plants homozygous for the miRNA expression cassette were cross-pollinated with transgenic corn (male) plants homozygous for a transgene cassette encoding a Cre-recombinase enzyme. The Cre-recombinase expressing male donor pollen germinates after landing on the silk tissue of the female plant comprising the miRNA expression cassette, setting free the two sperms of the Cre-recombinase expressing male donor. The nucleus of one sperm fuses with an egg nucleus of the female plant forming a zygote, and the other sperm nucleus fuses with one of the two polar nuclei which in turn fuses with the other polar nucleus, thereby establishing the primary endosperm nucleus. Thus, by using the Cre-recombinase expressing plant as the male pollen donor, both the embryo and endosperm of the resulting cross will express Cre-recombinase as the cells divide and develop and become a corn kernel (i.e. seed). The Cre-recombinase binds to inverted repeats in the LoxP site and catalyzes a crossover in an eight-base pair spacer region of the two LoxP sites that flank the expression cassette, resulting in the excision of the marker cassette with one LoxP site remaining in the integrated T-DNA due to recombination.

As shown in FIG. 5, R$_2$ plants for 43 events were crossed to plants expressing the Cre recombinase (Cre Elite Line). F$_1$ progeny resulting from this cross were selected for the absence of the CP4 EPSPS selection cassette, and F$_1$ progeny for 38 marker-free events were allowed to self-pollinate to produce F$_2$ progeny plants. This self-pollination of F$_1$ progeny is identified as the F$_1$ Self in the timeline presented in FIG. 5. Through this process, the two remaining expression cassettes—the Cre-recombinase expression cassette and the miRNA encoding transgene—segregated in the resulting F$_2$ population, resulting in progeny homozygous or heterozygous for one or both expression cassettes or transgenes.

F$_2$ progeny were selected that demonstrated the absence of the Cre-recombinase expression cassette and homozygosity for the transgenic miRNA expression cassette without the marker cassette. These selected F$_2$ progeny for 23 events were self-pollinated (identified as the F$_2$ Self in the timeline presented in FIG. 5), giving rise to an F$_3$ generation homozygous for the miRNA expression cassette. In addition to the absence of the Cre-recombinase cassette and homozygosity of the transgene, the events for the F$_2$ Self were also selected based on additional genomic, trait integration and breeding considerations.

A further self-pollination of F$_3$ progeny for 22 events (identified as the F$_3$ Self in the timeline presented in FIG. 5) was performed to produce F$_4$ progeny and seed which were assayed for purity and were designated as "Gold Standard Seed" (or "GSS"). Gold Standard Seed is seed that has been assayed for purity to assure the absence of transgenic events other than corn event ZM_BCS216090. F$_4$ was the first generation of Gold Standard Seed. After creation of the of the GSS, F$_4$ progeny plants for only 10 events were selected and further self-pollinated to produce additional generations of progeny plants and seed homozygous for the miRNA expression cassette or transgene, or alternatively progeny plants homozygous for the miRNA expression cassette or transgene from the F$_4$ or subsequent generations may be crossed to other plants having a different genotype or germplasm, such as to allow for trait integration of an event described herein, such as corn event ZM_BCS216090, in other germplasms or genetic backgrounds and/or with other traits.

Excision of the glyphosate selection marker cassette did not affect the transgene expression. Removing the glyphosate selection cassette from corn event ZM_BCS216090 through Cre-excision provided a transgenic corn event which produced short stature corn plants without the CP4 EPSPS cassette in the final event. This "marker-free" event assures flexibility when building corn breeding stacks with other corn transgenic events to provide a multiplicity of products incorporating corn event ZM_BCS216090 and allowing multiple options for providing additional traits in final commercial breeding stacks.

Example 3

Corn Event ZM_BCS216090 Event-Specific Endpoint TaqMan® Assays

The following example describes methods useful in identifying the presence of corn event ZM_BCS216090 in a corn sample.

Detection of corn event ZM_BCS216090 in a sample can be done using DNA- or RNA-based detection techniques. Exemplary detection methods and materials are provided herein. Detection may determine the presence or absence of the event in a sample. Detection may also indicate the number of genomic copies of corn event ZM_BCS216090 (that is, hemizygous, homozygous, or heterozygous) in a sample of genomic DNA.

An event-specific endpoint Applied Biosystems™ TaqMan thermal amplification method (Thermo Fisher Scientific) was developed to identify corn event ZM_BCS216090 in a sample. The DNA primers and probe used in the endpoint assay for this example are shown in Table 5, although it is appreciated that other primers and probes may also be used.

TABLE 5

ZM_BCS216090 event-specific and internal control primers and probes.

| SEQ ID NO. | Name | Type |
|---|---|---|
| 11 | Primer SQ51606 | Event-specific |
| 12 | Primer SQ51629 | Event-specific |
| 13 | 6FAM ™ probe PB50583 | Event-specific |
| 14 | Primer SQ20222 | Internal control |
| 15 | Primer SQ20221 | Internal control |
| 16 | VIC ® Probe PB50298 | Internal control |

6-FAM is a fluorescent dye product of Applied Biosystems (Foster City, CA) and is attached to the DNA probe. For TaqMan MGB probes, the 5' exonuclease activity of Taq DNA polymerase cleaves the probe from the 5'-end, between the fluorophore and quencher. When hybridized to the target DNA strand, quencher and fluorophore are separated enough to produce a fluorescent signal, thus releasing fluorescence. The pair of primers when used with these reaction methods and the probe produce a DNA amplicon that is diagnostic for corn event ZM_BCS216090. The controls for this analysis should include a positive control containing corn event ZM_BCS216090, a negative control from non-transgenic plant, and a negative control that contains no template DNA. Additionally, a control for the PCR reaction should optimally include internal control primers and an internal control probe, specific to a single copy gene in the corn genome. These assays are optimized for use with the Applied Biosystems GeneAmp® PCR System 9700 (Thermo Fisher Scientific) run at maximum speed, but other equipment may be used.

Event-specific PCR assays for line identification (Line ID) were developed and validated. Based on integrated T-DNA and flanking genomic sequences, TaqMan PCR assays were designed. Simplified validation (sValid) tests were conducted to identify good assays by running endpoint PCR on replicates of 8 positive, 6 negative, and 2 water samples. Scores were calculated based on the difference of FAM readings, using the formula defined as score=(average of positive samples−average of negative samples). Assay performance was ranked based on the score in a five-star system, an assay with three or more stars being considered acceptable. A purity test was performed to ensure that leaf tissues containing target sequences show the positive for corresponding assays. A proficiency test (PT) was conducted to ensure that the procedure can be replicated to obtain the expected results with the assay.

Event-specific endpoint TaqMan PCR assays (Line IDs) are used for GSS nurseries and other quality screening programs to verify the presence of traits of interest. Based on plant flanking sequences and the in planta T-DNA sequences identified by $R_0$ rapid unlinked sequence hybridization (RUSH), two line IDs, which incorporate a transgene oligonucleotide, a corresponding second oligonucleotide appropriately positioned in either the 5' or 3' flanking sequence and a fluorescently labeled probe, for the lead event were designed and validated.

The line ID assay that has been selected and used in subsequent molecular characterizations for corn event ZM_BCS216090 is an event-specific qualitative endpoint TaqMan PCR assay. Setup and sequence information for the corn event ZM_BCS216090 line ID assay are listed in Table 6, and cycling conditions are presented in Table 7.

TABLE 6

ZM_BCS216090 event-specific endpoint TaqMan PCR reaction components.

| Step | Reagent | Stock Concentration (µM) | Volume (µl) | Final Concentration (µM) | Comments |
|---|---|---|---|---|---|
| — | Reaction Volume | | 5 | | |
| 1 | 18 megohm water | | 0.00 | | Adjust for final volume |
| 2 | 2 × Master Mix | | 2.28 | | 1 × final concentration of buffer |
| 3 | Event Specific Primer SQ51606 | 100 | 0.05 | 0.9 | |
| 4 | Event Specific Primer SQ51629 | 100 | 0.05 | 0.9 | |
| 5 | Event Specific 6FAM™M probe PB50583 | 100 | 0.01 | 0.2 | Probe is light sensitive |
| 6 | Internal Control Primer SQ20222 | 100 | 0.05 | 0.9 | |
| 7 | Internal Control Primer SQ20221 | 100 | 0.05 | 0.9 | |
| 8 | Internal Control VIC® Probe PB50298 | 100 | 0.01 | 0.2 | Probe is light sensitive |

TABLE 6-continued

ZM_BCS216090 event-specific endpoint TaqMan PCR reaction components.

| Step | Reagent | Stock Concentration (µM) | Volume (µl) | Final Concentration (µM) | Comments |
|------|---------|--------------------------|-------------|--------------------------|----------|
| 9 | Extracted DNA (template): Leaf Samples to be analyzed Negative control (non-transgenic DNA) Negative water control (No template control) Positive Qualitative control(s) ZM_BCS216090 DNA | | 2.5 | | Separate reactions are made for each template. |

TABLE 7

Endpoint TaqMan thermocycler conditions.

| Step No. | Cycle No. | Settings |
|----------|-----------|----------|
| 1 | 1 | 95° C., 20 seconds |
| 2 | 35 | 95° C., 3 seconds |
|   |   | 60° C., 20 seconds |
| 3 | 1 | 10° C. |

A zygosity assay is described here to determine whether a plant comprising the lead event is heterozygous or homozygous for the event or the wild-type sequence. An amplification reaction assay can be designed using the sequence information provided herein. For example, such a PCR assay would include design of at least three primers: primer-1, primer-2, and primer-3, where primer-1 is specific to the genomic DNA on the 3' flank of the lead event; primer-2 is specific to the lead event transgenic insert; and primer-3 is specific to the wild-type sequence. When used as a primer pair in an amplification reaction, primer-1 with primer-2 will produce a PCR amplicon specific for the lead event. When used as a primer pair in an amplification reaction, primer-1 with primer-3 will produce a PCR amplicon specific for wild-type sequence. In a PCR reaction performed on corn genomic DNA, the respective PCR amplicons generated from primer-1+primer-2 and that generated from primer-1+primer-3 will differ in sequence and size of the amplicon. When the three primers are included in a PCR reaction with DNA extracted from a plant homozygous for the lead event, only the primer-1+primer-2 amplicon (specific for the lead event insertion) will be generated. When the three primers are included in a PCR reaction with DNA extracted from a plant heterozygous for the lead event, both the primer-1+primer-2 amplicon (specific for the lead event insertion) and the primer-1+primer-3 amplicon (specific for wild-type sequence or absence of the lead event insertion) will be generated. When the three primers are mixed together in a PCR reaction with DNA extracted from a plant that is null for the lead event (wild-type), only the primer-1+primer-3 amplicon (specific for wild-type sequence) will be generated. The amplicons produced using the PCR reaction may be identified or distinguished using any method known in the art.

Another zygosity assay for the lead event is a TaqMan thermal amplification reaction. For this type of assay, in addition to primers as described above, the assay would include two fluorescently labeled probes. Probe-1 would be specific for the lead event, and probe-2 would be specific for a corn plant that is null for the lead event (wild-type), and where the two probes contain different fluorescent labels, for example the 6-FAM-label or VIC-label. When used in a TaqMan reaction, primer-1+primer-2+probe-1 will produce a first fluorescent signal specific for the lead event and primer-1+primer-3+probe-2 will produce a second fluorescent signal specific for a wild-type plant. When the three primers and two probes are included in a TaqMan reaction with DNA extracted from a plant homozygous for the lead event, only the first fluorescent signal (specific to primer-1+primer-2+probe-1) will be generated. When the three primers and two probes are included in a TaqMan reaction with DNA extracted from a plant heterozygous for the lead event, both the first fluorescent signal (specific to primer-1+primer-2+probe-1) and the second fluorescent signal (specific to primer-1+primer-3+probe-2) will be generated. When the three primers are mixed together in a TaqMan reaction with DNA extracted from a plant which is null for the lead event (wild-type), only the second fluorescent signal (specific to primer-1+primer-3+probe-2) will be generated.

Another method to detect the presence of the lead event in a plant sample would be Southern analysis as generally understood in the art. One of skill in art, based on the present disclosure and description of the lead event, would understand how to design Southern hybridization probe(s) specific for the lead event and a second southern hybridization probe specific for a plant which is null for the lead event (wild-type). With Southern analysis, a signal detected only from the first Southern hybridization probe will be indicative of a plant homozygous for the lead event; a signal detected from both the first Southern hybridization probe and the second Southern hybridization probe will be indicative of a plant heterozygous for the lead event; and a signal detected only from the second Southern hybridization probe will be indicative that the DNA was extracted from a plant that is null for the lead event (wild-type).

Example 4

Yield and Agronomic Traits of Corn Event ZM_BCS216090 Based on Field Trials in Multiple Growing Seasons This example demonstrates that transgenic corn event ZM_BCS216090 minimizes crop yield losses for farmers though improved standability and increased lodging resistance due to its short stature or semi-dwarf phenotype. In addition, the reduced stature of corn plants comprising event ZM_BCS216090 enables season-long field access which leads to improved precision of crop input and sustainability. Inbreds for these field studies (designated as the $F_4$* generation in FIG. 5) were made by selfing $F_3$ plants having the same 10 events that were advanced as GSS in $F_4$ and subsequent generations, and hybrids for these field studies were made by crossing $F_3$ plants having the same 10 events with four other elite lines (EL1-4) that lack the transgene to produce $F_1$* progeny plants (the "*" is intended to distinguish the $F_1$ and $F_4$ generations for marker excision and generating gold standard seed; $F_3$ plants comprising each of the events and isogenic control plants lacking any transgenic event were each designated as elite line 0 or EL0 in the hybrid crosses).

In consecutive years, transgenic plants comprising each of the 10 events selected for GSS, including corn event ZM_BCS216090 and 9 other events (designated Events 2-9), were tested in the field across 34 locations in agronomic yield trials across U.S. Midwestern states. Compared to untransformed control plants, hybrid plants comprising corn event ZM_BCS216090 demonstrated consistent yields, reduced plant height and increased lodging resistance, and inbred plants comprising corn event ZM_BCS216090 showed reduced plant height and consistent flowering.

Measurements of yield were calculated by adjusting for moisture and expressed as bushels per acre (bu/acre). Plant height is measured as the distance in inches (in) from the soil line to the collar of the flag leaf. Ear height is measured as the distance in inches between the soil line and the primary ear node. Measurements of lodging is expressed as the percentage of plants with a plot leaning 30 degrees or more from perpendicular. Fifty percent (50%) pollen shed and fifty percent (50%) silking were expressed as days after planting (DAP).

Table 8 shows the yield and agronomic characteristics measured for corn event ZM_BCS216090 hybrids. Table 9 shows the agronomic characteristics measured for corn event ZM_BCS216090 inbreds produced by selfing the transformed EL0 line. Inbred lines containing event ZM_BCS216090 or each of Events 2-9 were compared to the non-transformed control of the self-crossed EL0 line, and hybrid lines containing event ZM_BCS216090 or each of Events 2-9 and crossed to each of EL1-EL4 were compared to the non-transformed control hybrids of the same cross. The mean measurements and standard error (SE) are reported in the tables.

TABLE 8

Yield and agronomics for event ZM_BCS216090 hybrids relative to non-transgenic controls in year one of field testing.

| | Plant Height (in) | | Ear Height (in) | | Yield (bu/acre) | | Root Lodging % | |
|---|---|---|---|---|---|---|---|---|
| | Mean | SE | Mean | SE | Mean | SE | Mean | SE |
| ZM_BCS216090 EL0 × EL1 | 63.51 | 1.25 | 24.85 | 0.77 | 240.46 | 6.13 | 4.20 | 8.17 |
| ZM_BCS216090 EL0 × EL2 | 62.84 | 1.25 | 26.74 | 0.77 | 234.10 | 6.16 | 10.47 | 8.20 |
| ZM_BCS216090 EL0 × EL3 | 61.64 | 1.25 | 25.08 | 0.77 | 240.64 | 6.15 | 12.18 | 8.17 |
| ZM_BCS216090 EL0 × EL4 | 62.29 | 1.25 | 24.81 | 0.77 | 244.86 | 6.12 | 12.64 | 8.17 |
| Event 2 EL0 × EL1 | 62.81 | 1.25 | 24.67 | 0.77 | 234.65 | 6.14 | 2.88 | 8.20 |
| Event 2 EL0 × EL2 | 61.78 | 1.25 | 26.22 | 0.77 | 228.82 | 6.14 | 9.82 | 8.17 |
| Event 2 EL0 × EL3 | 60.76 | 1.25 | 25.41 | 0.77 | 236.36 | 6.13 | 10.00 | 8.17 |
| Event 2 EL0 × EL4 | 61.47 | 1.25 | 24.80 | 0.77 | 235.27 | 6.14 | 12.30 | 8.20 |
| Event 3 EL0 × EL1 | 62.52 | 1.25 | 24.22 | 0.77 | 234.98 | 6.14 | 0.98 | 8.20 |
| Event 3 EL0 × EL2 | 61.32 | 1.25 | 26.40 | 0.77 | 231.41 | 6.14 | 7.04 | 8.17 |
| Event 3 EL0 × EL3 | 59.93 | 1.25 | 24.43 | 0.77 | 236.94 | 6.15 | 9.62 | 8.25 |
| Event 3 EL0 × EL4 | 60.91 | 1.25 | 24.73 | 0.77 | 239.70 | 6.13 | 13.29 | 8.20 |
| Event 4 EL0 × EL1 | 61.90 | 1.25 | 23.87 | 0.77 | 232.53 | 6.12 | 1.54 | 8.20 |
| Event 4 EL0 × EL2 | 60.58 | 1.25 | 25.66 | 0.77 | 228.24 | 6.14 | 5.50 | 8.17 |
| Event 4 EL0 × EL3 | 58.56 | 1.25 | 24.17 | 0.77 | 232.67 | 6.14 | 7.96 | 8.17 |
| Event 4 EL0 × EL4 | 60.63 | 1.25 | 24.18 | 0.77 | 235.62 | 6.14 | 10.80 | 8.20 |
| Event 5 EL0 × EL1 | 62.85 | 1.25 | 24.71 | 0.77 | 236.29 | 6.11 | 2.84 | 8.17 |
| Event 5 EL0 × EL2 | 60.90 | 1.25 | 25.93 | 0.77 | 227.79 | 6.13 | 7.07 | 8.17 |
| Event 5 EL0 × EL3 | 59.75 | 1.25 | 24.65 | 0.77 | 238.91 | 6.14 | 10.81 | 8.17 |
| Event 5 EL0 × EL4 | 61.11 | 1.25 | 24.72 | 0.77 | 237.32 | 6.12 | 12.67 | 8.20 |
| Event 6 EL0 × EL1 | 62.60 | 1.25 | 24.74 | 0.77 | 235.61 | 6.14 | 3.14 | 8.17 |
| Event 6 EL0 × EL2 | 61.80 | 1.25 | 26.20 | 0.77 | 225.95 | 6.13 | 8.07 | 8.17 |
| Event 6 EL0 × EL3 | 59.80 | 1.25 | 24.73 | 0.77 | 236.20 | 6.13 | 7.44 | 8.17 |
| Event 6 EL0 × EL4 | 60.83 | 1.25 | 24.83 | 0.77 | 238.59 | 6.14 | 10.01 | 8.20 |
| Event 7 EL0 × EL1 | 63.00 | 1.25 | 24.17 | 0.77 | 234.18 | 6.14 | 2.31 | 8.17 |
| Event 7 EL0 × EL2 | 61.51 | 1.25 | 25.99 | 0.77 | 225.86 | 6.14 | 9.60 | 8.17 |
| Event 7 EL0 × EL3 | 60.38 | 1.25 | 24.70 | 0.77 | 238.15 | 6.13 | 12.23 | 8.17 |
| Event 7 EL0 × EL4 | 61.41 | 1.25 | 25.27 | 0.77 | 237.34 | 6.13 | 12.99 | 8.20 |
| Event 8 EL0 × EL1 | 62.43 | 1.25 | 24.59 | 0.77 | 239.77 | 6.14 | 2.98 | 8.20 |
| Event 8 EL0 × EL2 | 61.97 | 1.25 | 26.29 | 0.77 | 231.32 | 6.13 | 6.33 | 8.17 |
| Event 8 EL0 × EL3 | 59.97 | 1.25 | 24.52 | 0.77 | 237.51 | 6.14 | 9.86 | 8.20 |
| Event 8 EL0 × EL4 | 61.42 | 1.24 | 24.71 | 0.77 | 240.74 | 6.13 | 13.82 | 8.17 |
| Event 9 EL0 × EL1 | 62.05 | 1.25 | 23.69 | 0.77 | 231.46 | 6.14 | 4.03 | 8.17 |
| Event 9 EL0 × EL2 | 61.43 | 1.25 | 26.29 | 0.77 | 229.36 | 6.15 | 8.47 | 8.20 |
| Event 9 EL0 × EL3 | 60.50 | 1.25 | 24.71 | 0.77 | 237.99 | 6.12 | 7.92 | 8.20 |
| Event 9 EL0 × EL4 | 60.81 | 1.25 | 24.72 | 0.77 | 237.72 | 6.15 | 10.16 | 8.20 |

TABLE 8-continued

Yield and agronomics for event ZM_BCS216090 hybrids relative
to non-transgenic controls in year one of field testing.

|  | Plant Height (in) | | Ear Height (in) | | Yield (bu/acre) | | Root Lodging % | |
|---|---|---|---|---|---|---|---|---|
|  | Mean | SE | Mean | SE | Mean | SE | Mean | SE |
| Control EL0 × EL1 | 95.48 | 1.24 | 44.26 | 0.74 | 230.62 | 5.96 | 9.50 | 8.01 |
| Control EL0 × EL2 | 96.78 | 1.24 | 46.78 | 0.74 | 227.92 | 5.97 | 11.76 | 8.00 |
| Control EL0 × EL3 | 92.84 | 1.24 | 43.69 | 0.74 | 231.94 | 5.97 | 18.15 | 8.00 |
| Control EL0 × EL4 | 98.59 | 1.24 | 46.66 | 0.74 | 234.87 | 5.96 | 26.48 | 8.01 |

TABLE 9

Agronomics for event ZM_BCS216090 inbreds relative
to non-transgenic controls in year one.

|  | Plant Height (in) | | Ear Height (in) | | 50% Pollen Shed (DAP) | | 50% Silking (DAP) | |
|---|---|---|---|---|---|---|---|---|
|  | Mean | SE | Mean | SE | Mean | SE | Mean | SE |
| ZM_BCS216090 | 61.17 | 3.07 | 19.92 | 0.93 | 64.10 | 3.70 | 64.60 | 3.45 |
| Event 2 | 59.33 | 3.07 | 20.08 | 0.93 | 64.50 | 3.70 | 64.70 | 3.45 |
| Event 3 | 57.76 | 3.09 | 18.33 | 0.93 | 63.20 | 3.70 | 63.60 | 3.45 |
| Event 4 | 57.50 | 3.07 | 18.50 | 0.93 | 63.60 | 3.70 | 64.00 | 3.45 |
| Event 5 | 58.91 | 3.10 | 19.83 | 1.00 | 63.70 | 3.70 | 64.40 | 3.45 |
| Event 6 | 59.42 | 3.07 | 19.17 | 0.93 | 63.80 | 3.70 | 64.70 | 3.45 |
| Event 7 | 59.72 | 3.09 | 18.56 | 0.97 | 63.80 | 3.70 | 64.70 | 3.45 |
| Event 8 | 58.42 | 3.07 | 18.75 | 0.93 | 64.00 | 3.70 | 64.30 | 3.45 |
| Event 9 | 57.33 | 3.07 | 17.83 | 0.93 | 63.20 | 3.70 | 63.50 | 3.45 |
| Control | 83.32 | 2.97 | 32.88 | 0.70 | 63.77 | 3.69 | 64.77 | 3.44 |

As can be seen in Table 8, the measures of yield were relatively the same or better for corn event ZM_BCS216090 hybrids relative to the respective controls, and plant height, ear height, and lodging were reduced relative to the respective hybrid controls. Increases in yield in hybrids comprising corn event ZM_BCS216090 in comparison to the respective controls may be due to the reduced root lodging. Additionally, Table 9 demonstrates that timing of 50% pollen shed and 50% silking is relatively similar for inbred plants comprising corn event ZM_BCS216090 when compared to the inbred control plants, and plant height and ear height are reduced relative to the inbred control.

During the subsequent year of testing, field trials were conducted using hybrids comprising corn event ZM_BCS216090 and the other 9 events (Events 2-9) in comparison to non-transformed hybrid controls. Table 10 shows that the yield of corn event ZM_BCS216090 hybrids was generally similar to or better than the yields observed in control plants, while plant height, ear height, and root lodging were decreased in plants comprising event ZM_BCS216090 when compared to the respective controls. A decrease in root lodging may at least partly explain any observed yield improvement in plants comprising event ZM_BCS216090 compared to the control plants.

TABLE 10

Yield and agronomics for event ZM_BCS216090 hybrids relative
to non-transgenic controls (year two growing season).

|  | Plant Height (in) | | Ear Height (in) | | Yield (bu/acre) | | Root Lodging % | |
|---|---|---|---|---|---|---|---|---|
|  | Mean | SE | Mean | SE | Mean | SE | Mean | SE |
| ZM_BCS216090 × EL1 | 66.69 | 1.40 | 26.27 | 0.75 | 219.84 | 6.10 | 13.11 | 13.38 |
| ZM_BCS216090 × EL2 | 67.06 | 1.40 | 27.80 | 0.75 | 218.60 | 6.12 | 17.25 | 13.41 |
| ZM_BCS216090 × EL3 | 64.72 | 1.40 | 25.42 | 0.75 | 218.51 | 6.13 | 21.00 | 13.38 |
| ZM_BCS216090 × EL4 | 68.21 | 1.40 | 25.94 | 0.75 | 227.96 | 6.14 | 10.16 | 13.38 |
| Control EL0 × EL1 | 99.34 | 1.40 | 45.51 | 0.75 | 215.76 | 6.15 | 31.68 | 12.85 |
| Control EL0 × EL2 | 100.92 | 1.40 | 48.66 | 0.75 | 215.35 | 6.18 | 42.32 | 12.87 |
| Control EL0 × EL3 | 95.98 | 1.40 | 44.95 | 0.75 | 212.89 | 6.19 | 45.53 | 12.85 |
| Control EL0 × EL4 | 103.11 | 1.40 | 48.18 | 0.75 | 215.97 | 6.15 | 40.46 | 12.85 |

To summarize the observations from two consecutive years of field trials, plants comprising corn event ZM_BCS216090 demonstrate similar or better hybrid yield, similar inbred flowering, and reduced plant height and lodging when compared to non-transformed controls.

---

What is claimed is:

1. A recombinant DNA molecule comprising a nucleotide sequence selected from the group consisting of SEQ ID NO: 1, SEQ ID NO: 3, SEQ ID NO: 5, SEQ ID NO: 7, and a complete complement thereof.

2. The recombinant DNA molecule of claim 1, wherein the recombinant DNA molecule is:

(a) derived from a transgenic corn plant comprising corn event ZM_BCS216090, a representative sample of seed comprising said event having been deposited under ATCC Accession No. PTA-127050;

(b) comprised in a corn plant, plant cell, seed, progeny plant, plant part, or commodity product;

(c) formed by the insertion of a heterologous nucleic acid molecule into the genomic DNA of a corn plant or corn cell; or (d) an amplicon diagnostic for the presence of DNA derived from corn event ZM_BCS216090.

3. A DNA molecule comprising a polynucleotide segment of sufficient length to function as a DNA probe that hybridizes specifically under stringent hybridization conditions with corn event ZM_BCS216090 DNA, a representative sample of seed comprising said event having been deposited under ATCC Accession No. PTA-127050, in a sample, wherein detecting hybridization of said DNA molecule under said stringent hybridization conditions is diagnostic for the presence of corn event ZM_BCS216090 DNA in said sample, wherein the DNA molecule comprises the nucleotide sequence of SEQ ID NO:1 or a complete complement thereof.

4. The DNA molecule of claim 3, wherein:

said sample is derived from a corn plant, corn plant cell, corn seed, corn plant part, corn progeny plant, processed corn seed, animal feed comprising corn, corn oil, corn meal, corn flour, corn flakes, corn bran, pasta made with corn, corn biomass, and fuel products produced using corn and corn parts.

5. A method of detecting the presence of a DNA segment diagnostic for corn event ZM_BCS216090 DNA in a sample, said method comprising:

a) contacting said sample with the DNA molecule of claim 3;

b) subjecting said sample and said DNA molecule to stringent hybridization conditions; and c) detecting hybridization of said DNA molecule to said DNA in said sample, wherein said detection is diagnostic for the presence of said corn event ZM_BCS216090 DNA in said sample.

6. A corn plant, corn plant part, corn seed, or corn cell comprising the recombinant DNA molecule of claim 1.

7. The corn plant, corn plant part, corn seed, or corn cell of claim 6, wherein:

(a) the corn plant, corn plant part, corn seed, or corn cell exhibits reduced expression of at least a first endogenous gibberellin 20-oxidase (GA20ox) gene;

(b) the corn plant, corn plant part, corn seed, or corn cell has reduced expression of an endogenous gibberellin 20-oxidase 3 (GA20ox3) gene and an endogenous gibberellin 20-oxidase 5 (GA20ox5) gene;

(c) the corn plant, corn plant part, corn seed, or corn cell comprises corn event ZM_BCS216090, a representative sample of seed comprising said event having been deposited under ATCC Accession No. PTA-127050;

(d) the corn plant, corn plant part, corn seed, or corn cell is further defined as a progeny plant of any generation of a corn plant comprising corn event ZM_BCS216090, or a corn plant part, corn seed, or corn cell derived therefrom; or (e) the nucleotide sequence is present in chromosome 1 of the corn plant, corn plant part, corn seed, or corn cell.

8. The corn plant, corn plant part, corn seed, or corn cell of claim 7, wherein the gibberellin 20-oxidase (GA20ox) gene is selected from the group consisting of gibberellin 20-oxidase 3 (GA20ox3) and gibberellin 20-oxidase 5 (GA20ox5).

9. A corn plant, corn plant part, corn seed, or corn cell that comprises corn event ZM_BCS216090, a representative sample of seed comprising said event having been deposited under ATCC Accession No. PTA-127050.

10. The corn plant of claim 6, wherein said corn plant:

(a) has a reduced plant height relative to a control corn plant; or (b) has an increased lodging resistance relative to a control corn plant.

11. A DNA detection kit comprising:

a DNA probe comprising a polynucleotide segment of sufficient length to function as a DNA probe that hybridizes specifically under stringent hybridization conditions with corn event ZM_BCS216090 DNA in a sample, a representative sample of seed comprising said event having been deposited under ATCC Accession No. PTA-127050, wherein detecting hybridization of said DNA molecule under said stringent hybridization conditions is diagnostic for the presence of corn event ZM_BCS216090 DNA in said sample.

12. A method of producing a progeny corn plant comprising corn event ZM_BCS216090 comprising:

a) sexually crossing the corn plant of claim 9 with itself or a second corn plant;

b) collecting one or more seeds produced from said cross;

c) growing said seed to produce one or more progeny plants; and d) selecting at least a first progeny plant or seed comprising corn event ZM_BCS216090.

13. The method of claim 12, wherein the at least first progeny plant has a reduced plant height and/or increased lodging resistance relative to a control corn plant.

14. A hybrid corn plant or seed comprising corn event ZM_BCS216090, a representative sample of seed comprising said event having been deposited under ATCC Accession No. PTA-127050, produced by the method of claim 12.

15. The method of claim 12, further comprising:

e) collecting seed from said at least first progeny plant comprising corn event ZM_BCS216090.

16. A corn seed comprising a detectable amount of the recombinant DNA molecule of claim 1.

17. A nonliving corn plant material comprising a detectable amount of the recombinant DNA molecule of claim 1.

18. A microorganism comprising the recombinant DNA molecule of claim 1.

19. The microorganism of claim 18, wherein the microorganism is a plant cell.

20. A commodity product comprising the recombinant DNA molecule of claim 1.

21. The commodity product of claim 20, wherein said commodity product is produced from a transgenic corn plant, corn plant part, corn seed, or corn cell comprising corn event ZM_BCS216090, a representative sample of seed comprising said event having been deposited under ATCC Accession No. PTA-127050.

22. The commodity product of claim 20, further selected from the group consisting of whole or processed corn seed, animal feed comprising corn, corn oil, corn meal, corn flour, corn flakes, corn bran, corn biomass, and fuel products produced using corn and corn parts.

23. A method of producing a commodity product, said method comprising:

a) obtaining the corn plant of claim 9; and b) producing a commodity product from the transgenic corn plant, corn plant part, or corn seed.

24. A corn plant, corn plant part, or corn seed comprising a DNA molecule functional as a template when tested in a DNA amplification method producing an amplicon diagnostic for the presence of corn event ZM_BCS216090 DNA, a representative sample of seed comprising said event having been deposited under ATCC Accession No. PTA-127050, wherein the DNA molecule functional as a template comprises the nucleotide sequence of SEQ ID NO:1.

25. A method of determining the zygosity of a corn plant, corn plant part, or corn seed comprising corn event ZM_BCS216090 comprising:

a) contacting a sample comprising DNA from the corn plant, corn plant part, or corn seed with a probe set which contains at least a first probe that comprises the DNA molecule of claim 7 and specifically hybridizes to corn event ZM_BCS216090 and at least a second probe that specifically hybridizes to corn genomic DNA without corn event ZM_BCS216090 does not hybridize to corn event ZM_BCS216090 DNA; and b) hybridizing the probe set with the sample under stringent hybridization conditions, wherein detecting hybridization of only the first probe under the hybridization conditions is diagnostic for a corn plant, corn plant part, or corn seed homozygous for corn event ZM_BCS216090, and wherein detecting hybridization of both the first probe and the second probe under the hybridization conditions is diagnostic for a corn plant, corn plant part, or corn seed heterozygous for corn event ZM_BCS216090.

26. The method of claim 25, wherein the probe set comprises SEQ ID NO: 13 and SEQ ID NO: 16.

27. A method of producing a corn plant having reduced plant height or increased lodging resistance comprising: introducing corn event ZM_BCS216090 into a corn plant, a representative sample of seed comprising said event having been deposited under ATCC Accession No. PTA-127050, wherein corn event ZM_BCS216090 comprises the recombinant DNA molecule of claim 1.

28. A population of transgenic corn plants, wherein each transgenic corn plant comprises corn event ZM_BCS216090, a representative sample of seed comprising said event having been deposited under ATCC Accession No. PTA-127050.

29. The population of corn plants of claim 28, wherein said population of corn plants has a reduced plant height on average relative to a population of control corn plants lacking corn event ZM_BCS216090.

30. The population of corn plants of claim 28, wherein said population of corn plants has an increased lodging resistance on average relative to a population of control corn plants lacking corn event ZM_BCS216090.

31. The recombinant DNA molecule of claim 1, wherein the recombinant DNA molecule further comprises a nucleotide sequence selected from the group consisting of SEQ ID NO: 2, SEQ ID NO: 4, SEQ ID NO: 6, SEQ ID NO: 8, and a complete complement thereof.

32. The recombinant DNA molecule of claim 1, wherein the recombinant DNA molecule further comprises a nucleotide sequence selected from the group consisting of SEQ ID NO: 9, SEQ ID NO: 10, and a complete complement thereof.

33. The recombinant DNA molecule of claim 1, further comprising a nucleotide sequence selected from the group consisting of SEQ ID NO: 4, SEQ ID NO: 6, SEQ ID NO: 8, and a complete complement thereof.

* * * * *

```
                             SEQUENCE LISTING

Sequence total quantity: 18
SEQ ID NO: 1             moltype = DNA  length = 30
FEATURE                  Location/Qualifiers
misc_feature            1..30
                        note = A 30 nucleotide sequence representing the 5'
                         junction region ofcorn genomic DNA and the integrated
                         transgenic expressioncassette.
source                  1..30
                        mol_type = other DNA
                        organism = synthetic construct
SEQUENCE: 1
acgctggatc cgaaggacgt gtctacattc                                      30

SEQ ID NO: 2             moltype = DNA  length = 30
FEATURE                  Location/Qualifiers
misc_feature            1..30
                        note = A 30 nucleotide sequence representing the 3'
                         junction regions ofthe integrated transgenic expression
                         cassette and the corngenomic DNA.
source                  1..30
                        mol_type = other DNA
                        organism = synthetic construct
SEQUENCE: 2
ccgcacaaca aacgcgacga ctaacccgca                                      30

SEQ ID NO: 3             moltype = DNA  length = 60
FEATURE                  Location/Qualifiers
misc_feature            1..60
                        note = A 60 nucleotide sequence representing the 5'
                         junction region ofcorn genomic DNA and the integrated
                         transgenic expressioncassette.
source                  1..60
                        mol_type = other DNA
                        organism = synthetic construct
SEQUENCE: 3
taatccgggc catcgacgct ggatccgaag gacgtgtcta cattcacgtc caaatggggg  60

SEQ ID NO: 4             moltype = DNA  length = 60
FEATURE                  Location/Qualifiers
misc_feature            1..60
                        note = A 60 nucleotide sequence representing the 3'
                         junction region ofthe integrated transgenic expression
                         cassette and the corngenomic DNA.
source                  1..60
                        mol_type = other DNA
                        organism = synthetic construct
SEQUENCE: 4
gaggttgatt tgcggccgca caacaaacgc gacgactaac ccgcaaatgg cgcggctcgc  60

SEQ ID NO: 5             moltype = DNA  length = 100
FEATURE                  Location/Qualifiers
misc_feature            1..100
                        note = A 100 nucleotide sequence representing the 3'
                         junction region ofthe integrated transgenic expression
                         cassette and the corngenomic DNA.
source                  1..100
                        mol_type = other DNA
                        organism = synthetic construct
SEQUENCE: 5
ccgaaccgat aaccctcttc taatccgggc catcgacgct ggatccgaag gacgtgtcta  60
cattcacgtc caaatggggg cttagatgag aaacttcacg                         100

SEQ ID NO: 6             moltype = DNA  length = 100
FEATURE                  Location/Qualifiers
misc_feature            1..100
                        note = A 100 nucleotide sequence representing the 3'
                         junction region ofthe integrated transgenic expression
                         cassette and the corngenomic DNA.
source                  1..100
                        mol_type = other DNA
                        organism = synthetic construct
```

```
SEQUENCE: 6
ccacctcatt taaatagagt gaggttgatt tgcggccgca caacaaacgc gacgactaac  60
ccgcaaatgg cgcggctcgc cagagtaatg ctagggtggt                        100

SEQ ID NO: 7              moltype = DNA  length = 1180
FEATURE                  Location/Qualifiers
misc_feature             1..1180
                         note = A 1,180 nucleotide sequence representing 1,000
                          nucleotides of 5'flanking corn genomic DNA and 180
                          nucleotides of inserted T-DNA.
source                   1..1180
                         mol_type = other DNA
                         organism = synthetic construct
SEQUENCE: 7
gattaacaag aacattattg gttaaaaaag agtgatcaag ggcacaactt tccttcaacg  60
agctcctgct cagtatttc catctgctgg gtaccaggtt ccttggtcac ttgctcgtct  120
actcgtaaca atacaaacaa acatggtata ggagaaatta acatcacaac aaacatgagc  180
acaaactgca taataatgat ctatgcgttg ctacgagatc gtaggttcgg gaactactaa  240
attcggagtt aaagtaaaca agatatggtt ttccaaagtg taagtgacta taattcatgt  300
gaaaaatata ttaaacagta gtaactgata tattccaggt cataacttga tcctagctct  360
tgttttggtc aaacagtaat tatgagcaat ttaattcttg ctaaaagtta tttacataaa  420
cacaagctac atagatatct aattatagaa gtatgggaga tgtcacaatt agtactatta  480
atgcgtagat aattttatta cgaagataac gtaattggaa cgggttaaaa aggagttaaa  540
ataagtaaaa tatgaatttt acaagttttt agattcactt ttatattaaa cattcatttt  600
ccaatcttat ttacccaggt caaataatcc atggacagcg gacgcaaaaa ccagggcgtt  660
tagggttcag tttgcaaatt ccgggacctg ggggtaatga tctttgtgta caggtgtact  720
acgggttgat tagtaaaaac accagggctc ttatgaaaaa tcgcttggcc gaaagggtat  780
catgcaatca gggccatgga tcttggatct acggtcagga ttaaattatc gttactatga  840
atcgatattc aataggaacc ctaggatagg atatgcacga ctcagatttt atgttgacca  900
aatggacgtg gttcacccga tctatcatca acgctcctga ttccttactc ccgaaccgat  960
aaccctcttc taatccgggc catcgacgct ggatccgaag gacgtgtcta cattcacgtc  1020
caaatggggg cttagatgag aaacttcacg atttggcgcg actaactaag cactagcgta  1080
cgggacccag atatcgaatt caagcttata acttcgtata atgtatgcta tacgaagtta  1140
tgtcgactaa ctataacggt cctaaggtag cgacttaggc                        1180

SEQ ID NO: 8              moltype = DNA  length = 1107
FEATURE                  Location/Qualifiers
misc_feature             1..1107
                         note = A 1,107 nucleotide sequence representing 107
                          nucleotides ofinserted T-DNA and 1,000 nucleotides of 3'
                          flanking corn genomicDNA after the inserted T-DNA.
source                   1..1107
                         mol_type = other DNA
                         organism = synthetic construct
SEQUENCE: 8
cctgcaggtg tttaaactag ggataacagg gtaataggtc tcacgcggca aatcctacca  60
cctcatttaa atagagtgag gttgatttgc ggccgcacaa caaacgcgac gactaacccg  120
caaatggcgc ggctcgccag agtaatgcta gggtggtgca tcaatggata aaaacctgcc  180
gcacgcaggc acaaacgcta aagggaccaa tggcgaggaa gaacataggg gtagtttacg  240
gttgcccggt gcagggacga gcagttcacg ctccgcggta gcctggtccg gtcttctacg  300
tacgacgatg aagtcctgtt ctccagtcac caaacacgca agggaagccc ccaagcgtcc  360
agcgcgcgac cctgccgaac ccccagcttg acgccaagat tcaagggcag cggcagcggc  420
catttccaat gcgttctctc tccgtgggtc tattcccagc ggctatggct ctcagtactg  480
gttatgggcg catgatgcag agagatcaac cgagagtgtg cgatctggta tttattcagg  540
gagtccaggt tctgctgggg agggagatat tagctggcag actccaggct tgttgcaacg  600
gccaagtgga gttgtgagtt tgttgtgtcg gggcctcagc gaaggcgaag gtgctgacaa  660
gcggtcccca cggtgcagtg tgtgtggttg agcgcggcgt ggtgcgggag ccgtgcaatg  720
cggatccgga ttaggccggt gttgggctga acgagcagca aggagattca ggttgggttc  780
tgtttcattt ttatttttt ttctcttttc tctctatttt ttcatttcac aagcccaatt  840
ttttttcaaa tccaaacaag gttctaattc aaaaactcca taggtgcaaa ttattatttt  900
tgggatgtag tttaaccata tagtttatta tattatcgtt cactacttat ttgatttgga  960
aacaaagtaa catatagtct ttcatcacaa attacttgag ttcaattata tttaaaaat  1020
tatttctaat acaaattaaa tgaacagtca aaatctaagg catgatgcat aatttcaact  1080
tctatttcat ttttataggg aacatgt                                      1107

SEQ ID NO: 9              moltype = DNA  length = 2733
FEATURE                  Location/Qualifiers
misc_feature             1..2733
                         note = A 2,733 nucleotide sequence corresponding to the
                          transgenicinserted T-DNA of corn event ZM_BCS216090.
source                   1..2733
                         mol_type = other DNA
                         organism = synthetic construct
SEQUENCE: 9
gacgtgtcta cattcacgtc caaatggggg cttagatgag aaacttcacg atttggcgcg  60
actaactaag cactagcgta cgggacccag atatcgaatt caagcttata acttcgtata  120
atgtatgcta tacgaagtta tgtcgactaa ctataacggt cctaaggtag cgacttaggc  180
tgagcccggg caggcctacc cataataccc ataatagctc tttgccaatc gttcttcttg  240
gcgcgccaag acgcaaactc ggaccgacgg taccctcagc gctgtgcctg ttgcgatcct  300
```

-continued

```
acaaaaggga gtagtaatat ttaatgagct tgaaggagga tatcaactct ctccaaggtt    360
tattggagac ctttatgctc atggtttttat taaacaaata aacttcacaa ccaaggttcc    420
tgaagggcta ccgccaatca tagcggaaaa acttcaagac tataagttcc ctggatcaaa    480
taccgtctta atagaacgag agattcctcg ctggaacttc aatgaaatga aaagagaaac    540
acagatgagg accaacttat atatcttcaa gaattatcgc tgtttctatg gctattcacc    600
attaaggcca tacgaaccta taactcctga agaatttggg tttgattact acagttggga    660
aaatatggtt gatgaagacg aaggagaagt tgtatacatc tccaagtata ctaagattat    720
caaagtcact aaagagcatg catgggcttg gccagaacat gatggagaca caatgtcctg    780
caccacatca atagaaagatg aatggatcca tcgtatggac aatgcttaaa gaagctttat    840
caaaagcaac tttaagtacg aatcaataaa gaaggaccag aagatataaa gcgggaacat    900
cttcacatgc taccacatgg ctagcatctt tactttagca tctctattat tgtaagagtg    960
tataatgacc agtgtgcccc tggactccag tatataagga gcaccagagt agtgtaaatag   1020
atcatcgatc aagcaagcga gacgtcaaac ttctaagaga gcctgcagga ccaggtgggc   1080
ccaccgtctt cggtacgcgc tcactccgcc ctctgccttt gttactgcca cgtttctctg   1140
aatgctctct tgtgtggtga ttgctgagag tggtttagct ggatctagaa ttacactctg   1200
aaatcgtgtt ctgcctgtgc tgattacttg ccgtcctttg tagcagcaaa atatagggac   1260
atggtagtac gaaacgaaga tagaacctac acagcaatac gagaaatgtg taatttggtg   1320
cttagcggta tttatttaag cacatgttgg tgttataggg cacttggatt cagaagtttg   1380
ctgttaattt aggcacaggc ttcatactac atgggtcaat agtataggga ttcatattat   1440
aggcgatact ataataattt gttcgtctgc agagcttatt atttgccaaa attagatatt   1500
cctattctgt ttttgtttgt gtgctgttaa attgttaacg cctgaaggaa taaatataaa   1560
tgacgaaatt ttgatgttta tctctgctcc tttattgtga ccataagtca agatcagatg   1620
cacttgtttt aaatattgtt gtctgaagaa ataagtactg acagtatttt gatgcattga   1680
tctgcttgtt tgttgtaaca aaatttaaaa ataaagagtt tccttttttgt tgctctcctt   1740
acctcctgat ggtatctagt atctaccaac tgacactata ttgcttctct ttacatacgt   1800
atcttgctcg atgccttctc cctagtgttg accagtgtta ctcacatagt ctttgctcat   1860
ttcattgtaa tgcagatacc aagcggggca gagccgtgcc cgtctcatcc cctgcccgtg   1920
caagcagcta ggtaggacga tttgagcgtg gtgttaggcc gaaccgctga aggaagattg   1980
ctccactgtt gactgcatta gttgcaccgc atgatggaga aatgtattgc ttatattcag   2040
caatataatg ttcctccatc atccagtgca attaatatag tcgatagtgg aagaacggta   2100
acatatgtgg tttgcagcag gtgagcagga tgggtgtgga tgattgaata tctctgttca   2160
gtgtttttcat catctgactg aacactgaat cagcttgctg acgttagagg tttcagttta   2220
cctaatttat ggtctgtacc catgaaaagt gggaaaaggc tgaagaattc gatttctttc   2280
tttctttcaa tgtttcgcca gcagaacacg cgctgaggtt aattaatcca gggcgcctgc   2340
ttgtttgctg ccaagagagt gttttgtgta ctgctgctgc cgagaaatat atattttttt   2400
ctttcaccac ctcgtgtgca gcagttgttt tttgtttgga tggataaatg tttctagtac   2460
tgtggaggct gcatctgcat ctgtttgtaa atggatgaaa tatgaataaa aagttttgtt   2520
tctcataccc catgtgtctt gtgtttgcat gcacgccgtg ctagtttggt ttttggtttc   2580
tagagaaaac attttgtttg cttgtttctc tataggatgt gaagaacctg caggtgttta   2640
aactagggat aacagggtaa taggtctcac gcggcaaatc ctaccacctc atttaaatag   2700
agtgaggttg atttgcggcc gcacaacaaa cgc                                 2733
```

```
SEQ ID NO: 10            moltype = DNA   length = 4733
FEATURE                  Location/Qualifiers
misc_feature            1..4733
                         note = A 5,731 nucleotide sequence corresponding to the
                          contignucleotide sequence of the 5' genomic flanking DNA,
                          the insertedT-DNA, and the 3' flanking corn genomic DNA
                          corresponding toevent ZM_BCS216090.
source                  1..4733
                         mol_type = other DNA
                         organism = synthetic construct
SEQUENCE: 10
gattaacaag aacattattg gttaaaaaag agtgatcaag ggcacaactt tccttcaacg    60
agctcctgct cagtattttc catctgctgg gtaccaggtt ccttggtcac ttgctcgtct   120
actcgtaaca atacaaacaa acatggtata ggagaaatta acatcacaac aaacatgagc   180
acaaactgca taataatgat ctatgcgttg ctacgagatc gtaggttcgg gaactactaa   240
attcggagtt aaagtaaaca agatatggtt ttccaaagtg taagtgacta taattcatgt   300
gaaaaatata ttaaacagta gtaactgata tattccaggt cataacttga tcctagctct   360
tgttttggtc aaacagtaat tatgagcaat ttaattcttg ctaaaagtta tttacataaa   420
cacaagctac atagatatct aattatagaa gtatgggaga tgtcacaatt agtactatta   480
atgcgtagat aatttttatta cgaagataac gtaattggaa cgggtaaaaa aggagttaaa   540
ataagtaaaa tatgaatttt acaagttttt agattcactt ttatattaaa cattcatttt   600
ccaatcttat ttacccaggt caaataatcc atggacagcg gacgcaaaaa ccagggcgtt   660
tagggttcag tttgcaaatt ccgggacctg ggggtaatga tctttgtgta caggtgtact   720
acgggttgat tagtaaaaac accagggctc ttatgaaaaa tcgcttggcc gaaagggtat   780
catgcaatca gggccatgga tcttggatct acggtcagga ttaaattatc gttactatga   840
atcgatattc aataggaacc ctaggatagg atatgcacga ctcagatttt atgttgacca   900
aatggacgtg gttcacccga tctatcatca acgctcctga ttccttactc ccgaaccgat   960
aaccctcttc taatccgggc catcgacgct ggatccgaag gacgtgtcta cattcacgtc   1020
caaatggggg cttagatgag aaacttcacg atttggcgcg actaactaag cactacgta   1080
cgggacccag atatcgaatt caagcttata acttcgtata atgtatgcta tacgaagtta   1140
tgtcgactaa ctataacggt cctaaggtag cgacttaggc tgagcccggg caggcctacc   1200
cataataccc ataatagctg tttgccaatc gttcttcttg gcgcgccaag acgcaaactc   1260
ggaccgacgg taccctcagc gctgtgcctg ttgcgatcct acaaaaggga gtagtaatat   1320
ttaatgagct tgaaggagga tatcaactct ctccaaggtt tattggagac ctttatgctc   1380
atggtttttat taaacaaata aacttcacaa ccaaggttcc tgaagggcta ccgccaatca   1440
tagcggaaaa acttcaagac tataagttcc ctggatcaaa taccgtctta atagaacgag   1500
agattcctcg ctggaacttc aatgaaatga aaagagaaac acagatgagg accaacttat   1560
```

-continued

```
atatcttcaa gaattatcgc tgtttctatg gctattcacc attaaggcca tacgaaccta  1620
taactcctga agaatttggg tttgattact acagttggga aaaatatggtt gatgaagacg  1680
aaggagaagt tgtatacatc tccaagtata ctaagattat caaagtcact aaagagcatg  1740
catgggcttg gccagaacat gatggagaca caatgtcctg caccacatca atagaagatg  1800
aatggatcca tcgtatggac aatgcttaaa gaagctttat caaaagcaac tttaagtacg  1860
aatcaataaa gaaggaccag aagatataaa gcgggaacat cttcacatgc taccacatgg  1920
ctagcatctt tactttagca tctctattat tgtaagagtg tataatgacc agtgtgcccc  1980
tggactccag tatataagga gcaccagagt agtgtaatag atcatcgatc aagcaagcga  2040
gacgtcaaac ttctaagaga gcctgcagga ccaggtgggc ccaccgtctt cggtacgcgc  2100
tcactccgcc ctctgccttt gttactgcca cgtttctctg aatgctctct tgtgtggtga  2160
ttgctgagag tggtttagct ggatctagaa ttacactctg aaatcgtgtt ctgcctgtgc  2220
tgattacttg ccgtcctttg tagcagcaaa atatagggac atggtagtac gaaacgaaga  2280
tagaacctac acagcaatac gagaaatgtg taatttggtg cttagcggta tttatttaag  2340
cacatgttgg tgttataggg cacttggatt cagaagtttg ctgttaattt aggcacaggc  2400
ttcatactac atgggtcaat agtataggga ttcatattat aggcgatact ataataattt  2460
gttcgtctgc agagcttatt atttgccaaa attagatatt cctattctgt ttttgtttgt  2520
gtgctgttaa attgttaacg cctgaaggaa taaatataaa tgacgaaatt ttgatgttta  2580
tctctgctcc tttattgtga ccataagtca agatcagatg cacttgtttt aaatattgtt  2640
gtctgaagaa ataagtactg acagtatttt gatgcattga tctgcttgtt tgttgtaaca  2700
aaatttaaaa ataaagagtt tccttttttgt tgctctcctt acctcctgat ggtatctagt  2760
atctaccaac tgacactata ttgcttctct ttacatacgt atcttgctcg atgccttctc  2820
cctagtgttg accagtgtta ctcacatagt ctttgctcat ttcattgtaa tgcagatacc  2880
aagcgggggca gagccgtgcc cgtctcatcc cctgcccgtg caagcagcta ggtaggacga  2940
tttgagcgtg gtgttaggcc gaaccgctga aggaagattg ctccactgtt gactgcatta  3000
gttgcaccgc atgatggaga aatgtattgc ttatattcag caatataatg ttcctccatc  3060
atccagtgca attaatatag tcgatagtgg aagaacggta acatatgtgg tttgcagcag  3120
gtgagcagga tgggtgtgga tgattgaata tctctgttca gtgtttttcat catctgactg  3180
aacactgaat cagcttgctg acgttagagg tttcagttta cctaatttat ggtctgtacc  3240
catgaaaagt gggaaaaggc tgaagaattc gatttctttc tttctttcaa tgtttcgcca  3300
gcagaacacg cgctgaggtt aattaatcca gggcgcctgc ttgtttgctg ccaagagagt  3360
gttttgtgta ctgctgctgc cgagaaatat atattttttt cttttcaccac ctcgtgtgca  3420
gcagttgttt tttgtttgga tggataaatg tttctagtac tgtggaggct gcatctgcat  3480
ctgtttgtaa atggatgaaa tatgaataaa aagttttgtt tctcataccc catgtgtctt  3540
gtgtttgcat gcacgccgtg ctagtttggt ttttggtttc tagagaaaac attttgtttg  3600
cttgtttctc tataggatgt gaagaacctg caggtgttta aactagggat aacagggtaa  3660
taggtctcac gcggcaaatc ctaccacctc atttaaatag agtgaggttg atttgcggcc  3720
gcacaacaaa cgcgacgact aacccgcaaa tggcgcggct cgccagagta atgctagggt  3780
ggtgcatcaa tggataaaaa cctgccgcac gcaggcacaa acgctaaagg gaccaatggc  3840
gaggaagaac ataggggtag tttacggttg cccggtgcag ggacgagcag ttcacgctcc  3900
gcggtagcct ggtccggtct tctacgtacg acgatgaagt cctgttctcc agtcaccaaa  3960
cacgcaaggg aagcccccaa gcgtccagcg cgcgaccctg ccgaaccccc agcttgacgc  4020
caagattcaa gggcagcggc agcggccatt tccaatgcgt tctctctccg tgggtctatt  4080
cccagcggct atggctctca gtactggtta tgggcgcatg atgcagagag atcaaccgag  4140
agtgtgcgat ctggtatta ttcagggagt ccaggttctg ctggggaggg agatatattagc  4200
tggcagactc caggcttgtt gcaacggcca agtggagttg tgagtttgtt gtgtcggggc  4260
ctcagcgaag gcgaaggtgc tgacaagcgg tccccacggt gcagtgtgtg tggttgagcg  4320
cggcgtgctg cgggagccgt caatgcggga tccggattag gccggtgttg ggcgaacga  4380
gcagcaagga gattcaggtt gggttctgtt tcatttttat tttttttct cttttctctc  4440
tattttttca tttcacaagc ccaatttttt ttcaaatcca aacaaggttc taattcaaaa  4500
actccatagg tgcaaattat tattttttggg atgtagttta accatatagt ttattatatt  4560
atcgttcact acttatttga tttggaaaca aagtaacata tagtctttca tcacaaatta  4620
cttgagttca attatatttt aaaaattatt tctaatacaa attaaatgaa cagtcaaaat  4680
ctaaggcatg atgcataatt tcaacttcta tttcattttt atagggaaca tgt          4733
```

```
SEQ ID NO: 11            moltype = DNA  length = 19
FEATURE                  Location/Qualifiers
misc_feature             1..19
                         note = A 19 nucleotide sequence corresponding to the
                         thermalamplification primer, SQ51606 used to identify corn
                         eventZM_BCS216090 DNA in a sample.
source                   1..19
                         mol_type = other DNA
                         organism = synthetic construct
SEQUENCE: 11
atcgacgctg gatccgaag                                                   19

SEQ ID NO: 12            moltype = DNA  length = 21
FEATURE                  Location/Qualifiers
misc_feature             1..21
                         note = A 21 nucleotide sequence corresponding to a thermal
                         amplificationprimer, SQ51629 used to identify corn event
                         ZM_BCS216090 DNA in asample.
source                   1..21
                         mol_type = other DNA
                         organism = synthetic construct
SEQUENCE: 12
ttagttagtc gcgccaaatc g                                                21

SEQ ID NO: 13            moltype = DNA  length = 19
```

-continued

```
FEATURE                  Location/Qualifiers
misc_feature             1..19
                         note = A 19 mic;eptode seqiemce cprres[pmdomg tp a [rpbe
                          referred tp asPB50583 used to identify corn event
                          ZM_BCS216090 DNA in a sample.
source                   1..19
                         mol_type = other DNA
                         organism = synthetic construct
SEQUENCE: 13
aagtttctca tctaagccc                                                    19

SEQ ID NO: 14            moltype = DNA  length = 24
FEATURE                  Location/Qualifiers
misc_feature             1..24
                         note = A 24 nucleotide sequence corresponding to a thermal
                          amplificationprimer referred to as SQ20222 used as an
                          internal control for theevent and zygosity assay for corn
                          event ZM_BCS216090.
source                   1..24
                         mol_type = other DNA
                         organism = synthetic construct
SEQUENCE: 14
gccctatgac ttaccgagag ttca                                              24

SEQ ID NO: 15            moltype = DNA  length = 28
FEATURE                  Location/Qualifiers
misc_feature             1..28
                         note = A 28 nucleotide sequence corresponding to a thermal
                          amplificationprimer referred to as SQ20221 used as an
                          internal control for theevent and zygosity assay for corn
                          event ZM_BCS216090.
source                   1..28
                         mol_type = other DNA
                         organism = synthetic construct
SEQUENCE: 15
gttgctatgt actaacagaa ctgcatgt                                          28

SEQ ID NO: 16            moltype = DNA  length = 17
FEATURE                  Location/Qualifiers
misc_feature             1..17
                         note = A 17 nucleotide sequence corresponding to a probe
                          referred to asPB50298 used as an internal control for the
                          event and zygosityassay for corn event ZM_BCS216090.
source                   1..17
                         mol_type = other DNA
                         organism = synthetic construct
SEQUENCE: 16
ttgttgtgtg gctccat                                                      17

SEQ ID NO: 17            moltype = DNA  length = 1000
FEATURE                  Location/Qualifiers
misc_feature             1..1000
                         note = A 1,000 nucletodie sequence of the 5' flanking corn
                          genomic DNAup to the inserted T-DNA in event ZM-BCS216090.
source                   1..1000
                         mol_type = genomic DNA
                         organism = Zea mays
SEQUENCE: 17
gattaacaag aacattattg gttaaaaaag agtgatcaag ggcacaactt tccttcaacg  60
agctcctgct cagtattttc catctgctgg gtaccaggtt ccttggtcac ttgctcgtct  120
actcgtaaca atacaaacaa acatggtata ggagaaatta acatcacaac aaacatgagc  180
acaaactgca taataatgat ctatgcgttg ctacgagatc gtaggttcgg gaactactaa  240
attcggagtt aaagtaaaca agatatggtt ttccaaagtg taagtgacta taattcatgt  300
gaaaaatata ttaaacagta gtaactgata tattccaggt cataacttga tcctagctct  360
tgttttggtc aaacagtaat tatgagcaat ttaattcttg ctaaaagtta tttacataaa  420
cacaagctac atagatatct aattatagaa gtatgggaga tgtcacaatt agtactatta  480
atgcgtagat aattttatta cgaagataac gtaattggaa cgggtaaaa aggagttaaa  540
ataagtaaaa tatgaatttt acaagttttt agattcactt ttatattaaa cattcatttt  600
ccaatcttat ttacccaggt caaataatcc atggacagcg gacgcaaaaa ccagggcgtt  660
tagggttcag tttgcaaatt ccgggacctg ggggtaatga tctttgtgta caggtgtact  720
acgggttgat tagtaaaaac accagggctc ttatgaaaaa tcgcttggcc gaaagggtat  780
catgcaatca gggccatgga tcttggatct acggtcagga ttaaattatc gttactatga  840
atcgatattc aataggaacc ctaggatagg atatgcacga ctcagatttt atgttgacca  900
aatgacgtg gttcacccga tctatcatca acgctcctga ttccttactc ccgaaccgat  960
aaccctcttc taatccgggc catcgacgct ggatccgaag                        1000

SEQ ID NO: 18            moltype = DNA  length = 1000
FEATURE                  Location/Qualifiers
misc_feature             1..1000
```

-continued

```
                    note = A 1,000 nucleotide sequence of the 3' flanking corn
                     genomic DNAimmediately after the inserted T-DNA in event
                     ZM-BCS216090.
source              1..1000
                    mol_type = genomic DNA
                    organism = Zea mays
SEQUENCE: 18
gacgactaac  ccgcaaatgg  cgcggctcgc  cagagtaatg  ctagggtggt  gcatcaatgg    60
ataaaaacct  gccgcacgca  ggcacaaacg  ctaaagggac  caatggcgag  gaagaacata   120
ggggtagttt  acggttgccc  ggtgcaggga  cgagcagttc  acgctccgcg  gtagcctggt   180
ccggtcttct  acgtacgacg  atgaagtcct  gttctccagt  caccaaacac  gcaagggaag   240
cccccaagcg  tccagcgcgc  gaccctgccg  aaccccagc   ttgacgccaa  gattcaaggg   300
cagcggcagc  ggccatttcc  aatgcgttct  ctctccgtgg  gtctattccc  agcggctatg   360
gctctcagta  ctggttatgg  gcgcatgatg  cagagagatc  aaccgagagt  gtgcgatctg   420
gtatttattc  agggagtcca  ggttctgctg  gggagggaga  tattagctgg  cagactccag   480
gcttgttgca  acggccaagt  ggagttgtga  gtttgttgtg  tcggggcctc  agcgaaggcg   540
aaggtgctga  caagcggtcc  ccacggtgca  gtgtgtgtgg  ttgagcgcgg  cgtggtgcgg   600
gagccgtgca  atgcggatcc  ggattaggcc  ggtgttgggc  tgaacgagca  gcaaggagat   660
tcaggttggg  ttctgtttca  tttttatttt  tttttctctt  ttctctctat  tttttcattt   720
cacaagccca  atttttttc   aaatccaaac  aaggttctaa  ttcaaaaact  ccataggtgc   780
aaattattat  ttttgggatg  tagtttaacc  atatagttta  ttatattatc  gttcactact   840
tatttgattt  ggaaacaaag  taacatatag  tctttcatca  caaattactt  gagttcaatt   900
atattttaaa  aattatttct  aatacaaatt  aaatgaacag  tcaaaatcta  aggcatgatg   960
cataatttca  acttctattt  cattttata   gggaacatgt                           1000
```